(12) United States Patent
Ben-Haim et al.

(10) Patent No.: US 6,463,324 B1
(45) Date of Patent: Oct. 8, 2002

(54) CARDIAC OUTPUT ENHANCED PACEMAKER

(75) Inventors: Shlomo Ben-Haim; Nissim Darvish; Yuval Mika, all of Haifa; Maier Fenster, Petach Tikva, all of (IL)

(73) Assignee: Impulse Dynamics N. V., Curacao (NL)

( * ) Notice: Subject to any disclaimer, the term of this patent is extended or adjusted under 35 U.S.C. 154(b) by 0 days.

(21) Appl. No.: 09/254,900

(22) PCT Filed: Jul. 9, 1997

(86) PCT No.: PCT/IL97/00236

§ 371 (c)(1),
(2), (4) Date: Mar. 12, 1999

(87) PCT Pub. No.: WO98/10832

PCT Pub. Date: Mar. 19, 1998

Related U.S. Application Data

(60) Provisional application No. 60/026,392, filed on Sep. 16, 1996.

(30) Foreign Application Priority Data

Sep. 17, 1996 (IL) .................................................. 119261

(51) Int. Cl.[7] .............................................. A61N 1/365
(52) U.S. Cl. ............................................. 607/9; 607/17
(58) Field of Search ............................... 607/9, 11, 4, 5, 607/17–25, 68

(56) References Cited

U.S. PATENT DOCUMENTS

| | | |
|---|---|---|
| 4,554,922 A | 11/1985 | Prystowsky et al. |
| 5,083,564 A | 1/1992 | Sherlag |
| 5,205,284 A | 4/1993 | Freeman |
| 5,568,809 A | 10/1996 | Ben-Haim |
| 5,800,464 A | 9/1998 | Kieval |
| 5,814,079 A | 9/1998 | Kieval |
| 5,871,506 A | 2/1999 | Mower |

FOREIGN PATENT DOCUMENTS

| | | |
|---|---|---|
| EP | 0727241 | 8/1996 |
| WO | WO 97/25098 | 7/1997 |
| WO | WO 97/25101 | 7/1997 |
| WO | WO 98/10828 | 3/1998 |
| WO | WO 98/10829 | 3/1998 |
| WO | WO 98/10830 | 3/1998 |
| WO | WO 98/10831 | 3/1998 |

OTHER PUBLICATIONS

H. Antoni, et al., Polarization Effects of Sinusoidal 50–Cycle Alternating Current on Membrane Potential of Mammalian Cardiac Fibres, Pflugers Arch. 314, pp. 274–291 (1970).

Sutton and Bourgeois, "the Foundations of Cardiac Pacing", p. 73.

*Primary Examiner*—Jeffrey R. Jastrzab
(74) *Attorney, Agent, or Firm*—Reed Smith LLP

(57) ABSTRACT

This invention is an apparatus for heart packing with cardiac output modification, including one or more electrodes (27, 29) which apply electrical signals to muscle. Signal generation circuitry (26) applies an excitatory electrical pulse to at least one of the one or more electrodes to pace the heart and a non-excitatory stimulation pulse to at least one of the one or more electrode s to modify the cardiac output. Preferably the circuitry synchronizes the non-excitatory stimulation pulse with the pacing pulse.

16 Claims, 52 Drawing Sheets

CARDIAC OUTPUT ENHANCED PACEMAKER

CROSS-REFERENCES TO RELATED APPLICATIONS

This application is a U.S. National Phase filing of PCT application No. PCT/IL97/00236, filed Jul. 9, 1997, which is in turn based upon U.S. provisional Patent application Ser. No. 60/026,392, filed Sep. 16, 1996 and Israeli Pat. application No. 119,261, filed Sep. 17, 1996, the complete disclosures of which are hereby incorporated by reference.

FIELD OF THE INVENTION

The present invention relates generally to cardiac therapeutic devices, and specifically to cardiac pacemakers.

BACKGROUND OF THE INVENTION

The heart is a muscular pump whose mechanical activation is controlled by electrical stimulation generated at the right atrium and passed to the entire heart. In a normal heart the electrical stimulation originates as action potentials in a group of pacemaker cells lying in a sino-atrial (SA) node in the right atrium. In certain heart diseases, either congenital or acquired, natural pacing is replaced or assisted by artificial pacing induced by an implanted pacemaker. Pacemakers known in the art provide artificial excitatory pulses to the heart tissue, to control the heart rhythm.

Cardiac output, i.e., the output of the heart per unit time, is the product of stroke volume and heart rate. Hence, variations in cardiac output can be produced by changes in cardiac rate or stroke volume. The stroke volume can be influenced, for example, by changing the efficacy of cardiac contraction, by changing the length of the cardiac muscle fibers, and by changing contractility of cardiac muscle independent of fiber length. The heart rate and rhythm influence the cardiac output both directly and indirectly, since changes in the rate and rhythm also affect myocardial contractility.

The human body normally regulates the cardiac output in response to physiological needs, mainly by changing the heart rate, as during physical exercise, and/or by adapting the stroke volume. Under pathological conditions, however, some of the regulatory mechanisms may be damaged.

Artificially paced hearts typically lose more than 30% of their normal cardiac output, presumably due to loss of efficient contraction under artificial, as opposed to natural, electrical stimulation. In the context of the present patent application, this reduction is referred to as pacing-induced cardiac output (PICO) loss.

Moreover, when pacing is indicated, it is frequently in the wake of heart disease, particularly ischemic heart disease (IHD), including cases of myocardial infarction (MI), which in itself reduces the cardiac output. Such reduction is referred to in the context of the present patent application as global cardiac output (GCO) loss.

While electronic pacemakers can increases cardiac output temporarily by increasing the heart rate, this increase is at the expense of greater energy expenditure by the heart muscle, which the heart disease patient cannot generally sustain. Although modern pacemakers may include stimulation at two or more points and allow optimization of the excitatory pulse amplitudes, rate and timing, they do not address directly the loss of cardiac output caused by the pacing, nor do they address the loss due to cardiac pathology. These losses are mainly related to reduction in the stroke volume, which cardiac pacing tends to exacerbate. Defibrillators are useful in treating arrhythmia when it occurs (although they are painful to the patient and traumatic to the heart), but they provide no long-term amelioration of cardiac insufficiency. Thus, none of the treatments known in the art allow effective, long-term regulation of cardiac output, because they are aimed at controlling the heart rate and do not address the need to increase the stroke volume and the efficiency of contraction of the heart.

The electromechanical properties of the heart, as well as methods known in the art for influencing these properties, are more fully described in the "Background of the Invention" section of PCT patent application PCT/IL97/00012, which is assigned to the assignee of the present patent application, and whose disclosure is incorporated herein by reference.

SUMMARY OF THE INVENTION

The inventors have found that by applying non-excitatory electrical stimulation pulses to cardiac muscle segments, appropriately timed with respects the heart's electrical activation, it is possible to regulate the cardiac output.

It is therefore an object of the present invention to provide devices that allow both artificial heart pacing and effective regulation of cardiac output, and particularly devices that increase the cardiac output by enhancing the heart's stroke volume.

The present invention thus provides thus provides apparatus for heart pacing with cardiac output regulation, including one or more implantable electrodes, which apply electrical signals to cardiac muscle segments, and signal generation circuitry, which applies an excitatory electrical pulse to at least one of the one or more electrodes to pace the heart and a non-excitatory stimulation pulse to at least one of the one or more electrodes to regulate the cardiac output.

Another aspect of the present invention relates to a method for heart pacing with cardiac output enhancement, including implanting one or more electrodes in a subject's heart; applying an excitatory electrical pulse to at least one of the one or more electrodes to pace the heart; and applying a non-excitatory stimulation pulse to at least one of the one or more electrodes to regulate an efficacy of cardiac contraction.

The term "non-excitatory electrical stimulation", in the context of the present patent application and in the claims, refers to electrical pulses that do not induce new activation potentials to propagate in cardiac muscle cells. Rather, such pulses affect the response of the heart muscle to the action potentials, by modulating cell contractility within selected segments of the cardiac muscle. Specifically, as described in the above-mentioned PCT patent application PCT/IL97/00012 and incorporated herein by reference, the inventors have found that by applying non-excitatory electrical stimulation pulses of suitable strength, appropriately timed with respect to the heart's electrical activation, the contraction of the selected segments can be increased or decreased, thus increasing or decreasing the stroke volume of the heart. This finding forms the basis for the present invention.

According to preferred embodiments of the present invention, the non-excitatory stimulation pulse is coupled to the activity of a pacemaker, and in various embodiments, the non-excitatory stimulation pulse is synchronized by pacing pulses generated by the pacemaker. In other embodiments of the present invention, one or more sensors are provided in the apparatus to sense local activity in the heart tissue, to enable the non-excitatory stimulation pulse to be triggered independently of the pacemaker, particularly when the pacemaker is inactive for a period of time, as is known in the art, for example, with regard to VVI and DDD pacemakers.

In preferred embodiments of the present invention, a cardiac output enhanced pacemaker (COEP) comprises a pacing unit and a non-excitatory stimulation unit. The pacing unit provides pacing pulses to the heart muscle for controlling the heart rate, as is known in the art. The non-excitatory stimulation unit provides stimulation pulses to at least a segment of the heart muscle, synchronized with the pacing pulses, so as to enhance the response of the muscle to the pacing pulses, preferably to increase the heart's stroke volume. Each of the two units comprises one or more electrodes to be implanted in a subject's heart and signal generation circuitry coupled thereto. The circuitry is preferably encased in an implantable case, similar to those used in pacemakers known in the art, and preferably uses a similar type of battery as a power source.

Thus, in preferred embodiments of the present invention, the COEP device applies both excitatory electrical stimulation, to pace the heart by generating activation potentials in the cardiac muscle tissue, a non-excitatory stimulation, to control response of the muscle to the activation potentials. In this respect, the device differs fundamentally from pacemakers and other implantable cardiac electronic devices known in the art, which provide only excitatory stimulation. When the COEP is used to pace the heart, the activation of the heart with respect to the pacing is substantially the same as it would be if an ordinary pacemaker were used. By applying non-excitatory stimulation to the heart, however, the COEP allows cardiac output to be regulated to demand by controlling the stroke volume, as well as the heart rate. It is preferably used to compensate for the loss of cardiac output that commonly results from the pacing, and may also be used to treat problems of low cardiac output due to other cardiac pathologies.

Preferably, the COEP device can be controlled to apply both excitatory and non-excitatory stimulation together, or to apply either excitatory or non-excitatory stimulation alone, depending on the therapeutic needs and condition of the patient. Thus, for example, the excitatory stimulation could be applied at substantially all hours of the day and night, while the non-excitatory stimulation is applied only during daytime hours, when the patient needs a boost in cardiac output, or at any other desired times. Parameters of the excitatory and non-excitatory stimulation are preferably adjusted together, so as to cooperatively achieve a desired therapeutic effect.

Although in describing some aspects of the present invention, the pacing and non-excitatory stimulation units are, for clarity of explanation, referred to as separate entities, in some preferred embodiments of the present invention, these units are implemented using a common, preferably integrated, electronic circuitry. Similarly, in some preferred embodiments of the present invention, the same electrodes may be used to apply both the pacing and non-excitatory stimulation pulses. Furthermore, while preferred embodiments of the present invention are described herein with reference to the COEP device, certain aspects of the present invention may be accomplished by suitably modifying and/or reprogramming an existing pacemaker, so as to apply non-excitatory stimulation pulses in addition to the pacing pulses that the pacemaker normally generates. It will be appreciated that such embodiments and modifications fall within the scope of the present invention.

In some preferred embodiments of the present invention the pacing unit comprises multiple pacing electrodes to allow for pacing optimization, as is known in the art. More generally, it will be understood that the principles of the present invention may be applied to produce COEP devices that apply non-excitatory stimulation to achieve cardiac output regulation in conjunction with any suitable mode of pacing, including adaptive and rate-responsive pacing modes known in the art.

In preferred embodiments of the present invention, the non-excitatory stimulation unit comprises electrodes having a relatively large contact area with the heart, preferably at least 5 $mm^2$, more preferably at least 1 $cm^2$, most preferably at least 4 $cm^2$, and preferably comprising carbon or another conductive material. Alternatively or additionally, the non-excitatory stimulation unit may comprise a plurality of stimulation electrodes, preferably a stimulation net, comprising a plurality of interconnected, addressable electrodes, covering a substantial heart segment, such that the size of the segment of the heart to which a non-excitatory signal is applied may be modulated. Considerations relating to the design of the electrodes and various preferred embodiments thereof are described in the above-mentioned '012 PCT application and the PCT patent application filed on even date, entitled "Cardiac Output Controller," and incorporated herein by reference.

Although generally the non-excitatory stimulation unit is triggered responsive to the pacing pulses generated by the pacing unit, in some preferred embodiments of the present invention, the COEP comprises one or more sensors, preferably sensing electrodes, which sense local electrical activity in the heart tissue. Alternatively or additionally, one or more of the stimulation electrodes may also serve as sensing electrodes. The signals sensed by the sensing electrodes are received by the circuitry and are used to trigger the non-excitatory stimulation unit and, alternatively or additionally, may be used by the pacing unit in adaptive pacing modes. Additionally, the circuitry may analyze the signals, for example, to determine the QT interval, so as to adjust the stimulation pulses responsive thereto.

Further alternatively, a body surface electrode may be used to detect an ECG signal, which is then used to synchronize the non-excitatory stimulation pulses. Other types of sensors may also be used for this purpose, for example, a pressure sensor or other mechanical sensor in or on the heart, which senses heart muscle activity.

In some preferred embodiments of the present invention, one or more of the pacing electrodes and one or more of the non-excitatory stimulation electrodes are placed in two or more different heart chambers. Preferably, the pacing electrode is implanted in the right ventricle and the non-excitatory stimulation electrode, in the left ventricle. Alternatively, all electrodes may be located in the same chamber of the heart. Further alternatively, one or more of the electrodes may be placed epicardially, on an outer wall of one of the chambers, or may be implanted in the myocardium.

In a preferred embodiment of the present invention, the non-excitatory stimulation electrodes are placed on the heart wall in close proximity to coronary blood vessels. The inventors have found that placing the electrodes in proximity to the blood vessels generally increases the effectiveness of the non-stimulatory excitation pulses in enhancing stroke volume and contraction efficiency.

In some preferred embodiments of the present invention, optimal placement of the electrodes is determined with reference to a map of local cardiac activity and/or viability. Preferably, before insertion of the electrodes, a map of the heart is produced, for example, an electrophysiological map, as described in U.S. Pat. No. 5,568,809, or a phase-dependent geometrical map, as described in PCT Patent Application PCT/IL97/00011, which is assigned to the assignee of the present patent application, both of which documents are incorporated herein by reference. The electrodes are then positioned responsive to the map. Alternatively or additionally, at the time of implantation of the electrodes, their positions are varied and the results of the variation on hemodynamics are observed, in order to find optimal, fixed positions for the electrodes.

In some preferred embodiments of the present invention, the non-excitatory stimulation pulse is applied between the pacing and the non-excitatory stimulation electrodes. Alternatively, the non-excitatory stimulation pulse may be applied between the. non-excitatory stimulation electrode and the signal generation circuitry case or across a bipolar non-excitatory stimulation electrode.

In some preferred embodiments of the present invention, the extent of change in cardiac output is controlled by changing the characteristics of the non-excitatory stimulation pulse. This is achieved by changing the strength of the electrical signal applied to the heart, i.e., the pulse voltage or current, the pulse timing, the pulse duration and the pulse waveform and frequency thereof, as described in the '012 PCT application, mentioned above. In particular, the inventors have found that the shape of the non-excitatory signal can determine the magnitude of an increase or decrease in cardiac output.

In alternative preferred embodiments of the present invention, the COEP device may further include one or more physiological sensors, such as, for example, blood flow rate detectors, ventricular pressure detectors, etc., in order to assess cardiac output and to adjust its regulation as needed. Such adjustment may be performed internally, by the signal generation circuitry itself. Alternatively, an external telemetry unit may monitor physiological parameters related to the operation of the COEP device, and may then reprogram the device in response to the values of the parameters.

Further aspects of the present invention are also described in the above-mentioned PCT patent application entitled "Cardiac Output Controller," filed on even date and incorporated herein by reference. Other aspects of the use of the COEP device are described further in a PCT patent application PCT/IL97/00231 entitled, "Apparatus and Method for Controlling, the Contractility of Muscles," filed on even date, which is assigned to the assignee of the present patent application, and whose disclosure is incorporated herein by reference.

Preferred embodiments of the present invention may also be used in conjunction with suitable drugs, as described in a PCT parent application PCT/IL97/00232 entitled "Drug-Device Combination for Controlling, the Contractility of Muscles", and in conjunction with devices and methods for preventing cardiac fibrillation, as described in a PCT patent application PCT/IL97/00233 entitled "Fencing of Cardiac Muscles", both filed on even date and assigned to the assignee of the present application. The disclosures of these applications are also incorporated herein by reference.

There is therefore provided, in accordance with a preferred embodiment of the present invention, apparatus for heart pacing with cardiac output modification, including:

one or more electrodes, which apply electrical signals to cardiac muscle segments; and signal generation circuitry, which applies an excitatory electrical pulse to at least one of the one or more electrodes to pace the heart and a non-excitatory stimulation pulse to at least one of the one or more electrodes to modify the cardiac output.

Preferably, the circuitry synchronizes the non-excitatory stimulation pulse with the pacing pulse, most preferably by introducing a predetermined time offset between the pacing pulse and the non-excitatory stimulation pulse. In a preferred embodiment of the invention, the circuitry generates a sequence of multiple non-excitatory stimulation pulses, at predetermined respective delays relative to the pacing, pulse.

Preferably, the one or more electrodes include a bipolar non-excitatory stimulation electrode, across which the non-excitatory stimulation pulse is applied.

Additionally or alternatively, the one or more electrodes include a pacing electrode and a non-excitatory stimulation electrode, and the non-excitatory stimulation pulse is applied between the non-excitatory stimulation electrode and the pacing electrode.

Preferably, the signal generation circuitry is encased in an implantable case, and the non-excitatory stimulation pulse is preferably applied between one of the one or more electrodes and the implantable case.

In a preferred embodiment of the invention, the apparatus includes at least one sensor, which senses cardiac activity, preferably an electrode, which senses cardiac electrical activity. The sensor is coupled to the signal generation circuitry, which generates the pulses responsive thereto. Preferably, the signal generation circuitry interrupts application of the excitatory pulse, while generating the non-excitatory pulse responsive to the sensor. Additionally or alternatively, the circuitry detects a QT interval in the cardiac electrical activity.

Further additionally or alternatively, the sensor includes a pressure sensor and/or a flow rate sensor and/or an oxygen sensor and/or a temperature sensor.

Preferably, the signal generation circuitry varies one or more parameters of the non-excitatory stimulation pulse, from the group of parameters including voltage, current, duration, timing delay, waveform and waveform frequency.

Additionally or alternatively, after the non-excitatory stimulation pulse, the signal generation circuitry generates another pulse of opposite polarity to the stimulation pulse, which is applied to the cardiac muscle segment by the non-excitatory stimulation electrode.

Preferably, the one or more electrodes include at least one non-excitatory stimulation electrode having an area of at least 5 $mm^2$, more preferably at least 1 $cm^2$, and most preferably at least 4 $cm^2$.

In a preferred embodiment of the invention, the at least one non-excitatory stimulation electrode includes a net of addressable electrodes. In a further preferred embodiment, the signal generation circuitry varies the extent of a portion of the area of the heart segment to which the non-excitatory stimulation pulse is applied.

In another preferred embodiment of the invention, the apparatus includes a telemetry unit, which receives data indicative of cardiac function and programs the signal generation circuitry to adjust the pulses responsive to the data.

Preferably, application of the non-excitatory stimulation pulse engenders an increase in the cardiac output or, alternatively, a decrease in the cardiac output. Additionally or alternatively, application of the non-excitatory stimulation pulse increases an efficiency of cardiac contraction.

There is further provided, in accordance with a preferred embodiment of the present invention, a method for heart pacing with modification of cardiac contraction, including:

applying one or more electrodes to a subject's heart;

conveying an excitatory electrical pulse to at least one of the one or more electrodes to pace the heart; and conveying a non-excitatory stimulation pulse to at least one of the one or more electrodes to modify an efficacy of cardiac contraction.

Preferably, conveying the non-excitatory stimulation pulse includes synchronizing the pulse with the excitatory pacing pulse, preferably by controlling a time offset of the pulse relative to the pacing pulse.

In a preferred embodiment of the invention, conveying the excitatory and non-excitatory pulses includes conveying the pulses to a common one of the one or more electrodes.

Preferably, applying the one or more electrodes includes implanting a pacing electrodes in a first chamber of the heart and implanting a non-excitatory stimulation electrode in another chamber.

Alternatively or additionally, applying the one or more electrodes includes implanting a plurality of electrodes in a single chamber of the heart, and/or implanting at least one non-excitatory stimulation electrodes in each of a plurality of chambers of the heart.

Further alternatively or additionally, applying the one or more electrodes includes fixing an electrode to the epicardium.

In a preferred embodiment of the invention, the method includes applying at least one sensor to the subject's body, which senses cardiac activity, and conveying the non-excitatory stimulation pulse includes generating a pulse responsive to the activity.

Preferably, applying the at least one sensor includes implanting at least one sensing electrode in the heart. Further preferably, generating the pulse includes detecting a QT interval in an electrical signal received by the sensing electrode and generating a pulse responsive thereto. Preferably, the method includes interrupting the conveyance of the excitatory pulse while conveying the non-excitatory pulse responsive to the activity.

Additionally or alternatively, applying the at least one sensor includes applying a body surface electrode to the subject.

Further additionally or alternatively, applying the at least one sensor includes applying a flow sensor and/or a pressure sensor and/or an oxygen sensor and/or a temperature sensor.

In a preferred embodiment of the invention, generating the pulse includes receiving signals from the sensor via telemetry, and varying a parameter of the pulse responsive thereto.

Preferably, applying the electrodes includes applying electrodes so as to convey the non-excitatory pulse to a segment of the heart having an area of at least 5 mm$^2$, more preferably at least 1 cm$^2$, and most preferably at least 4 cm$^2$.

In a preferred embodiment of the invention, conveying the non-excitatory pulse includes varying an area of the heart to which non-excitatory pulses are applied.

Preferably, conveying the non-excitatory pulse includes varying one or more parameters of the pulse from the group of parameters including voltage, current, duration, timing delay, waveform and waveform frequency.

Further preferably, after conveying the non-excitatory pulse to the at least one of the one or more electrodes, another pulse of opposite polarity thereto is conveyed to the electrodes.

Preferably, modifying the efficacy includes increasing the cardiac output, or alternatively, decreasing the cardiac output. Additionally or alternatively, modifying the efficacy includes enhancing the efficiency of cardiac contraction.

The present invention will be more filly understood from the following detailed description of the preferred embodiments thereof, taken together with the drawings in which:

DETAILED DESCRIPTION OF PREFERRED EMBODIMENTS

Figure 1:
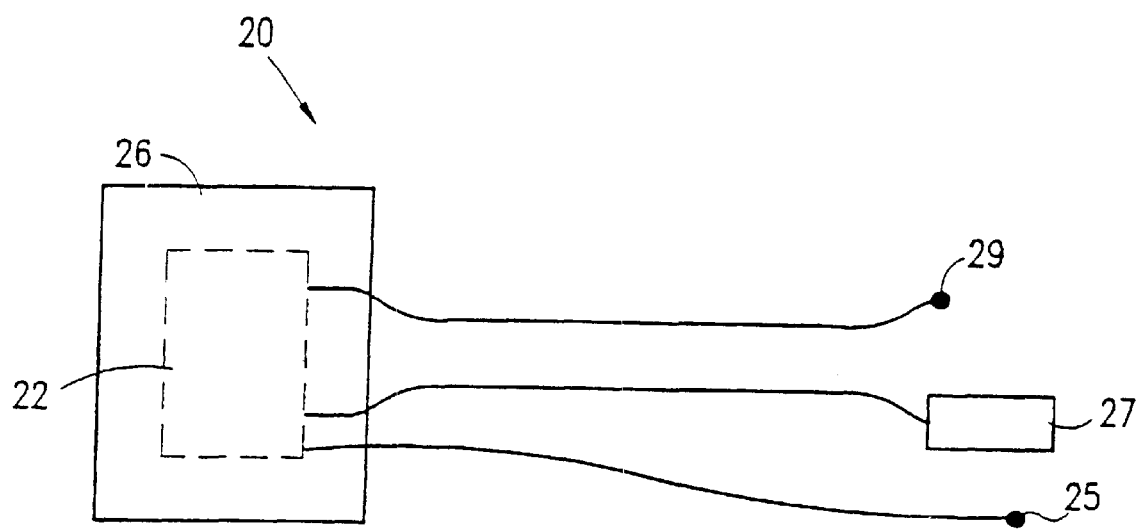
FIG. 1 is a schematic illustration showing a cardiac output enhanced pacemaker (COEP) device, in accordance with a preferred embodiment of the present invention.

FIG. 1 is a schematic illustration of a COEP device 20, for enhancing cardiac output in a paced patient, comprising a control unit case 26, a pacing electrode 29, and a non-excitatory stimulation electrode 27. Electrode 27 preferably comprises a large-area conductive electrode, for example, a pyro-carbon or vitreous carbon electrode, having an area of at least 5 mm$^2$, as described in the above-mentioned "Cardiac Output Controller" patent application, but may alternatively comprise any type of implantable electrode suitable for this purpose. Pacing electrode 29 may comprise any suitable type of pacing electrode known in the art.

Preferably, electrodes 27 and 29 are coated with an anticoagulant, preferably in a time-release form, or elute the anticoagulant into the heart tissue, to prevent clot formation on and around the electrodes. Such electrodes may be produced in a manner similar to steroid-eluting electrodes known in the art, for example, the Medtronic CAPSURE model 4003 electrode, described in *The Foundations of Cardiac Pacing,* by Sutton and Bourgeois, p. 73, which is incorporated herein by reference.

Control unit case 26, which is implanted in the patient's chest, similar to implantable pacemaker controllers known in the art, contains signal veneration circuitry 22 (illustrated in FIG. 3 below and described with reference thereto). Circuitry 22 drives non-excitatory stimulation electrode 27 to apply a non-excitatory stimulation pulse to cardiac muscle tissue. The pulse is initiated by a trigger impulse venerated by the circuitry, preferably in response to and in synchronization with a pacing pulse applied by pacing electrode 29 to the subject's heart.

It will be understood that although device 20 is shown in the figure as comprising only one pacing electrode 29 and one non-excitatory stimulation electrode 27, in other preferred embodiments, COEP devices may comprise multiple pacing and stimulation electrodes, of various types and sizes. Furthermore, in still other preferred embodiments, a single electrode may be used for both pacing and non-excitatory stimulation.

In the embodiment shown in FIG. 1, device 20 also includes an optional sensing electrode 25, which receives local electrogram signals from the heart tissue. Alternatively, one or more of electrodes 27 and 29 may also serve as sensing, electrodes for this purpose. The electrogram is received by signal generation circuitry 22, which regulates the non-excitatory stimulation responsive thereto.

Figure 2A:
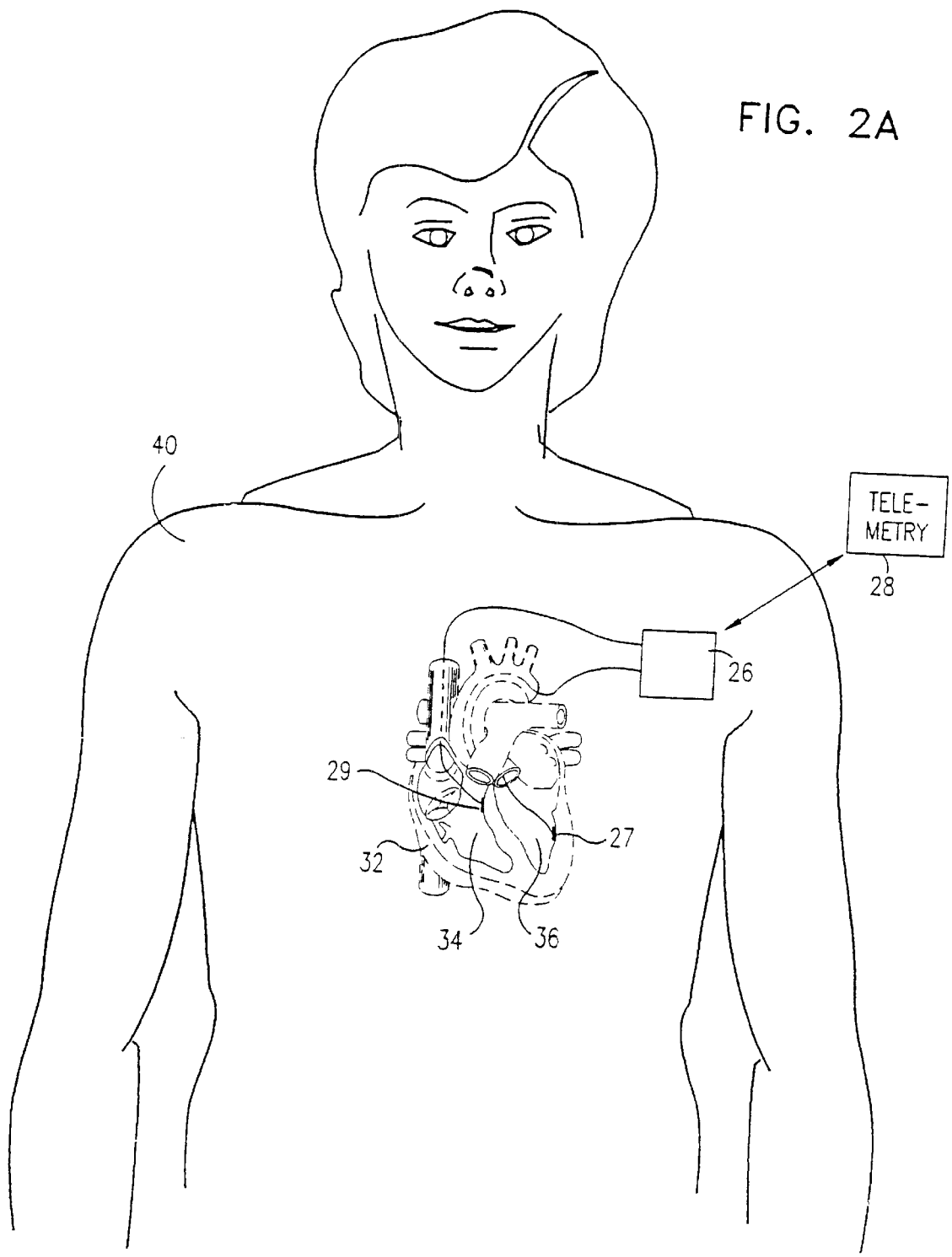
FIG. 2A is a schematic illustration showing implantation of the device of FIG. 1 within a patient's heart and chest, in accordance with a preferred embodiment of the present invention.

FIG. 2A is a schematic illustration showing electrodes 27 and 29 implanted in-heart 32 of a patient 40, in accordance with a preferred embodiment of the present invention. Optional sensing electrode 25 is omitted from this figure. Pacing electrode 29 is preferably implanted on the septum in right ventricle 34, whereas non-excitatory stimulation electrode 27 is implanted in the wall of left ventricle 36. Electrodes 27 and 29 are connected by wires passing through appropriate blood vessels to implantable case 26, which is preferably implanted in the patient's chest. After application of a pacing pulse by electrode 29, COEP device 20 generates a stimulation pulse, which is applied to electrode 27, preferably so as to increase the contraction of at least the segment of the wall of ventricle 36 with which electrode 27 is in contact, thus increasing the ventricular stroke volume.

The embodiment of FIG. 2A also includes an optional telemetry unit 28, in communication with circuitry 22 in case 26. Preferably, circuitry 22 includes an electronic memory, as is known in the art, which receives and stores values of electrophysiological parameters related to the functioning of device 20. Telemetry unit 28 reads and analyzes these parameters, and reprograms circuitry 22 responsive thereto, so as to optimize the functioning of the COEP device.

Figure 2B:
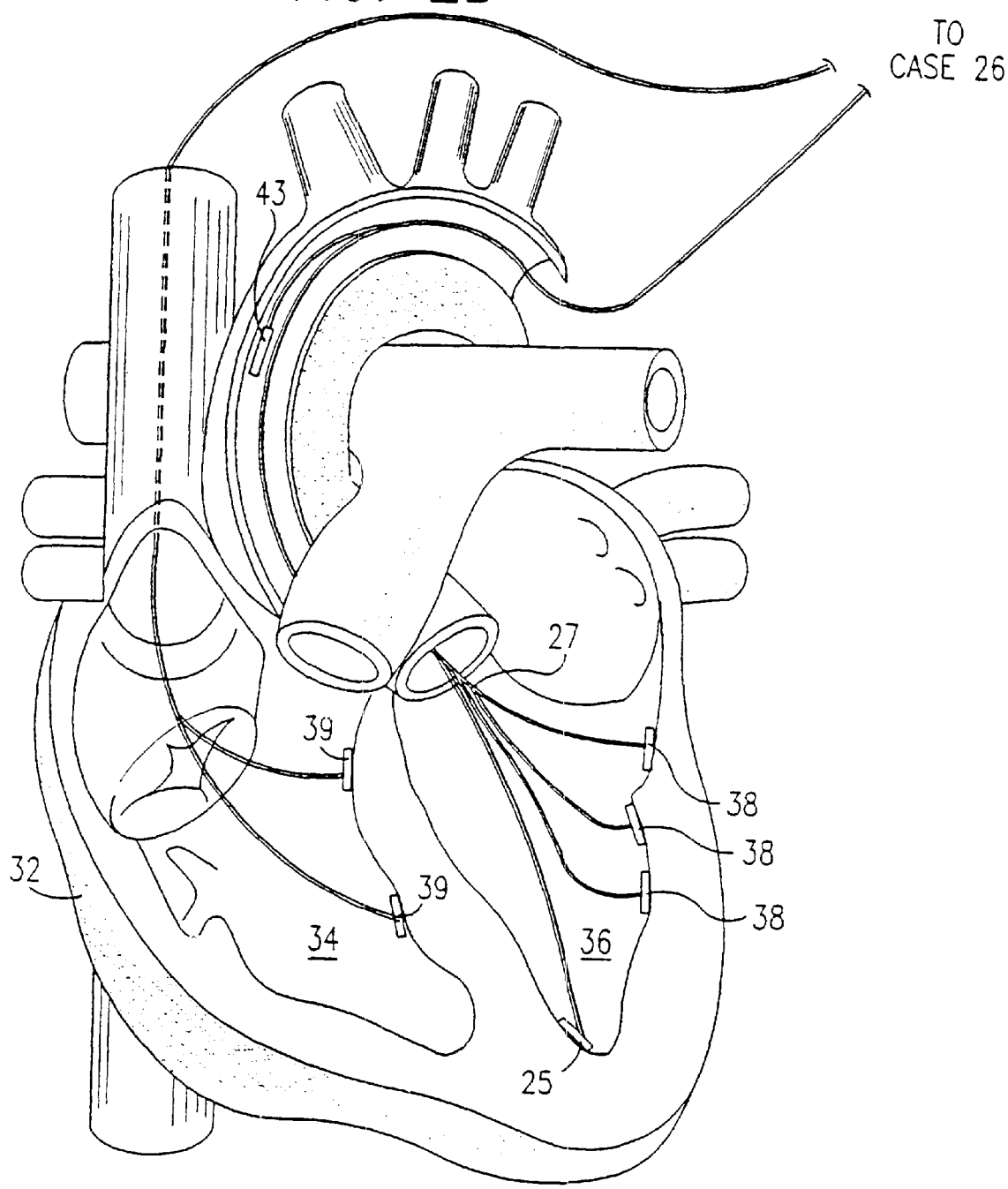
FIG. 2B is a schematic, sectional illustration of the heart, into which pacing and non-excitatory stimulation electrodes are inserted, in accordance with an alternative embodiment of the present invention.

FIG. 2B is a schematic, sectional illustration showing heart 32, in which additional electrodes have been implanted, in accordance with an alternative preferred embodiment of the present invention. In this embodiment, a plurality of non-excitatory stimulation electrodes 38 are implanted in left ventricle 36, so as to stimulate an extended area of the ventricular wall. Preferably, these electrodes form an addressable net, so that the extent of the area of the wall that is stimulated may be varied or modulated, and/or so that the relative timing of stimulation pulses applied to different ones of the plurality of electrodes may be varied. Electrode nets and modulation of the stimulated area and the timing of stimulation pulses are described further in the above-mentioned "Cardiac Output Controller" PCT patent application, incorporated herein by reference. The area and timing are preferably adjusted to give an optimal enhancement of cardiac output.

The embodiment shown in FIG. 2B also includes multiple pacing electrodes 39 in right ventricle 34, and sensing electrode 25 at the apex of left ventricle 36. A further physiological sensor 43, for example, a flow sensor or pressure sensor, is placed in the aorta. Signals from sensor 43 are likewise conveyed to circuitry 22 in case 26, for use in assessing ventricular contraction, so that the stimulation applied by electrodes 38 may be adjusted to give a desired enhancement of cardiac output. For example, the intensity, duration, area extent and/or delay (relative to pacing pulses applied to electrodes 39) of the non-excitatory stimulation pulses applied by tile electrodes may be varied until the desired enhancement is achieved. It will be understood that electrode 25 and sensor 43 may both be placed in other locations in the heart, as well, besides those shown in FIG. 2B.

Figure 2C:
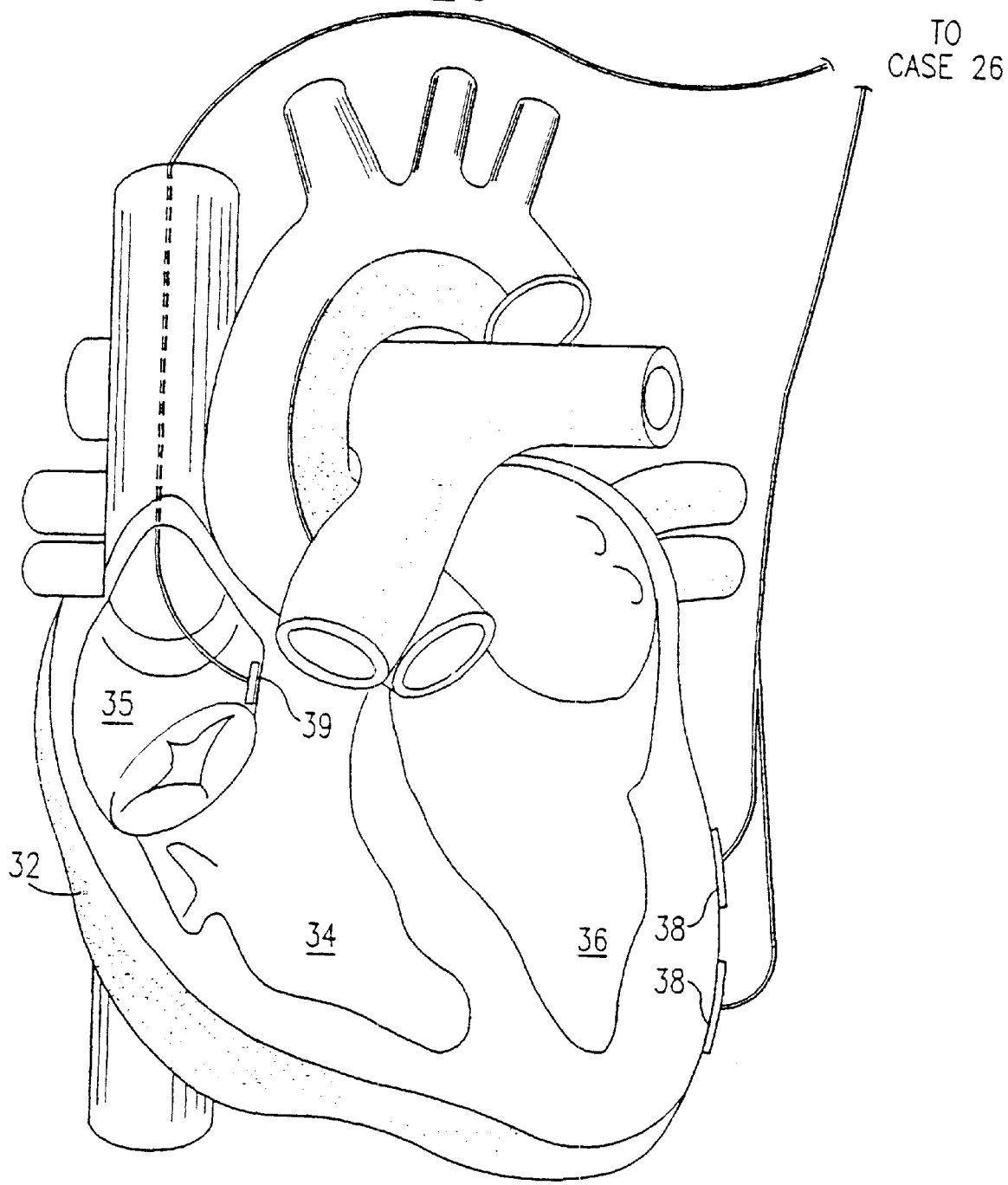
FIG. 2C is a schematic, sectional illustration of the heart, to which pacing and non-excitatory stimulation electrodes are applied, in accordance with still another alternative embodiment of the present invention.

FIG. 2C is a schematic, sectional illustration of heart 32, to which electrodes have been fixed in accordance with still another preferred embodiment of the present invention. In this case pacing electrode 39 is implanted in right atrium 35. Non-excitatory stimulation electrodes 38 are implanted surgically on the epicardium of left ventricle 36.

Although FIGS. 2A–2C show certain specific placements of the pacing and non-excitatory stimulation electrodes, it will be understood that other electrode placements are also possible. For example, particularly in cases of severe cardiac insufficiency, non-excitatory stimulation electrodes may also be placed in or on an epicardial surface of the right ventricle, and/or of one or both atria, preferably using a thorascope or other minimally-invasive surgical method. Similarly, pacing electrodes may be placed in two, three or all four chambers of the heart, in accordance with methods of multi-chamber pacing known in the art. Additionally or alternatively, at least some of the pacing and non-excitatory stimulation electrodes may be "floating electrodes," as are known in the art, which are not fixed to tile heart wall and can move within a heart chamber. The optimal electrode placement in each case may be a function of the particular pathological condition of the heart, and may preferably be ascertained by mapping the heart before placement of the electrodes, as described above. The non-excitatory stimulation electrodes may also be inserted and positioned in the heart's blood vessels, as described in the above-mentioned "Cardiac Output Controller" PCT patent application.

Figure 2D:
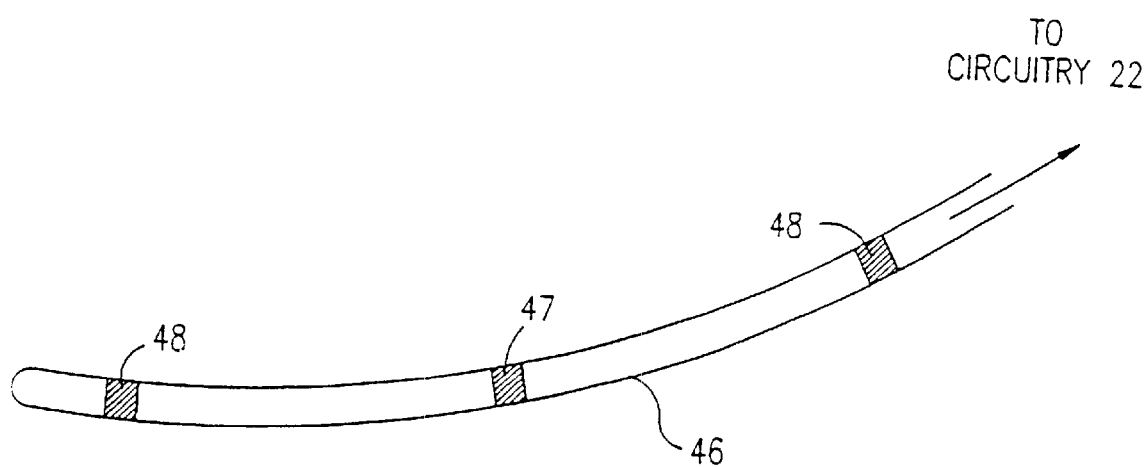
FIG. 2D is a schematic illustration showing an integrated pacing and stimulation electrode unit, in accordance with another preferred embodiment of the present invention.

FIG. 2D is a schematic illustration of a stimulation probe 46, for use in conjunction with COEP device 20, in accordance with an alternative embodiment of the present invention. Probe 46 includes a pacing, electrode 47, preferably unipolar, and two non-excitatory stimulation electrodes 48, between which the non-excitatory pulse is applied. The probe may be implanted in a single chamber of the heart, thereby simplifying the task of electrode placement. Alternatively, because probe 46 is long, narrow and, preferably, flexible, it may be inserted into one of the heart's blood vessels.

Figure 3:
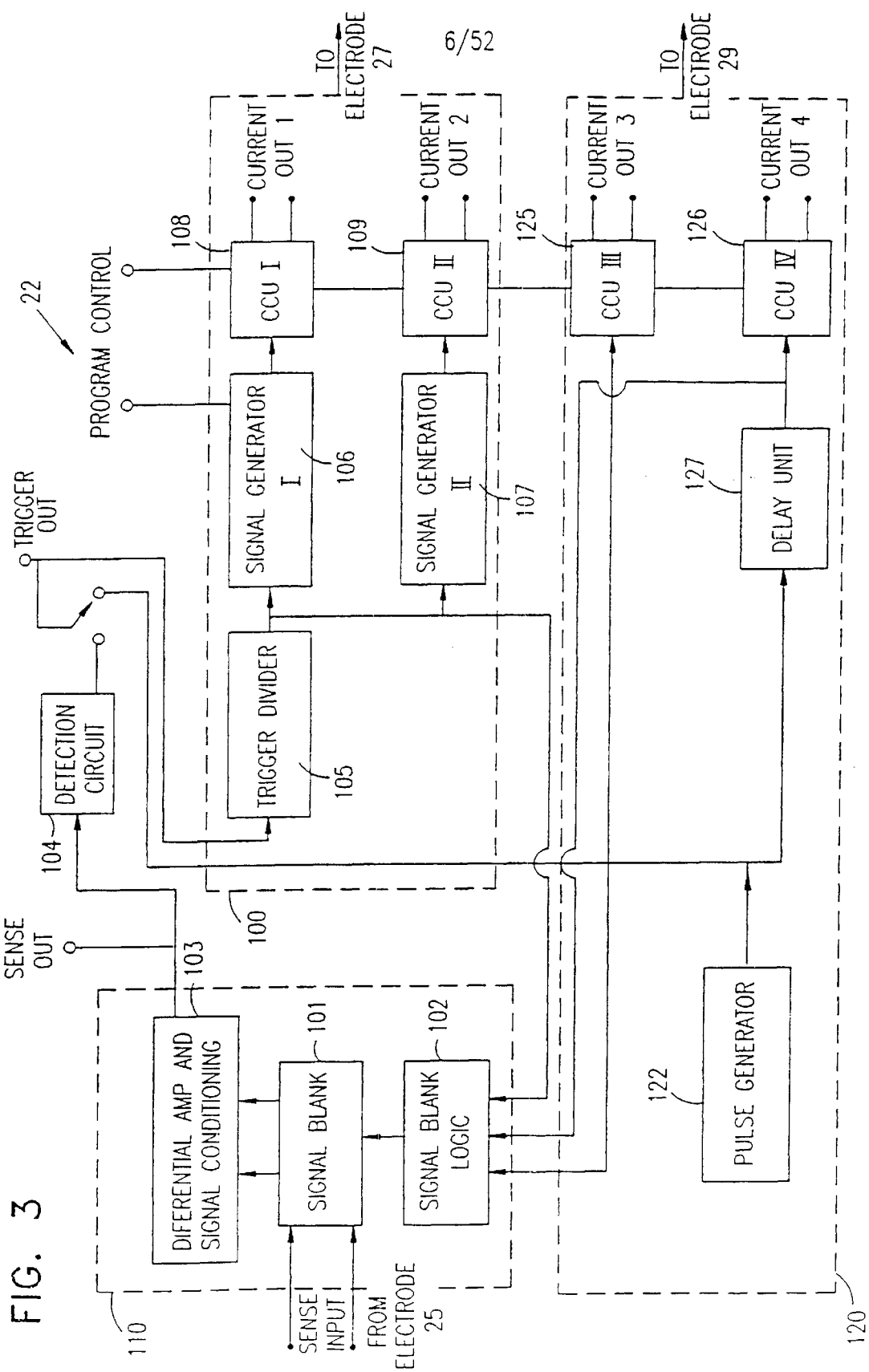
FIG. 3 is a schematic block diagram showing signal generation circuitry used in the device depicted in FIG. 1, in accordance with a preferred embodiment of the present invention.

FIG. 3 is a schematic block diagram showing signal generation circuitry 22, in accordance with a preferred embodiment of the present invention. Circuitry 22 comprises a non-excitatory stimulation section 100 and a pacing section 120, as well as an optional sensing unit 110 and detection circuit 104. Optionally, circuitry 22 also communicates with a telemetry and external programming unit, such as telemetric unit 23, shown in FIG. 2A.

In a standard mode of operation, pacing section 120 and stimulation section 100 are triggered to apply pulses to pacing electrode 29 and stimulation electrode 27, respectively, responsive to a pulse generator 122 in section 120. The pulse generator may be programmed and controlled to pace the heart in substantially any mode of pacing known in the art, for example, DDD, DDDR and VVI modes.

Circuitry 22 may also operate in an adaptive mode, however, responsive to electrogram signals received from sensing electrode 25, or to ECG signals from a body surface electrode. In this mode, unit 110 receives and conditions the electrogram signals. Detection circuit 104 receives the conditioned signals and senses an activation waveform in the electrogram, as is known in the art, and generates a trigger pulse responsive thereto. The trigger pulse is conveyed to stimulation section 100. Pacing, section 120 continues to operate under the control of pulse generator 122, as in the standard mode described above.

Sensing unit 110 includes signal blanking unit 101 and signal blank logic 102 and a differential amplifier/signal conditioning circuit 103. The blanking operates to block the input to detection circuit 104 while the output of pacing section 120 or stimulation section 100 is active, to prevent the system from generating trigger pulses due to stimulation artifacts.

Pacing section 120 includes pulse generator 122 and constant current units (CCU) 125 and 126. The CCU's generate output pacing pulses responsive to the trigger received from pulse generator 122. The output pulses are applied to pacing electrode 29, as well as to one or more optional additional pacing electrodes, as shown, for example, in FIG. 2B. When multiple pacing electrodes are used, a delay unit 127 allows the relative timing of the pacing pulses applied to the electrodes to be controlled and adjusted.

Stimulation section 100 comprises a trigger divider 105, which generates a modified trigger pulse in response to input trigger pulses from pulse generator 122 or from detection circuit 104, or alternatively from external trigger input 30. The trigger divider allows a user of device 20 to select whether the stimulation pulse will be applied at every heart beat or only once in a predetermined number of beats. Section 100 further includes signal generators 106 and 107, which generate voltage signals of predefined characteristics, as described below, in response to the modified trigger pulse, and constant current units (CCU) 108 and 109, which convert input voltage signals from the signal generators to output current pulses. Two stimulation output channels are shown in FIG. 3, enabling different stimulation pulses to be applied to two or more different stimulation electrodes. It will be appreciated, however, that only one of the channels need be used or alternatively, that additional channels may be added to drive additional stimulation electrodes.

Figure 4:
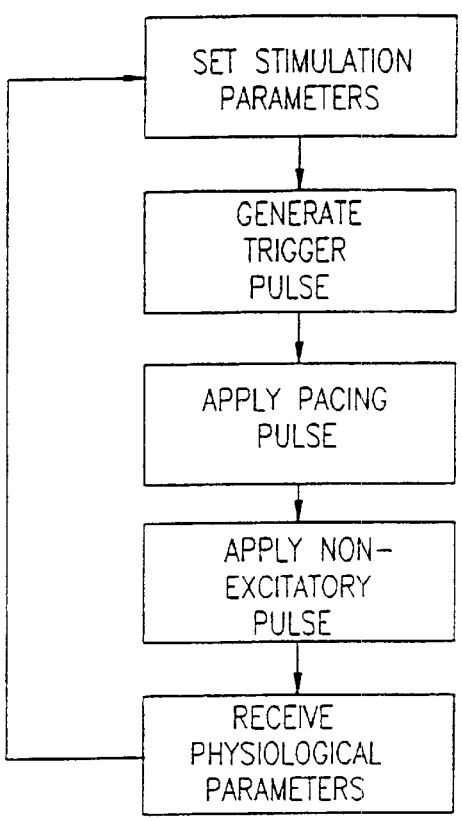
FIG. 4 is a flow chart illustrating a method of artificial pacing with cardiac output enhancement, in accordance with preferred embodiments of the present invention.

FIG. 4 is a flow chart, which illustrates a method for enhancing cardiac output in a paced patient using COEP device 20, according to a preferred embodiment of the present invention. Pacing parameters and non-excitatory stimulation parameters are initially input to fit the patient's condition. The device is set so that stimulation section 100 operates in either the standard, self-triggered mode or the adaptive mode, responsive to electrogram or ECG signals received from the heart. In either case, a trigger pulse is venerated by pulse generator 122 and is applied to CCU 125 (and optionally, after a delay, to CCU 126), which produces a pacing pulse output to electrode 29. A trigger pulse is likewise input to non-excitatory stimulation section 100, whereby CCU 108 and, optionally, CCU 109 generate non-excitatory stimulation pulses having predefined or user-defined characteristics, which are applied to the heart by non-excitatory stimulation electrode 27.

Optionally, electrical or other physiological signals are received from the heart, for example, by electrode 25 and/or sensor 43, as shown in FIG. 2B. These signals are used in adjusting the pacing and/or non-excitatory stimulation parameters to be applied in subsequent cycles. The signals may either be processed and used on-line, within circuitry 22, or they may be transferred to telemetry unit 28, which analyzes the signals and reprograms the circuitry accordingly.

Figure 5:
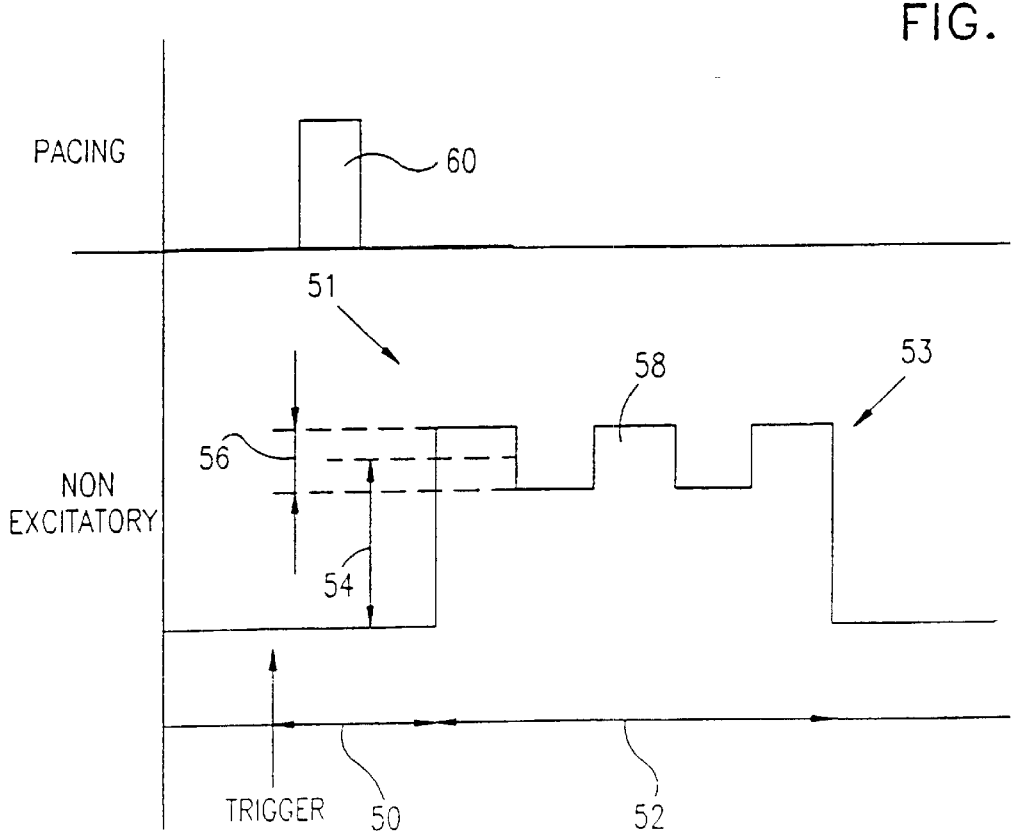
FIG. 5 is a schematic illustration showing pacing and non-excitatory stimulation pulses applied by a COEP device to the patient's heart, in accordance with a preferred embodiment of the present invention.

FIG. 5 is a schematic illustration of pulses applied to heart 32 by device 20, including a pacing pulse 60, applied by pacing electrode 29, and a non-excitatory stimulation pulse 51, applied by stimulation electrode 27, in accordance with a preferred embodiment of the present invention. As shown in the figure, pacing pulse 60 is preferably initiated immediately upon generation of the trigger pulse by pulse generator 122. The amplitude and duration of the pacing pulse are in accordance with principles of cardiac pacing known in the art.

In some preferred embodiments of the present invention the regulation of cardiac output is achieved by varying certain characteristics of pulse 51. Non-excitatory stimulation energy is applied to stimulation electrode 23 in the form of a baseline pulse 53, having a baseline amplitude, indicated by an arrow 54 in FIG. 5, of preferably 0.1 to 10 mA, optionally up to 50 mA, and a duration, indicated by an arrow 52, preferably ranging between 1 and 300 msec, most preferably between 10 and 30 msec. Preferably, signal generators 106 and 107 are controlled to provide a delay, indicated by an arrow 50 in FIG. 5, of between 1 and 500 msec between the trigger input and the onset of pulse 53. Pulse 53 is preferably followed by another pulse of opposite polarity (not shown in the figure) to prevent problems of tissue polarization and electrode degradation, as described in the above-referenced '012 PCT application and mentioned above.

Preferably, a waveform 58 having a frequency of lip to 10 kHz and amplitude, indicated by an arrow 56, up to or comparable to the baseline amplitude is superimposed on the baseline amplitude of pulse 53. Although waveform 58 is shown here as a square wave, any other suitable waveform may be used, for example, a sinusoid or sawtooth wave. The appropriate amplitude, duration, delay, waveform, etc., of non-stimulatory pulse 51 are preferably adjusted to provide a desired increase or, alternatively, a decrease, in the cardiac output.

Non-excitatory stimulation pulse 51 may be applied to heart 32 alone various electrical paths. For example, in one preferred embodiment, described with reference to FIG. 2A, stimulation electrode 27 operates as a unipolar electrode, and pulse 51 is applied between electrode 27 and case 26, which is preferably made of an electrically conductive material. Alternatively, the pulse may be applied between stimulation electrode 27 and pacing electrode 29. Further alternatively, referring now to FIG. 2B, multiple stimulation electrodes 38 may operate in a bipolar mode, whereby pulse 51 is applied between a pail of the electrodes.

Figure 6A:
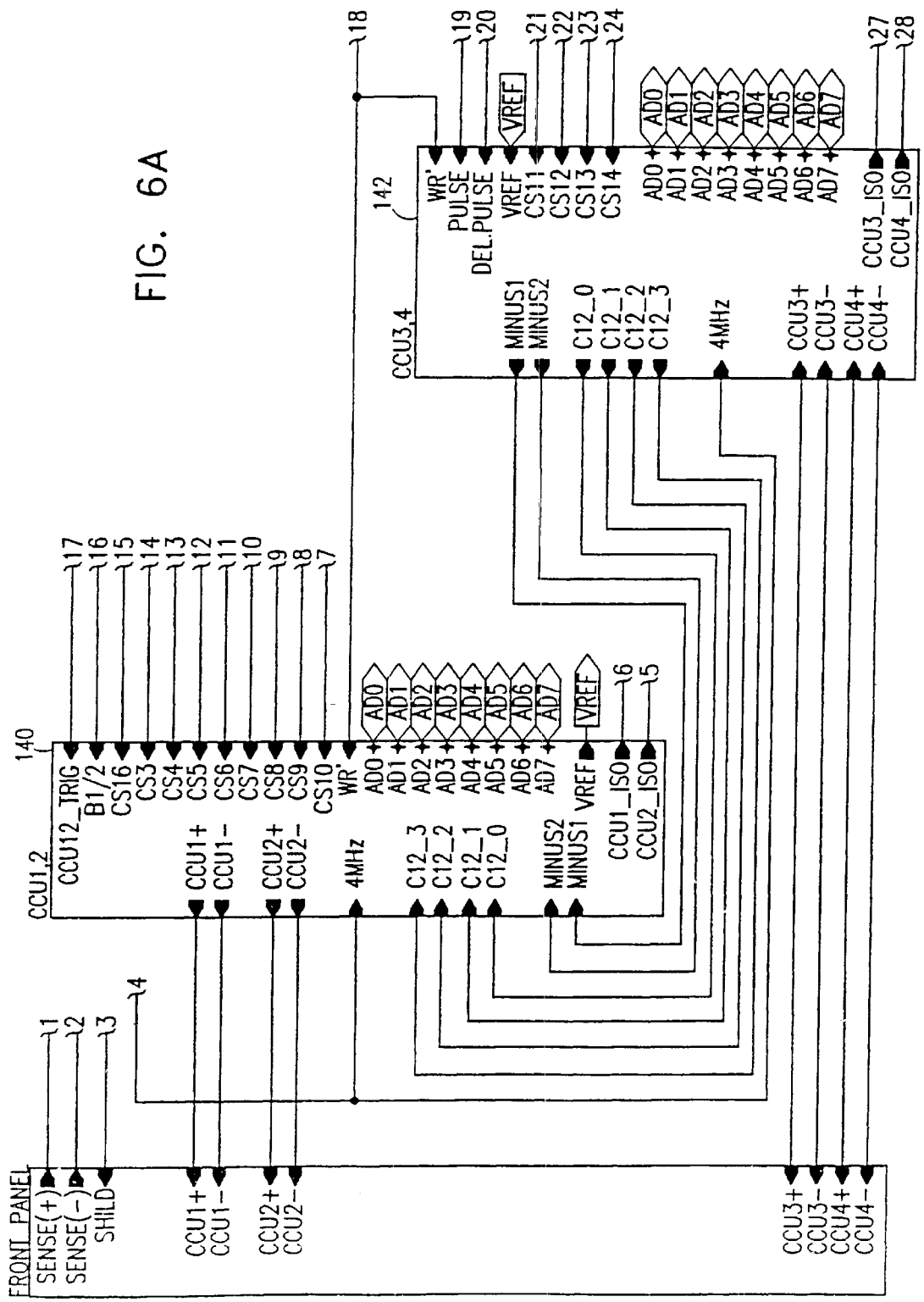
FIGS. 6–30 are electronic schematic diagrams showing circuitry for use in the device of FIG. 1, in accordance with a preferred embodiment of tie present invention.
Figure 6B:
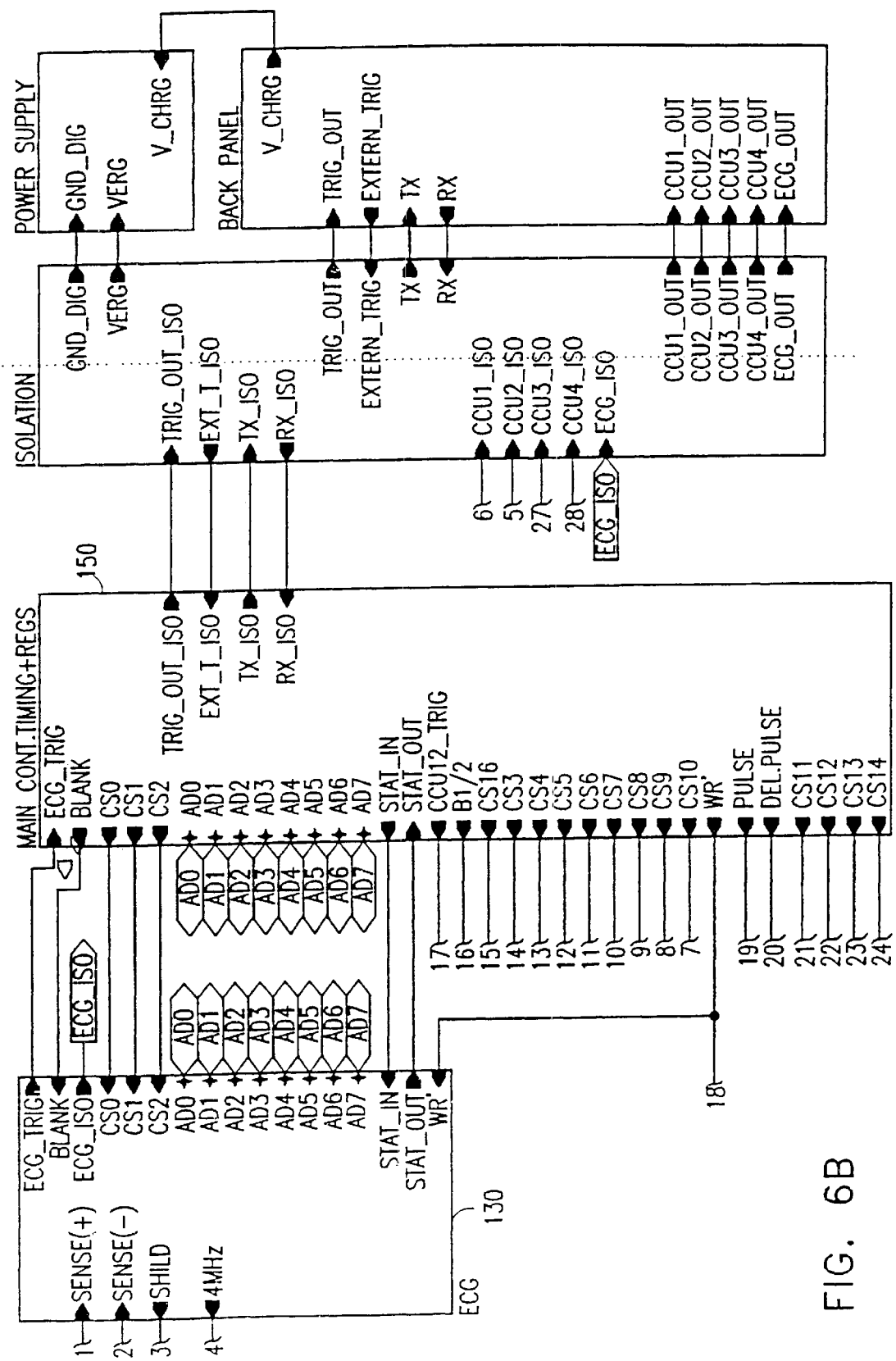

FIGS. 6–29 are electronic schematic diagrams illustrating circuitry for use in implementing the functions of circuitry 22, in accordance with a preferred embodiment of the present invention. As shown in FIGS. 6A and 6B, the circuitry includes an ECG processor 130, a first CCU section 140, a second CCU section 142 and main control circuit 150, which together perform the functions of circuitry 22, as shown in FIG. 3 and described with reference thereto.

FIGS. 7 through 29 are circuit diagrams showing details of the implementation of the elements of FIGS. 6A and 6B. These diagrams are considered sufficient in and of themselves to enable one skilled in the art to practice the present invention. Various aspects of these diagrams are described hereinbelow.

Figure 7A:
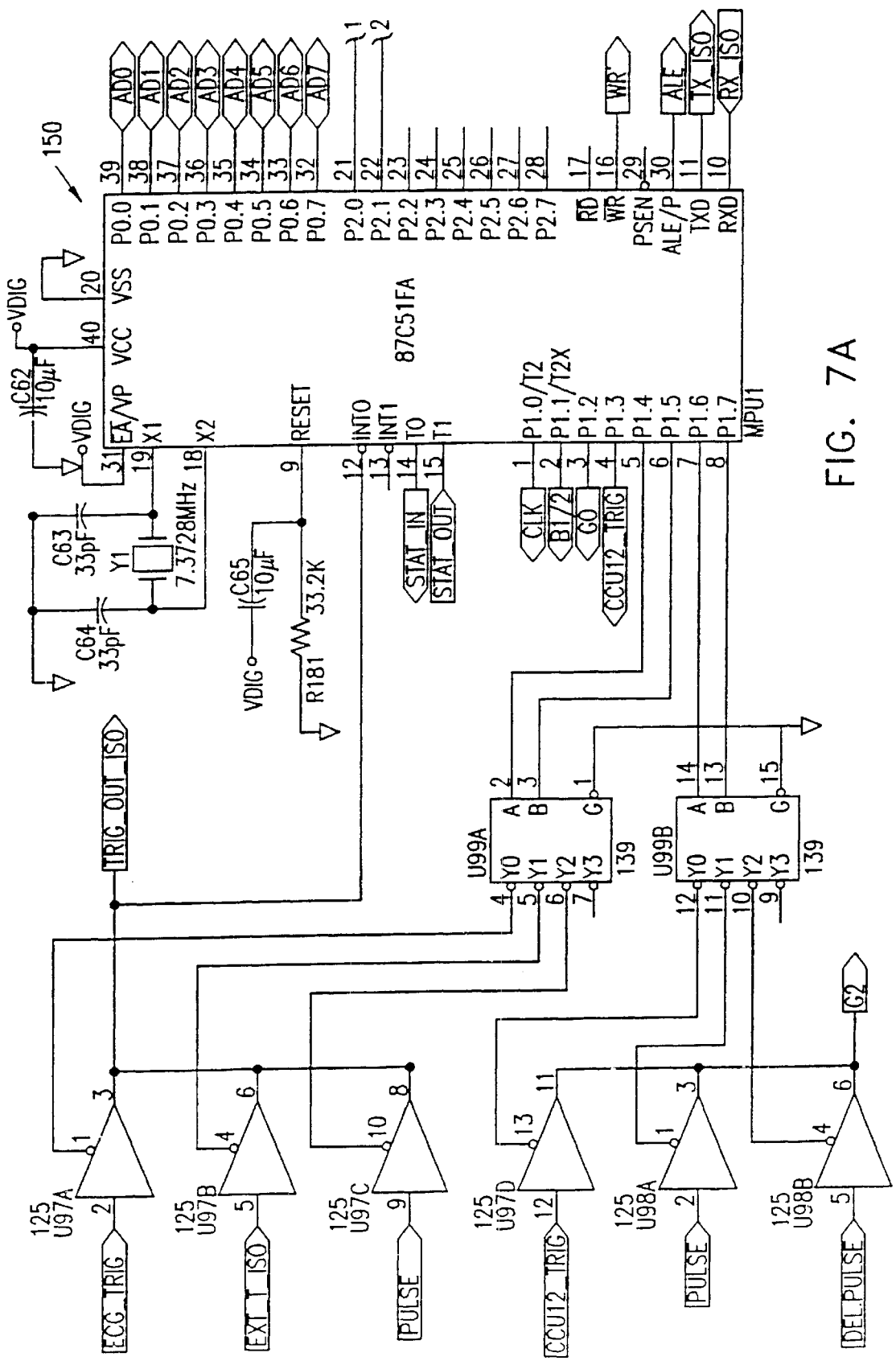
Figure 7B:
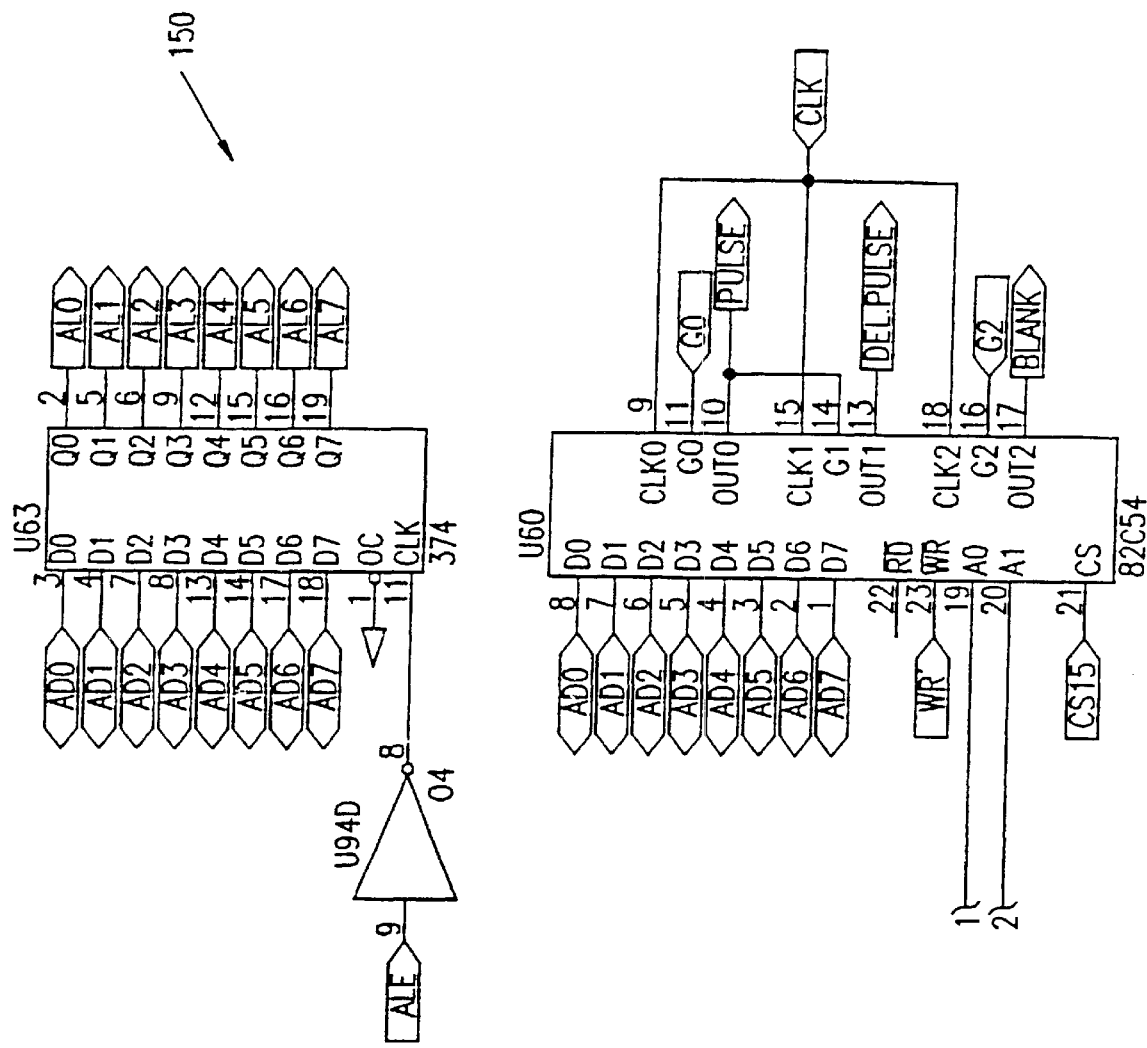
Figure 7C:
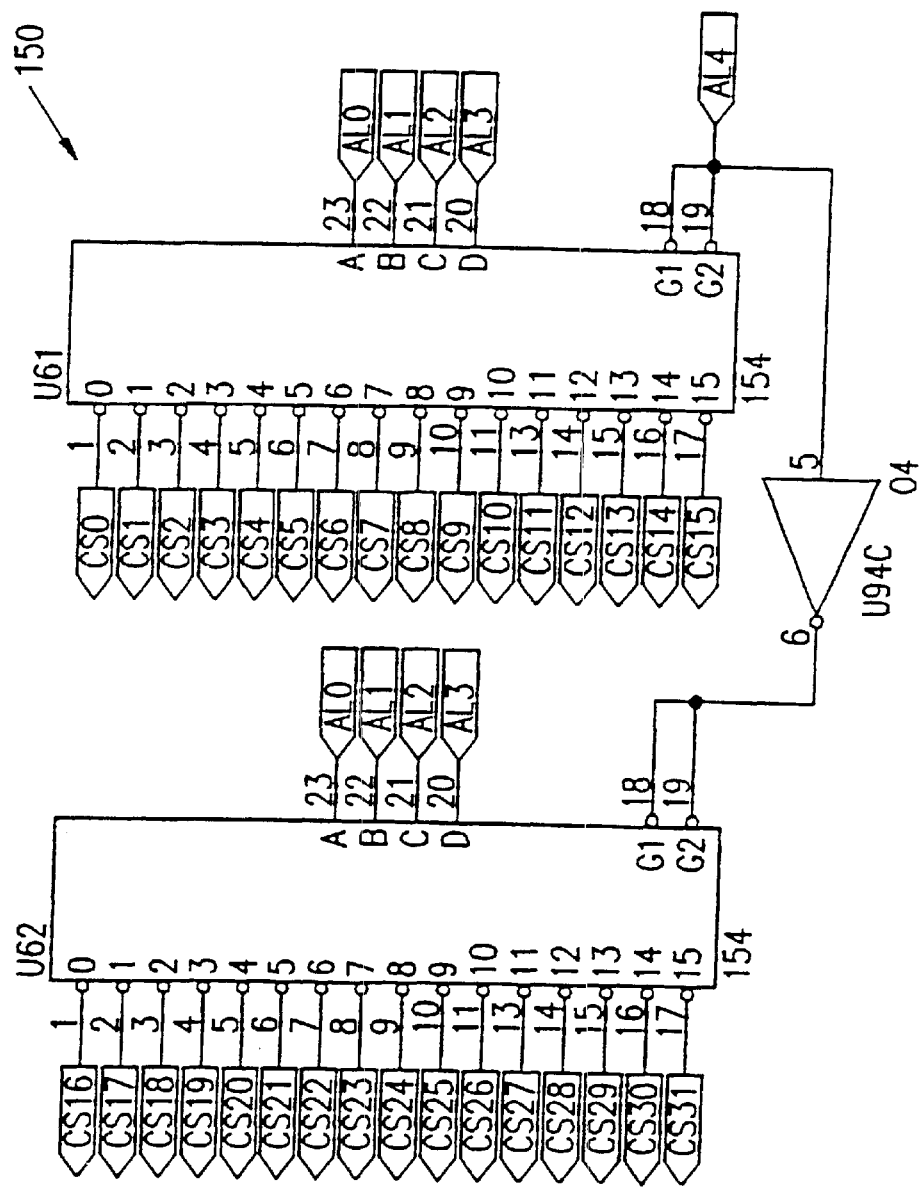

FIGS. 7A, 7B and 7C illustrate main control circuit 150, which is based on a microcontroller MPUI, preferably in 8051-type microcontroller, as is known in the art. The microcontroller receives user commands via a communications interface, for example, to program parameters of the stimulation pulses to be applied. It controls other elements of circuitry 22 via a data bus, marked AD0–AD7.

Figure 8A:
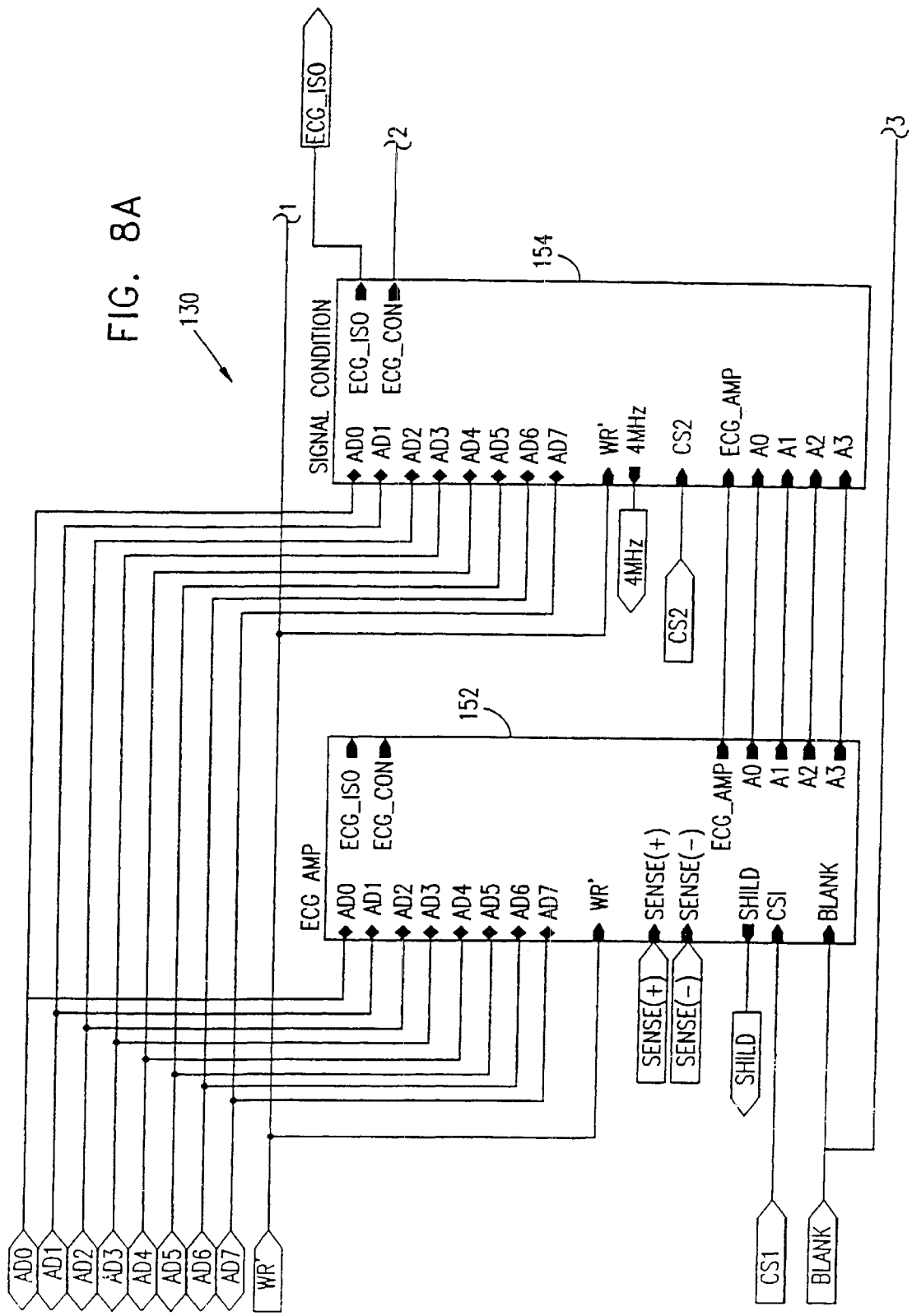
Figure 8B:
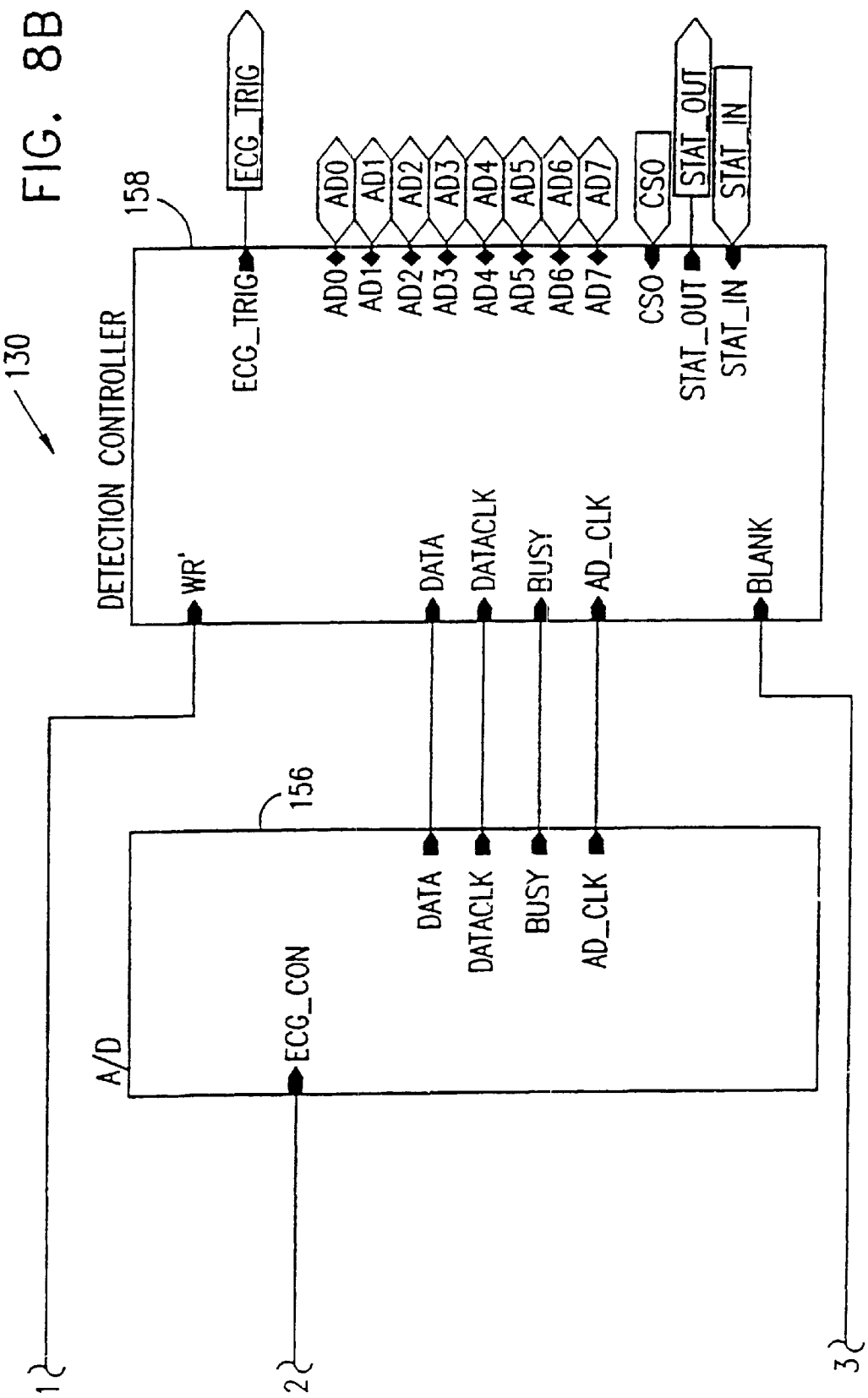
Figure 9:
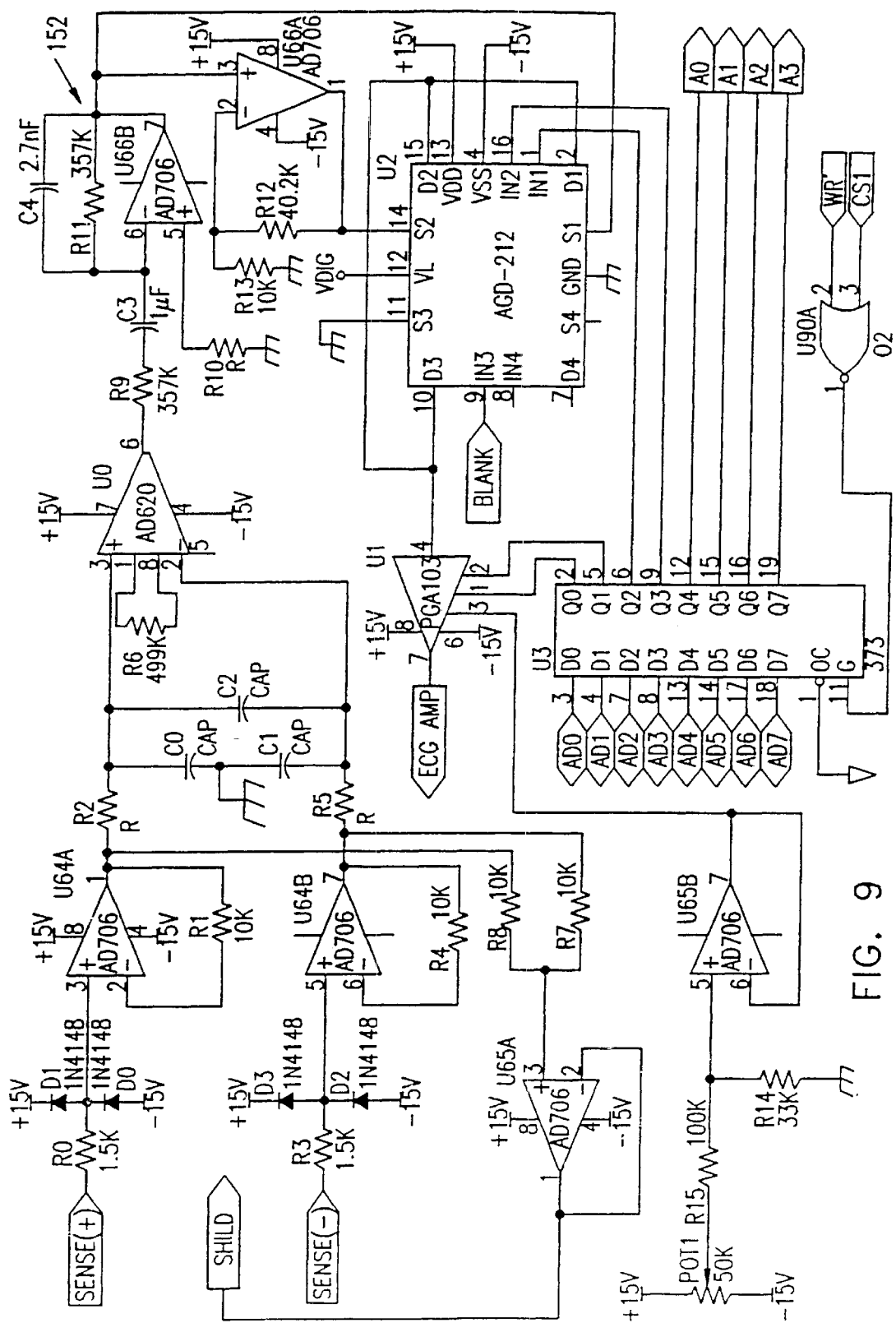
Figure 10A:
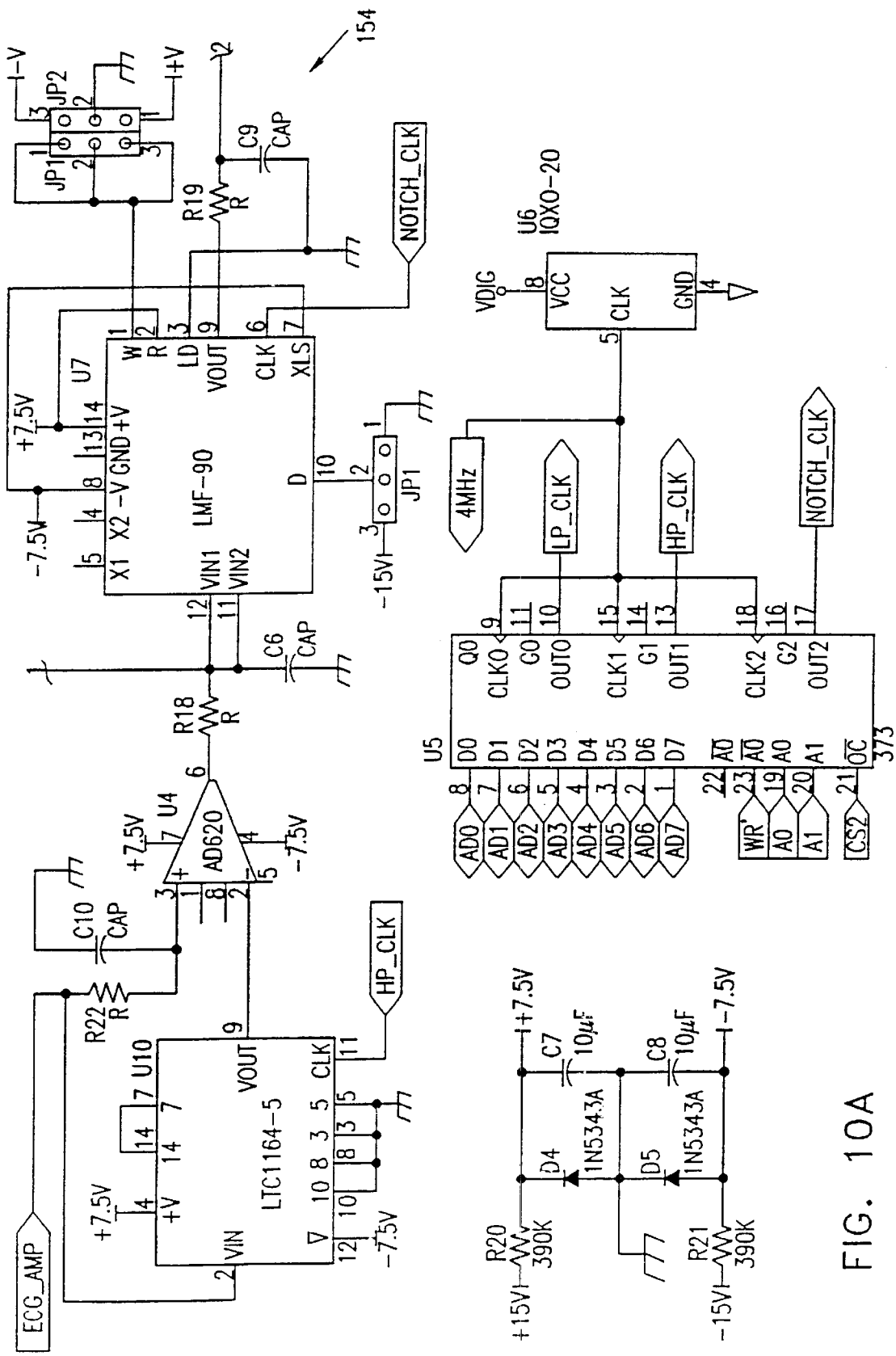
Figure 10B:
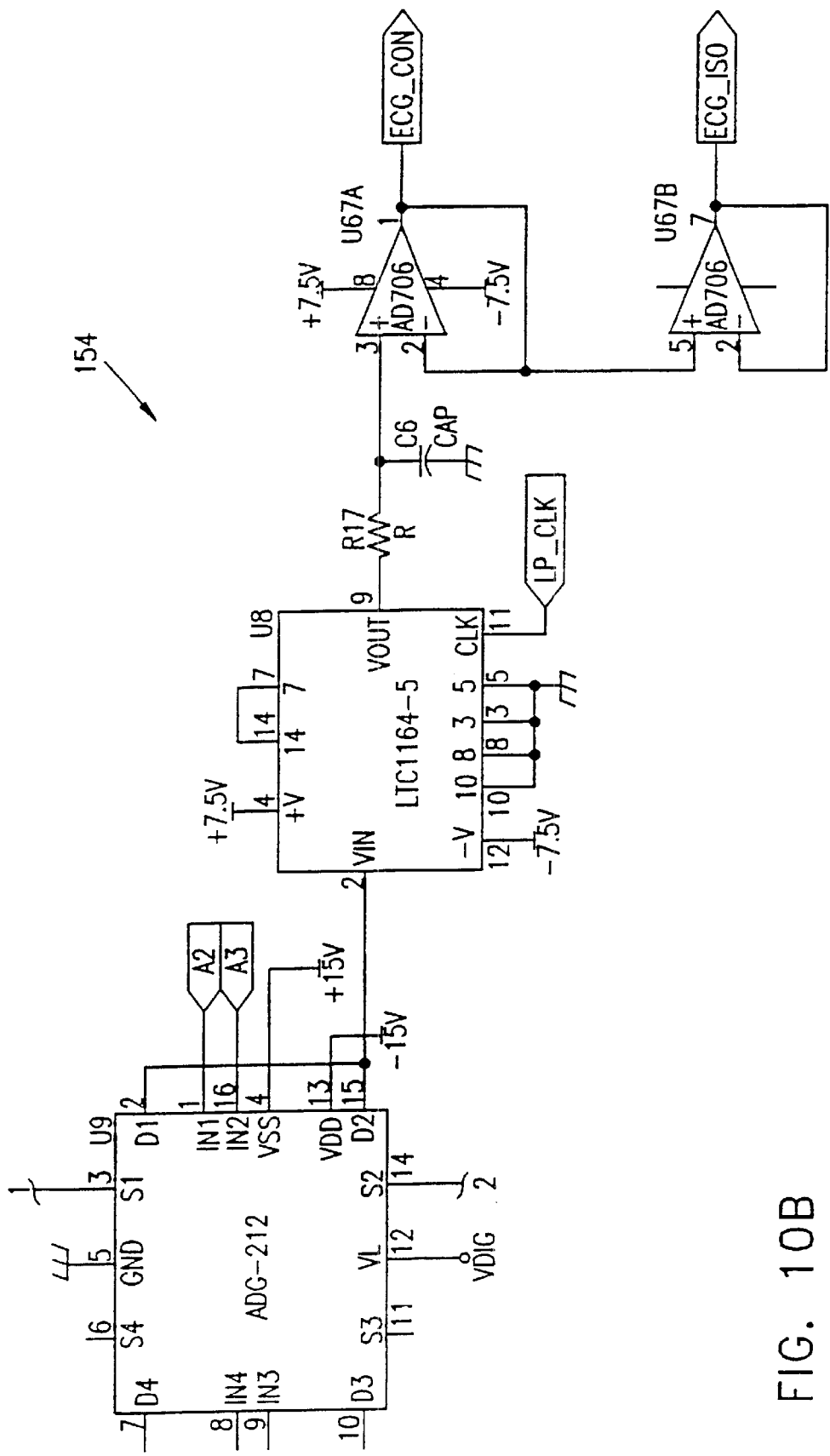
Figure 11:
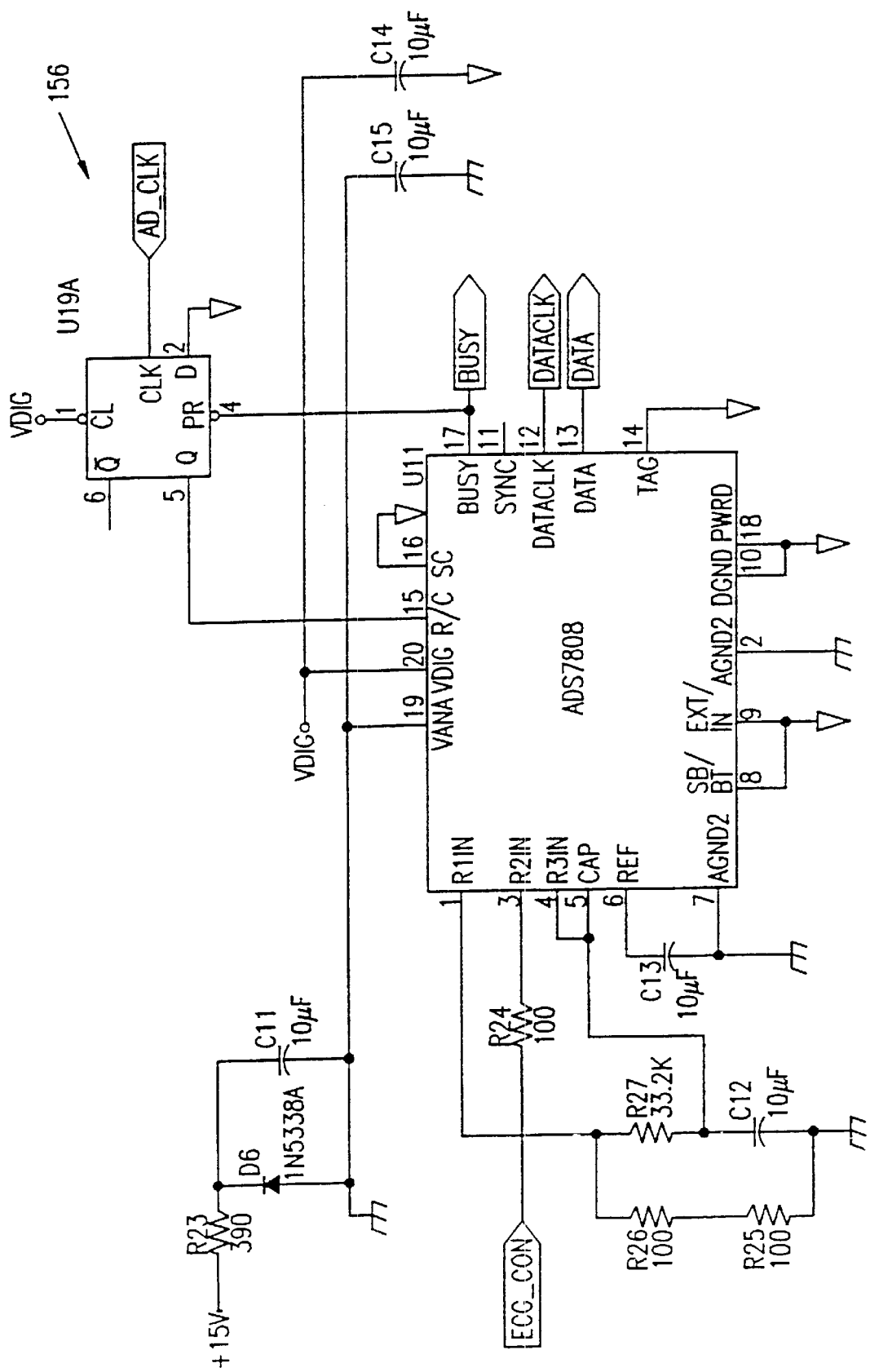
Figure 12A:
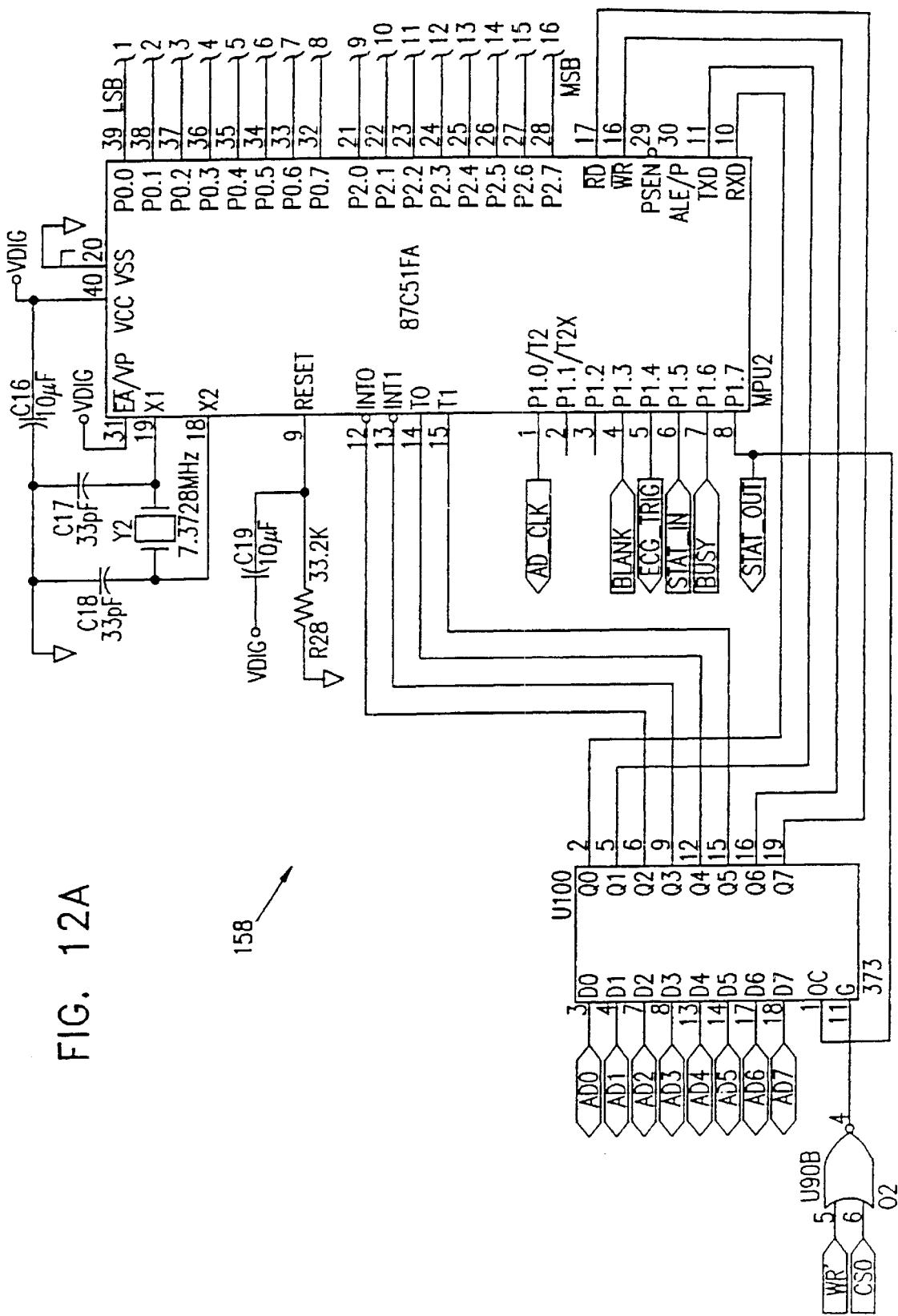
Figure 12B:
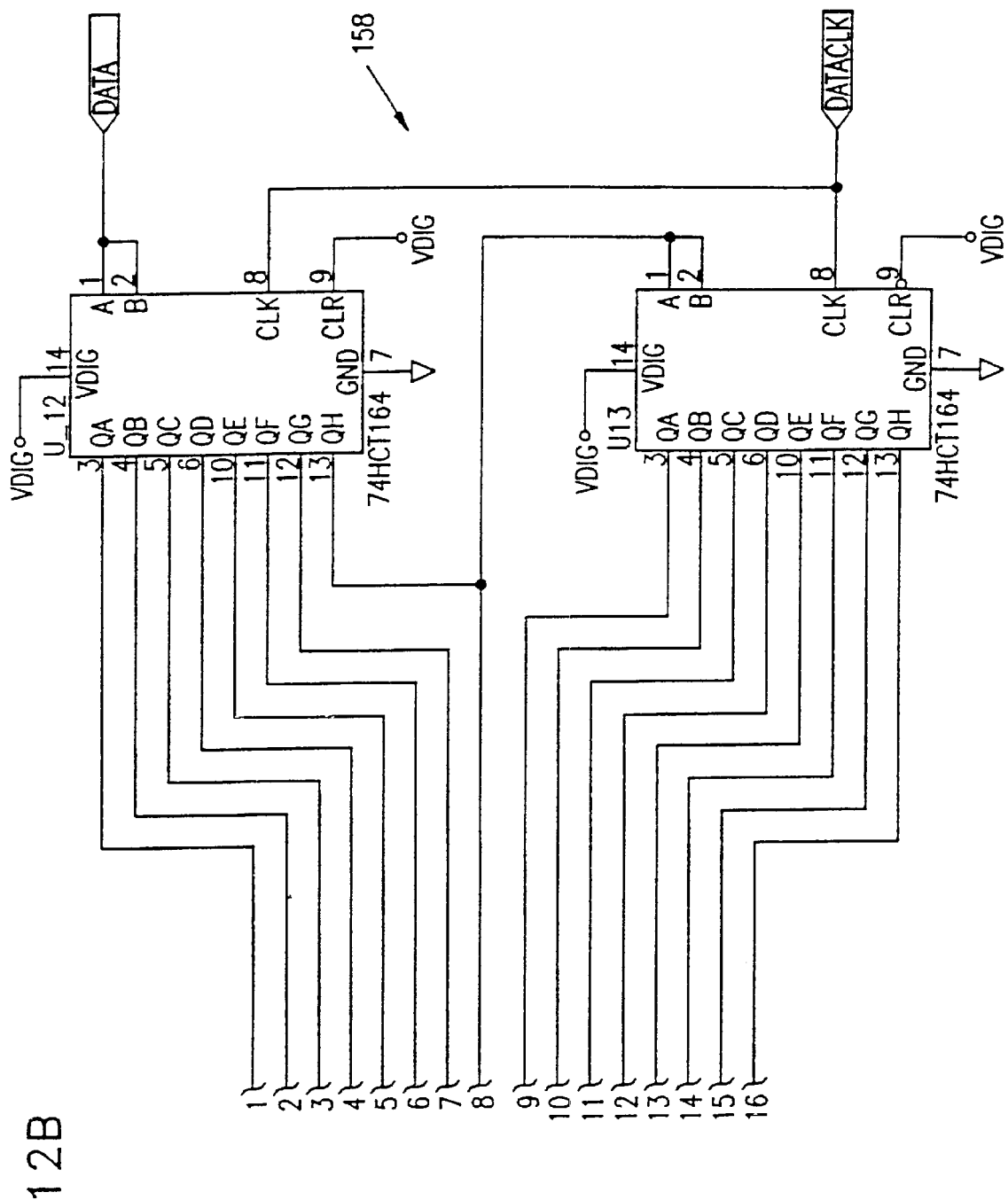

FIGS. 8A and 8B show details of ECG processor 130, which receives electrical signals from the patient's body and processes them to generate trigger pulses, as described above, for driving the non-excitatory stimulation. ECG processor 130 includes an ECG amplifier 152, an ECG signal conditioning unit 154, an A/D converter 156, and a detection controller 158. ECG amplifier 152 is shown in detail in FIG. 9, and comprises a differential preamplifier and programmable gain amplifier and blanking unit. Signal conditioning unit 154, shown in FIGS. 10A and 10B, includes programmable high-pass, low-pass and notch filters, selectable by means of a clock generator, and also including an analog switch for bypassing the notch filter. A/D converter 156 is shown in FIG. 11. FIGS. 12A and 12B illustrate controller 158, including another 8051-type microcontroller MPU2, which analyzes the ECG signal and generates the trigger pulse.

Figure 13A:
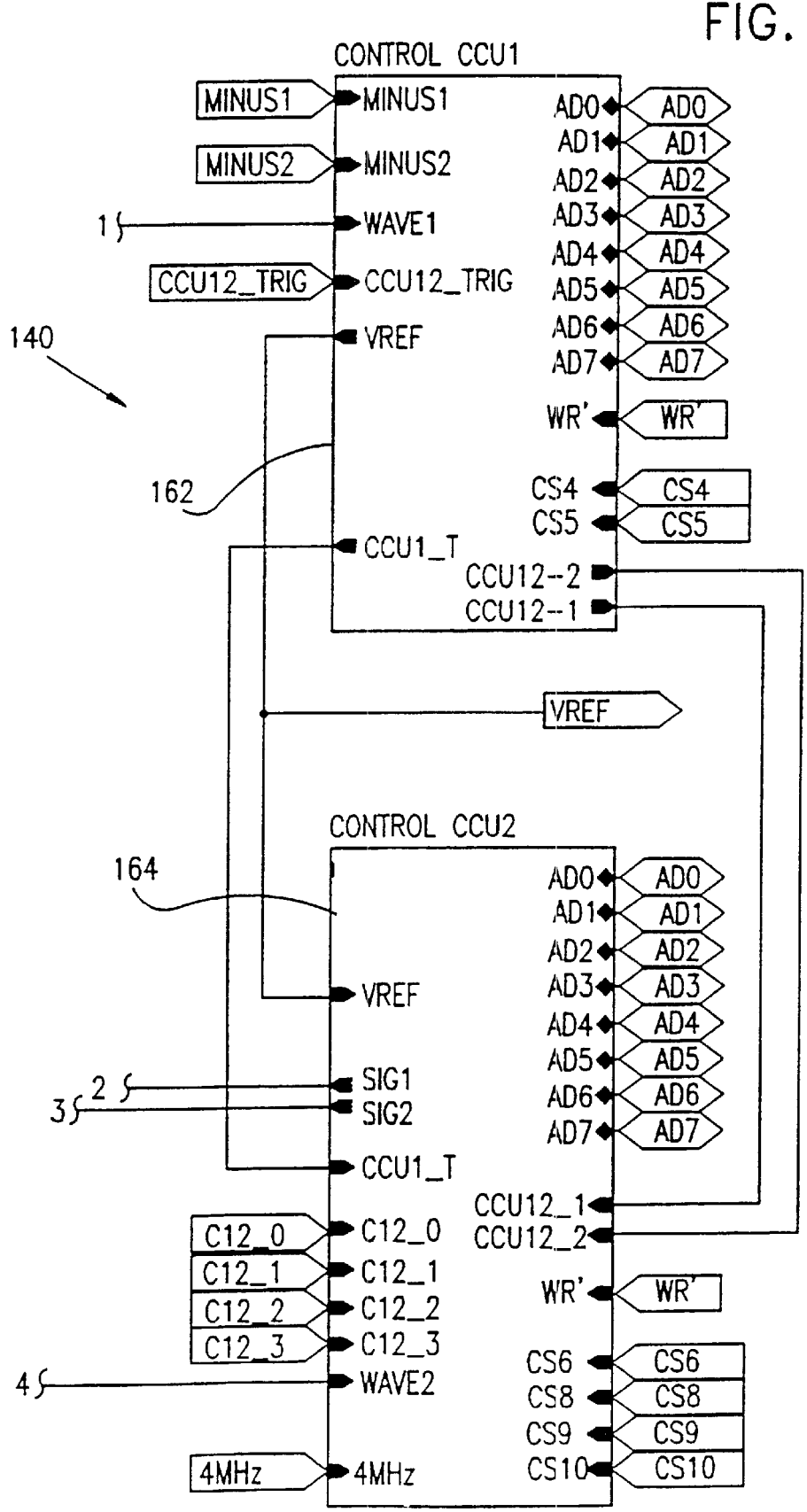
Figure 13B:
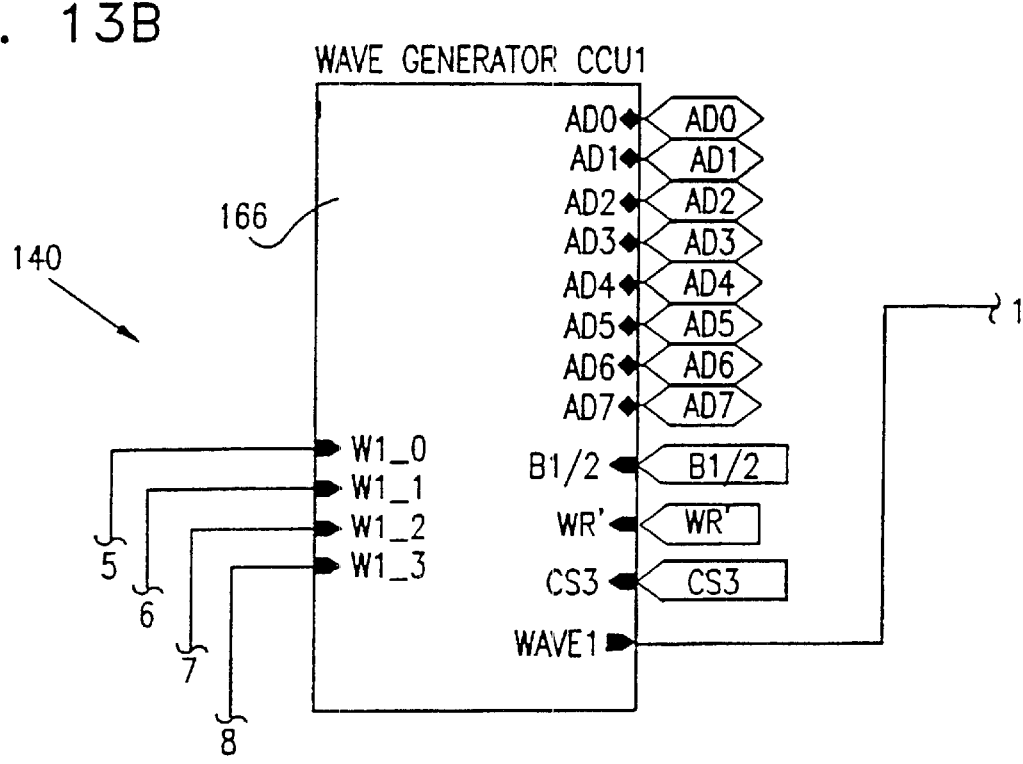
Figure 13B:
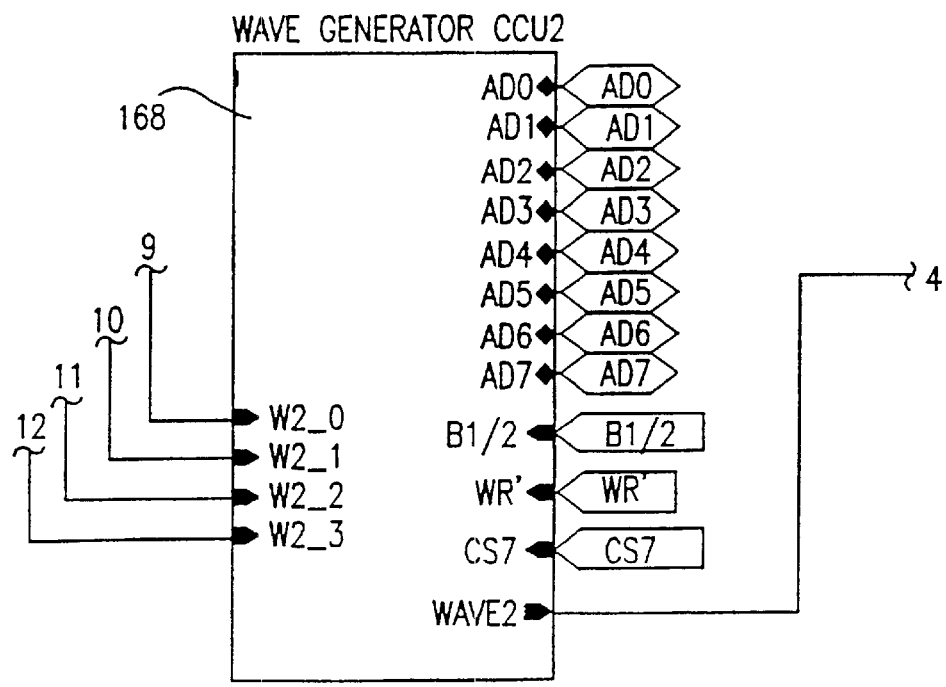
Figure 13C:
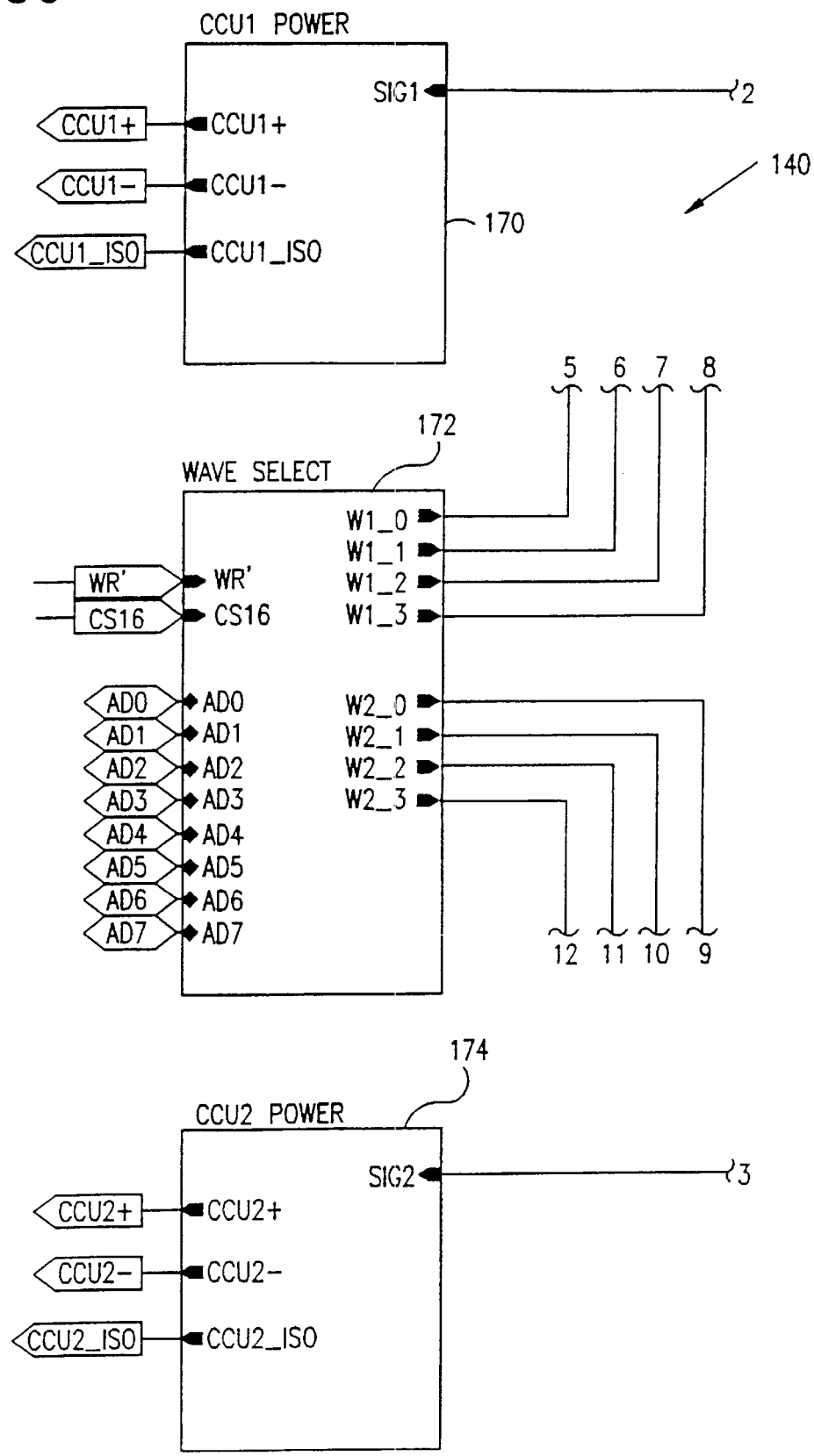
Figure 14A:
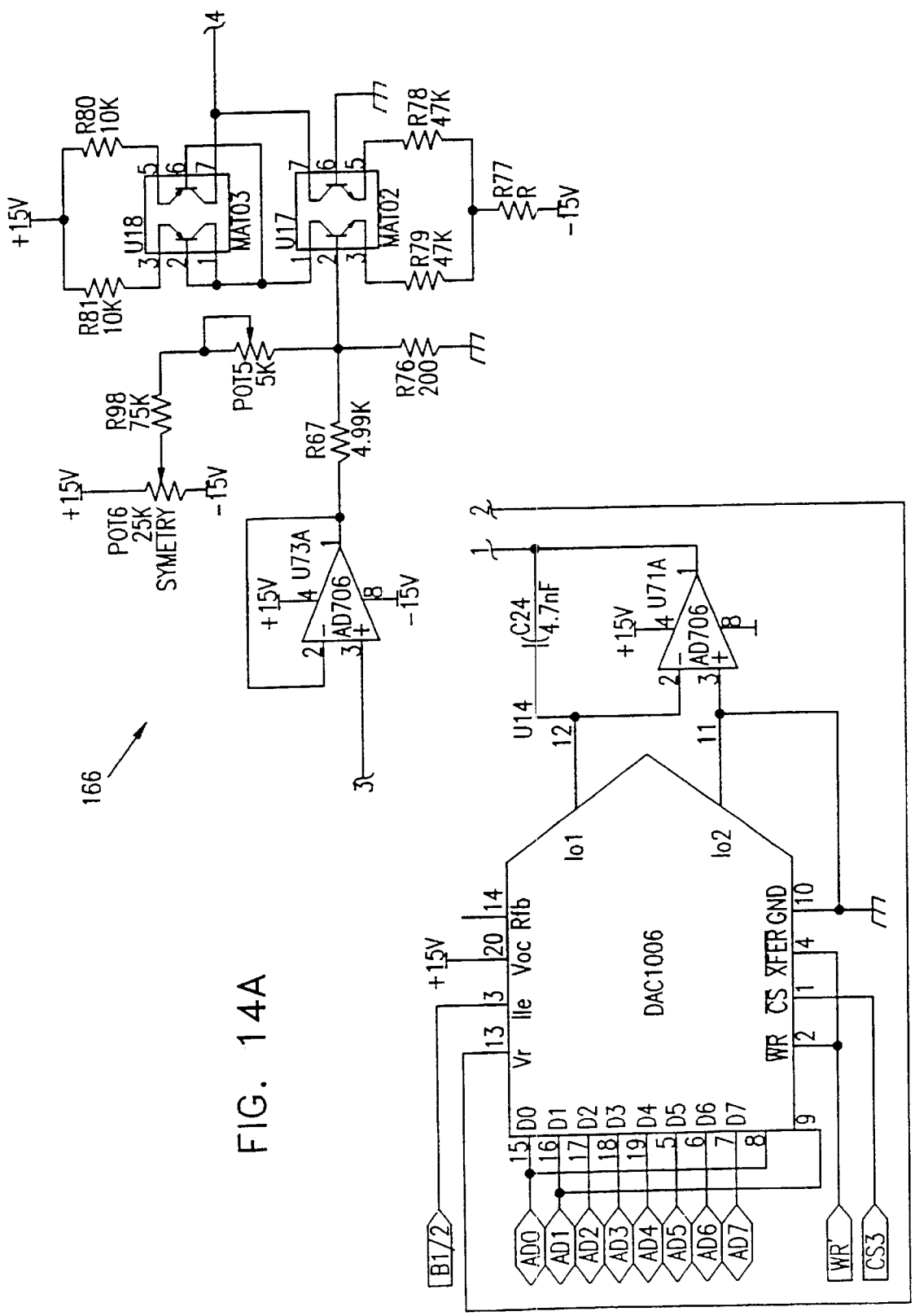
Figure 14B:
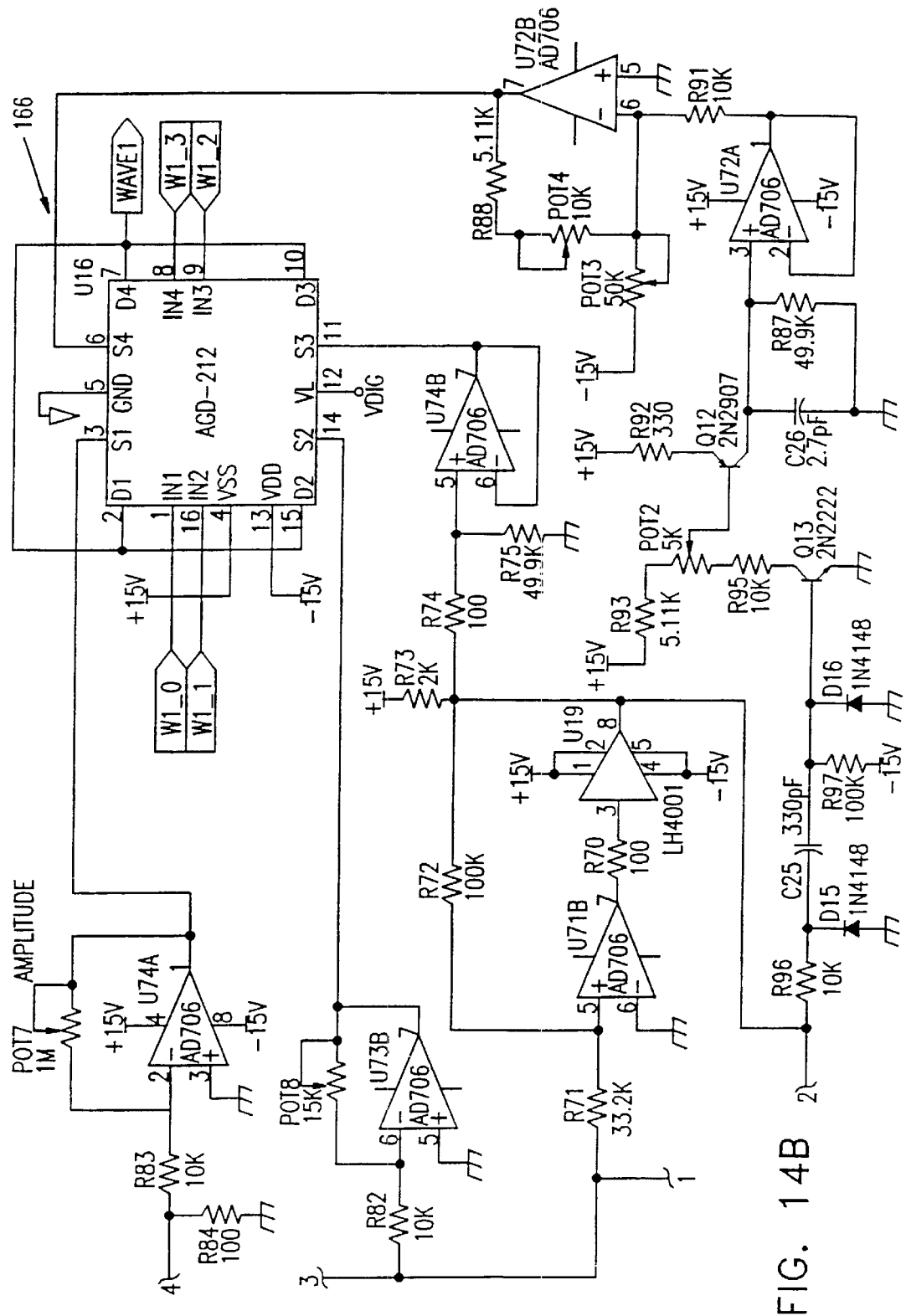
Figure 15A:
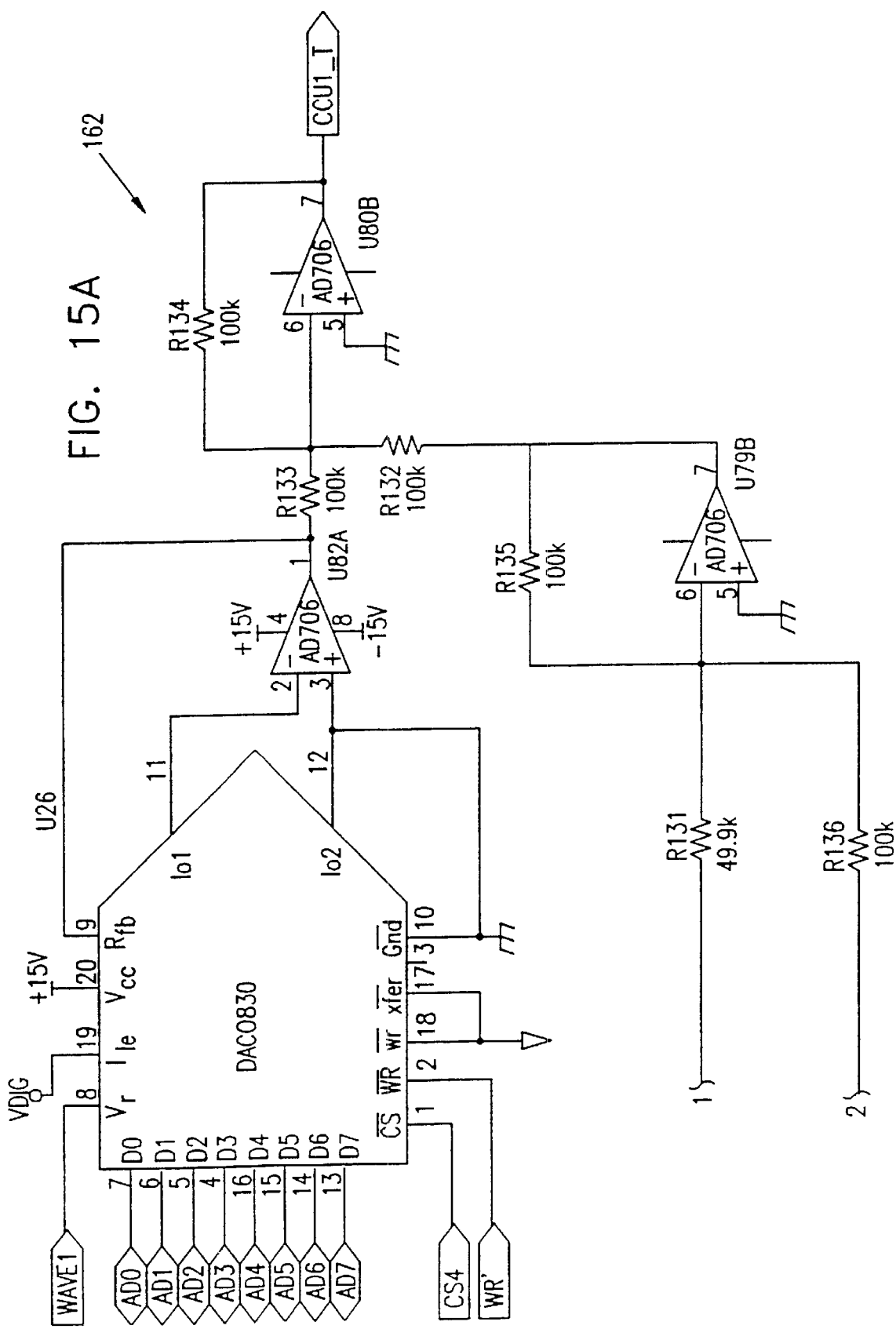
Figure 15B:
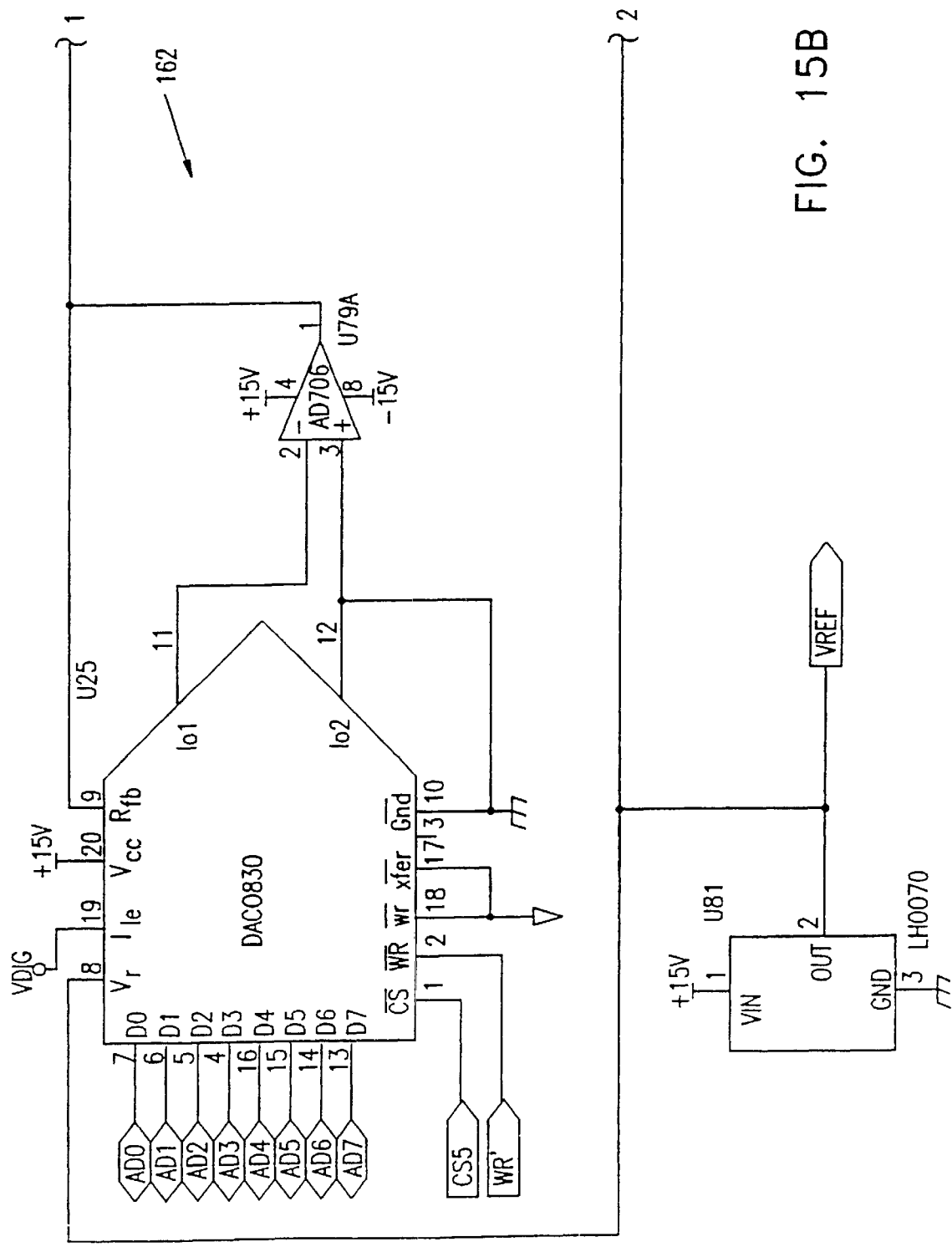
Figure 15C:
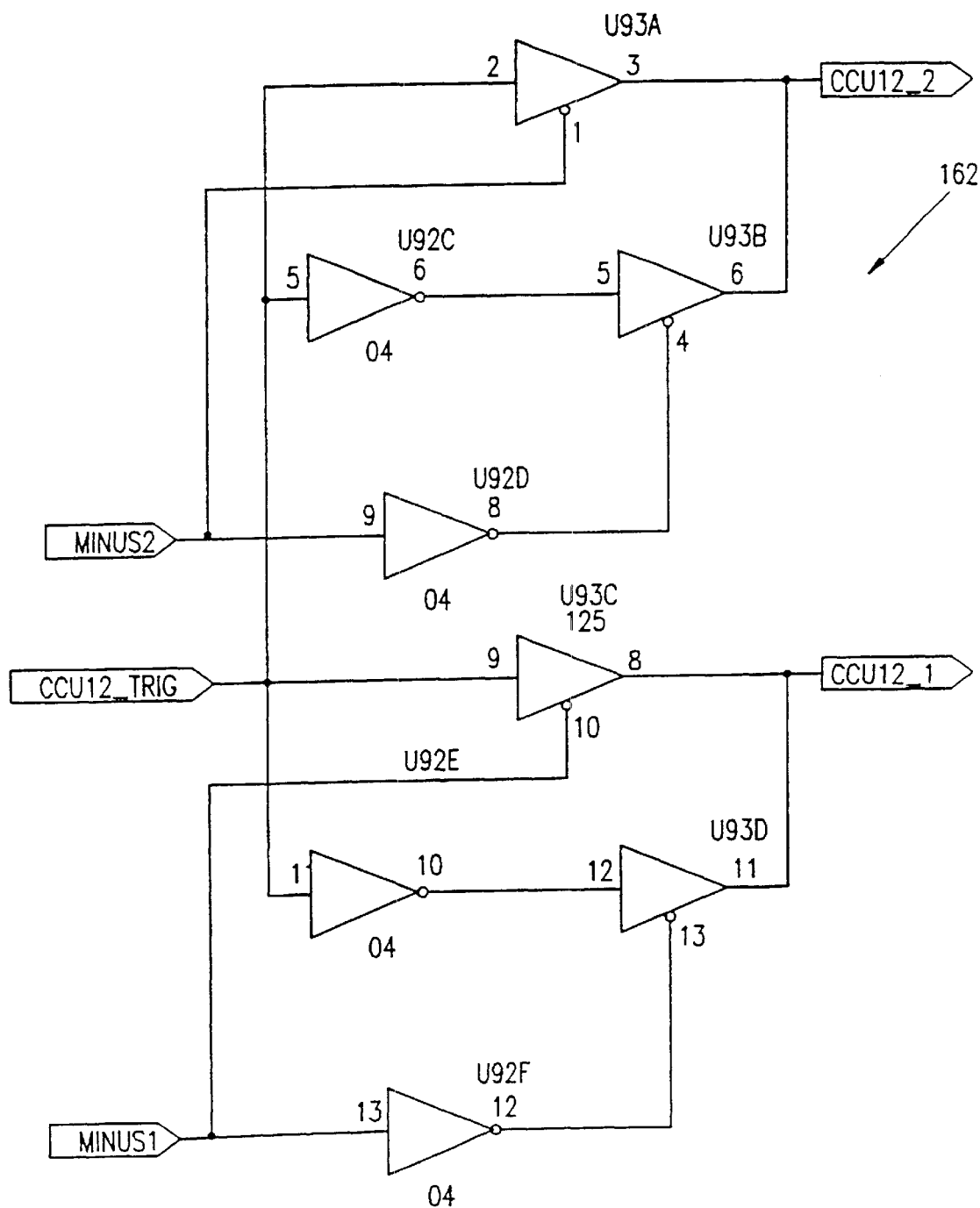
Figure 16:
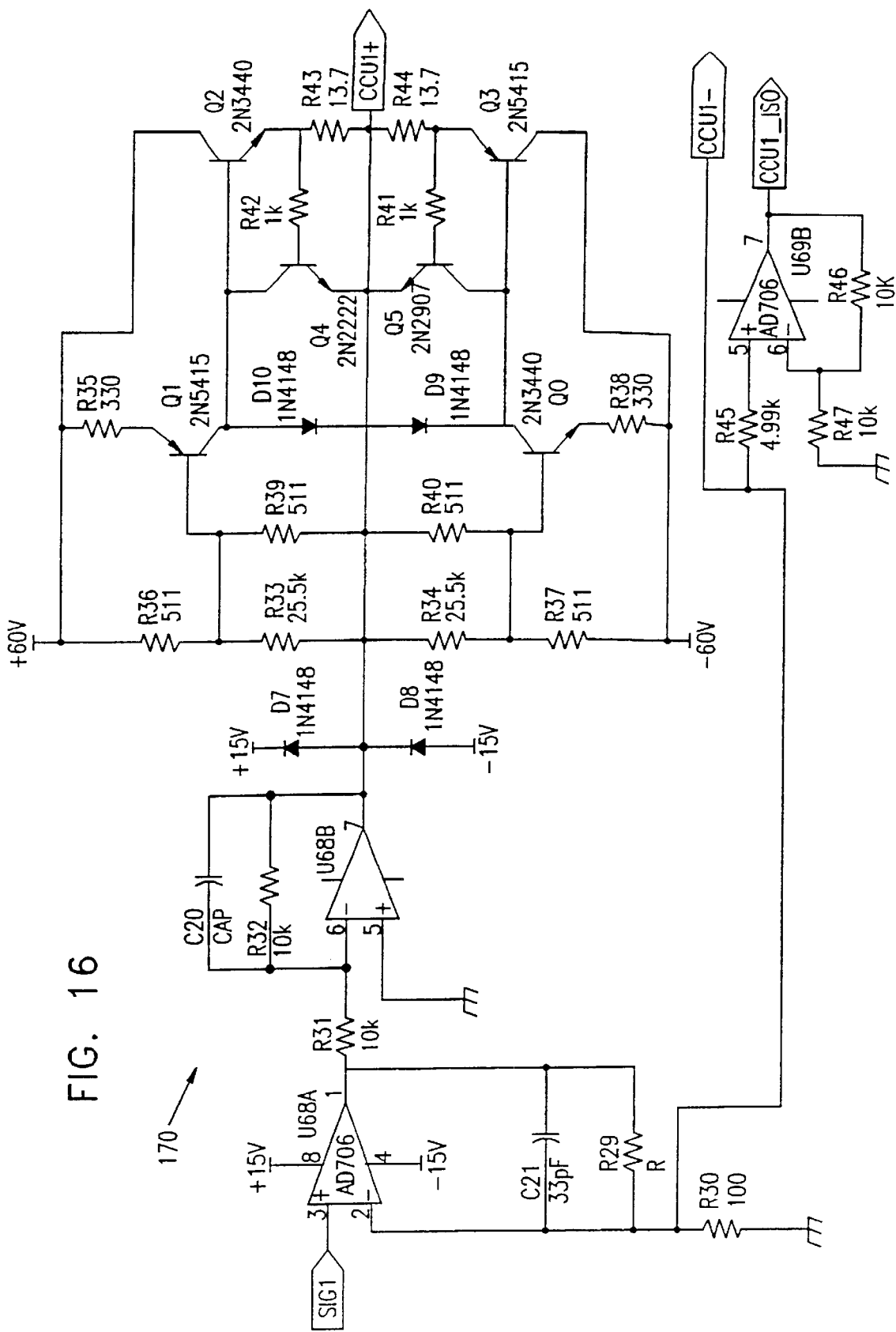
Figure 17A:
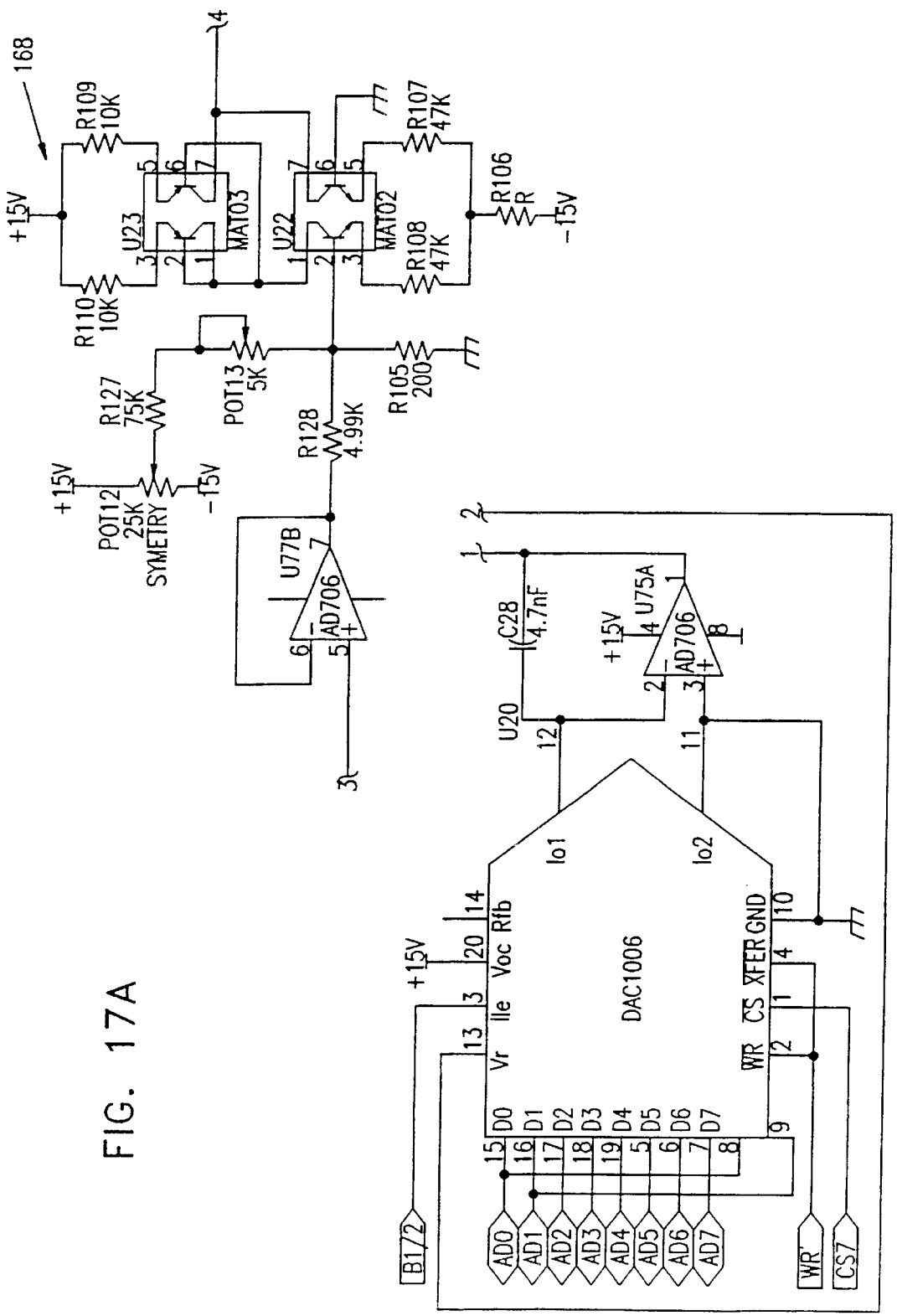
Figure 17B:
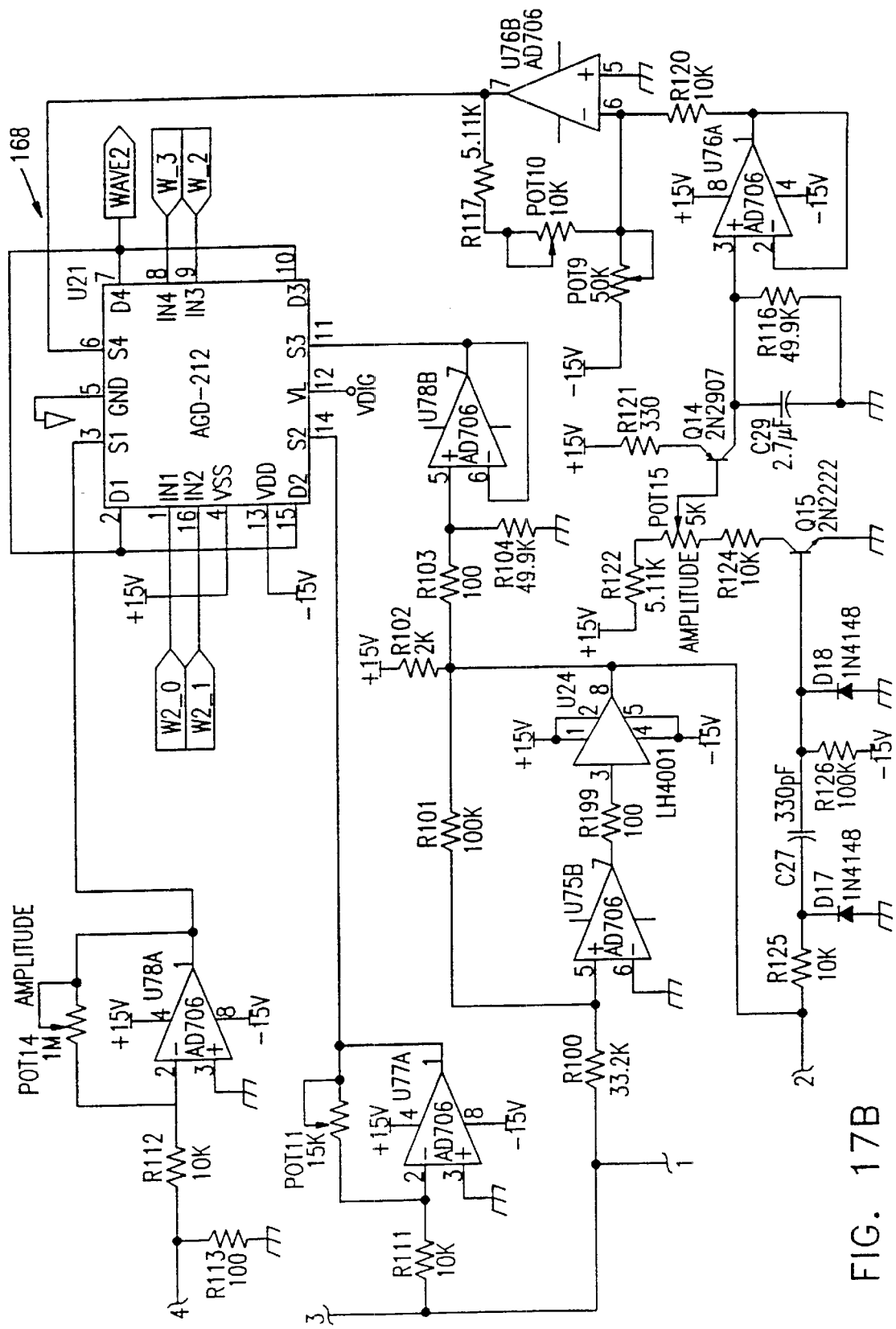
Figure 18A:
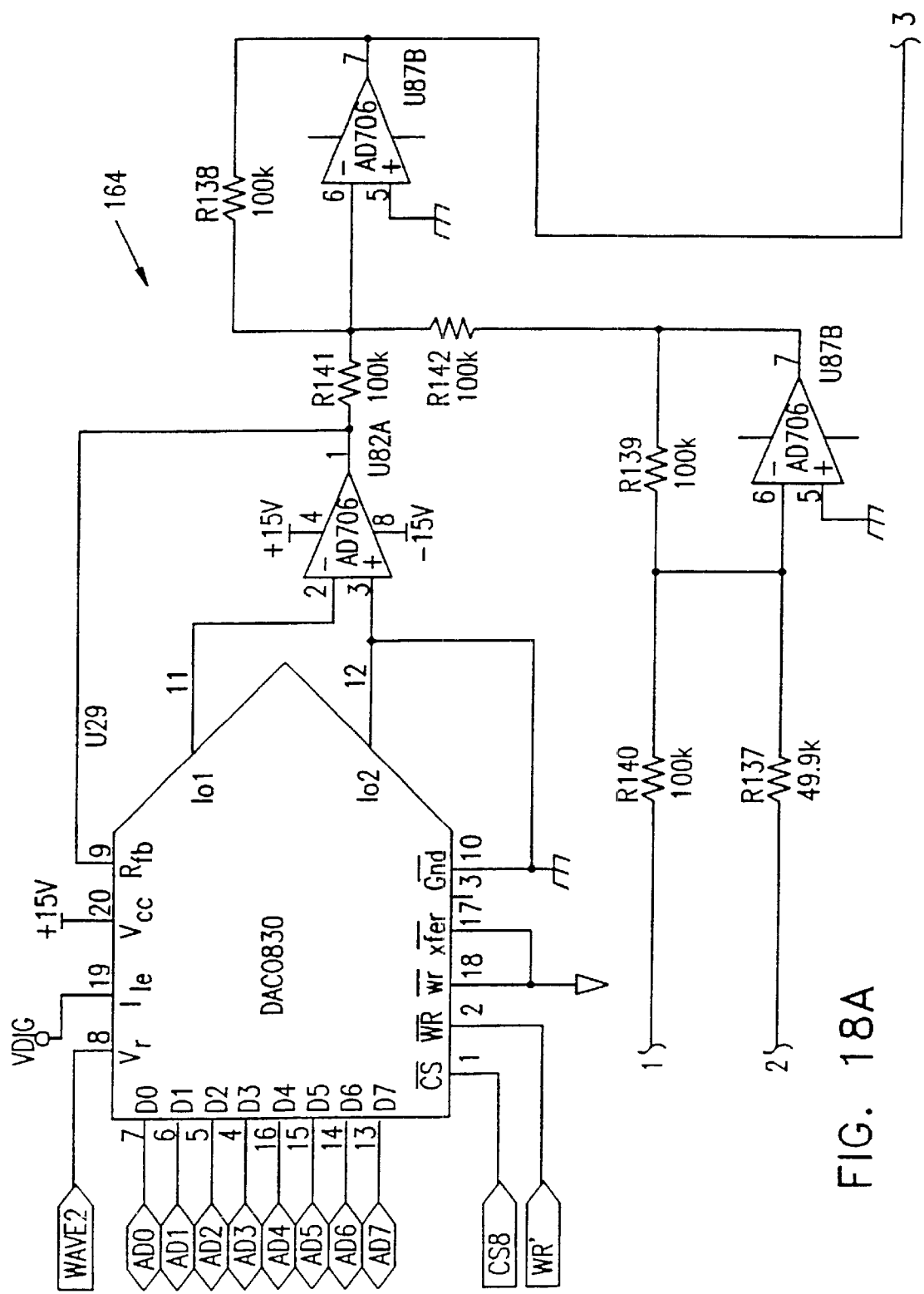
Figure 18B:
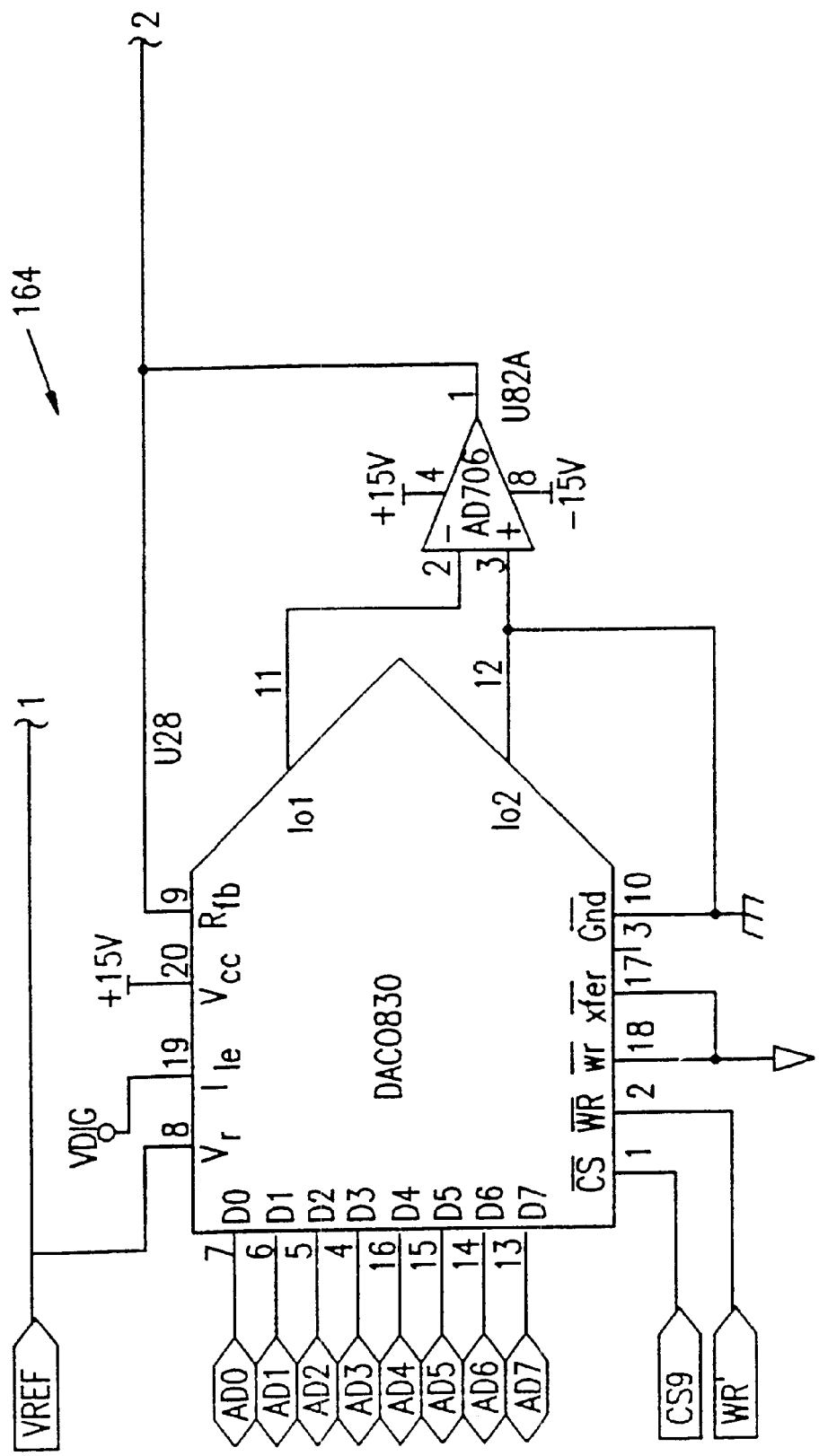
Figure 18C:
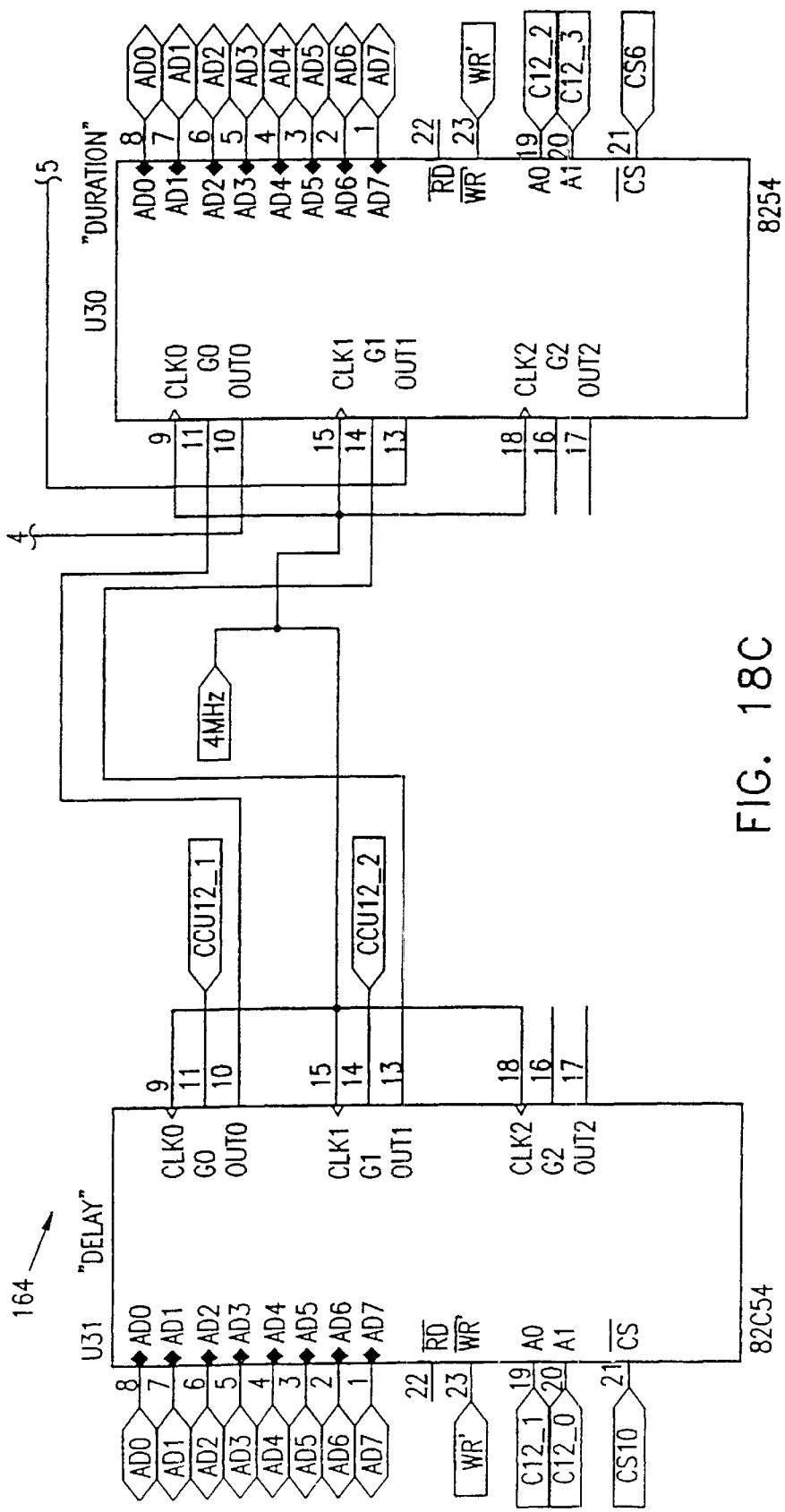
Figure 18D:
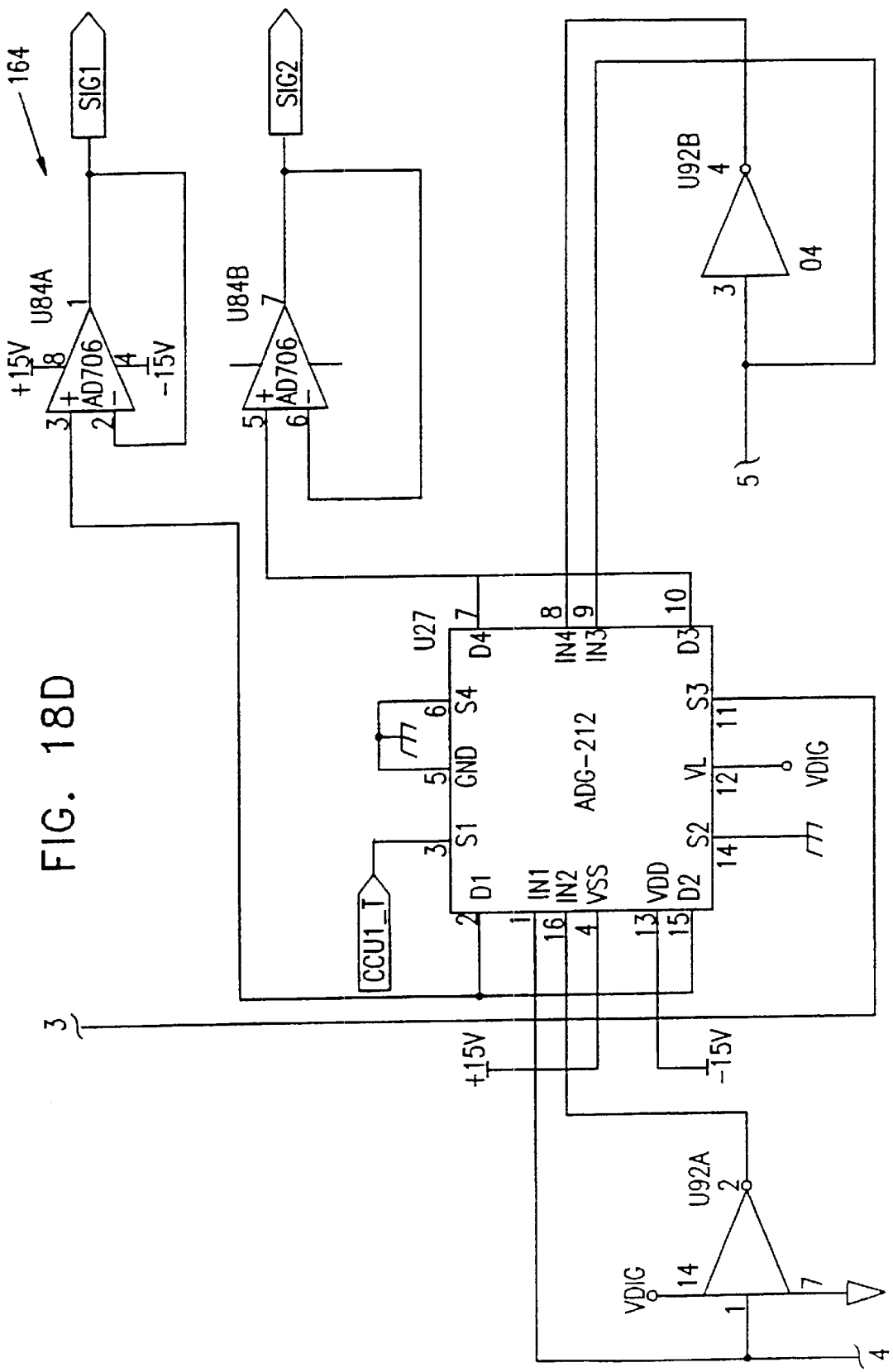
Figure 19:
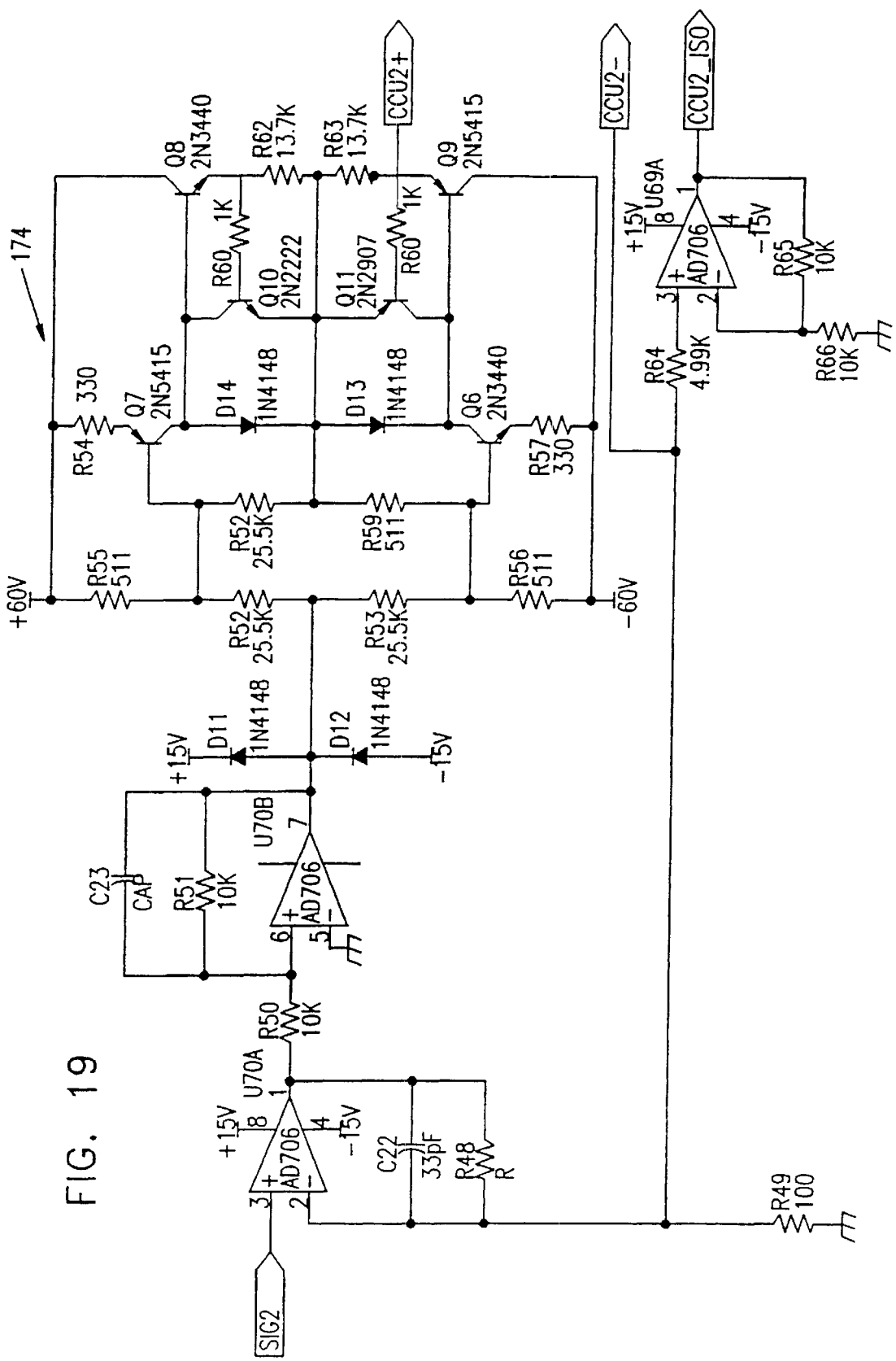
Figure 20:
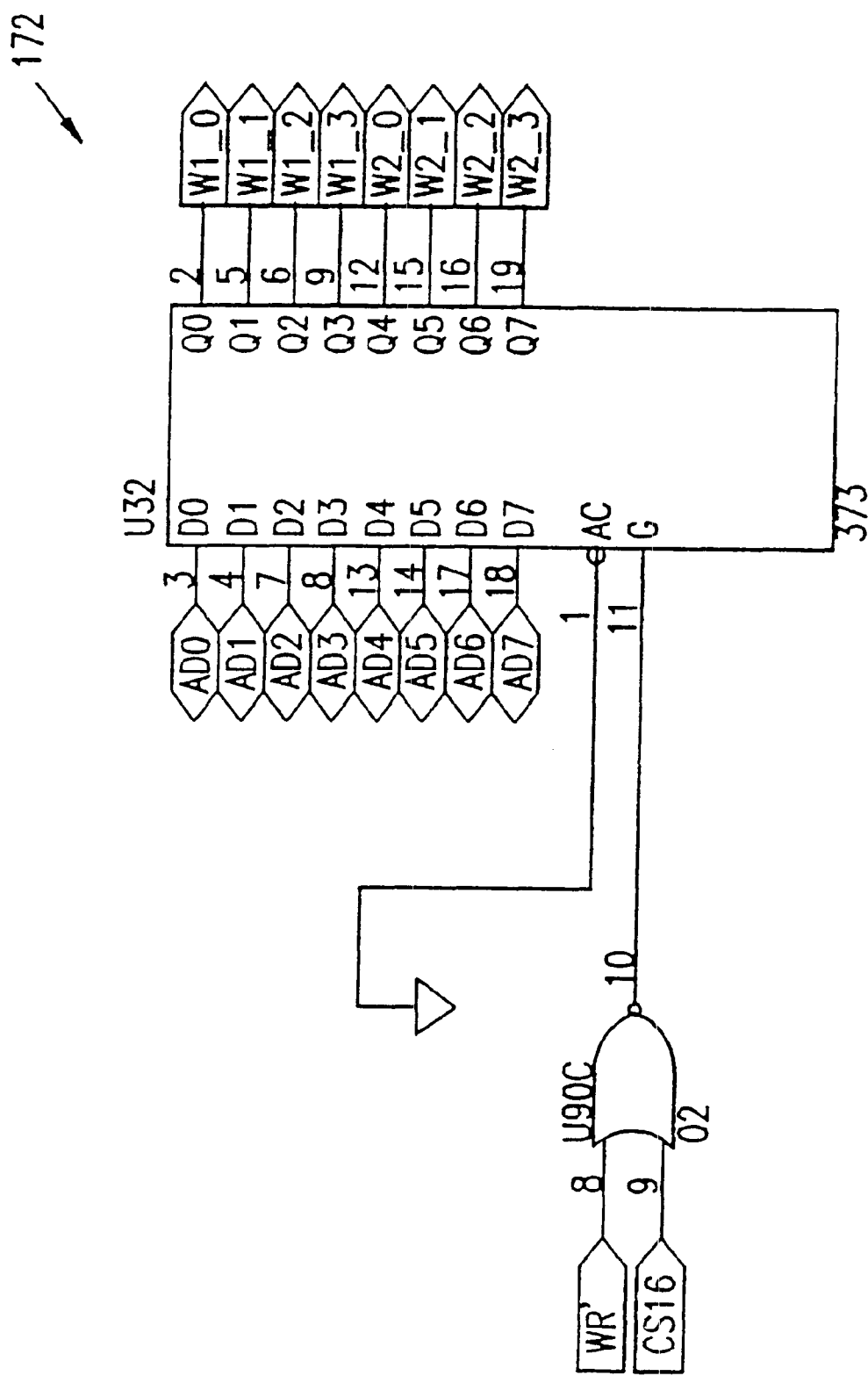

FIGS. 13A, 13B and 13C illustrate first CCU section 140, which generates two channels of non-excitatory stimulation pulses. CCU section 140 includes two control units 162 and 164, waveform generators 166 and 168, power units 170 and 174, and a waveform selector 172. FIGS. 14A and 14B show details of waveform generator 166, which drives a first one of the two non-excitatory channels, while FIGS. 17A and 17B show waveform generator 168, which is substantially similar to generator 166 and drives the second channel. FIGS. 15A, 15B and 15C illustrate control unit 162, which receives and scales the waveform from generator 166. FIG. 15C shows timing control logic common to both control units 162 and 164. FIGS. 18A, 18B, 18C and 18D illustrate control unit 164, wherein FIGS. 18A and 18B show waveform scaling circuitry similar to that in FIGS. 15A and 15B, FIGS. 18C and 18D include circuitry for controlling the relative delays of the pulses generated by the two stimulation channels. FIGS. 16 and 19 show details of power units 174 and 178, respectively, and FIG. 20 illustrates wave selector 176.

Figure 21:
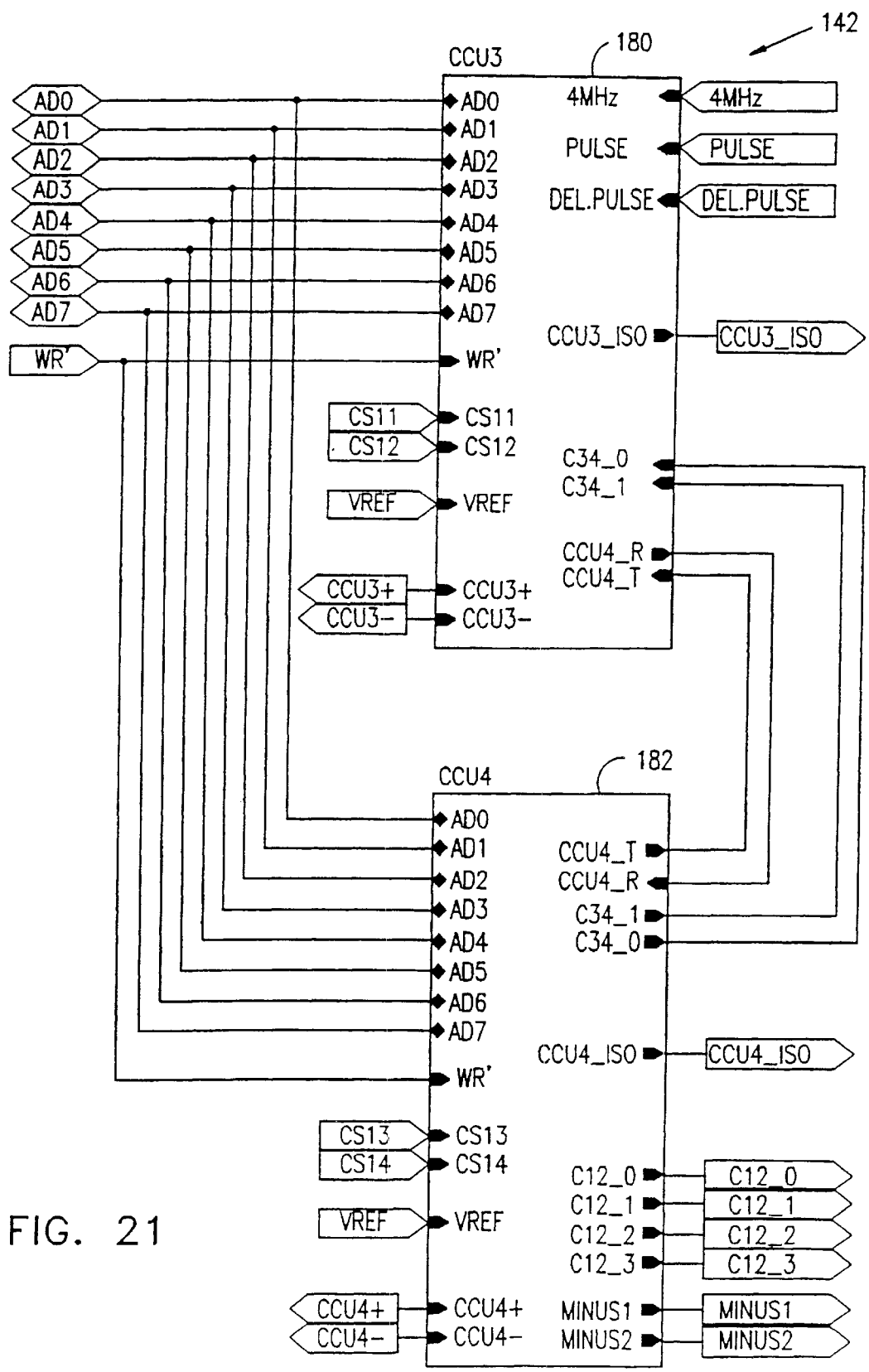
Figure 22A:
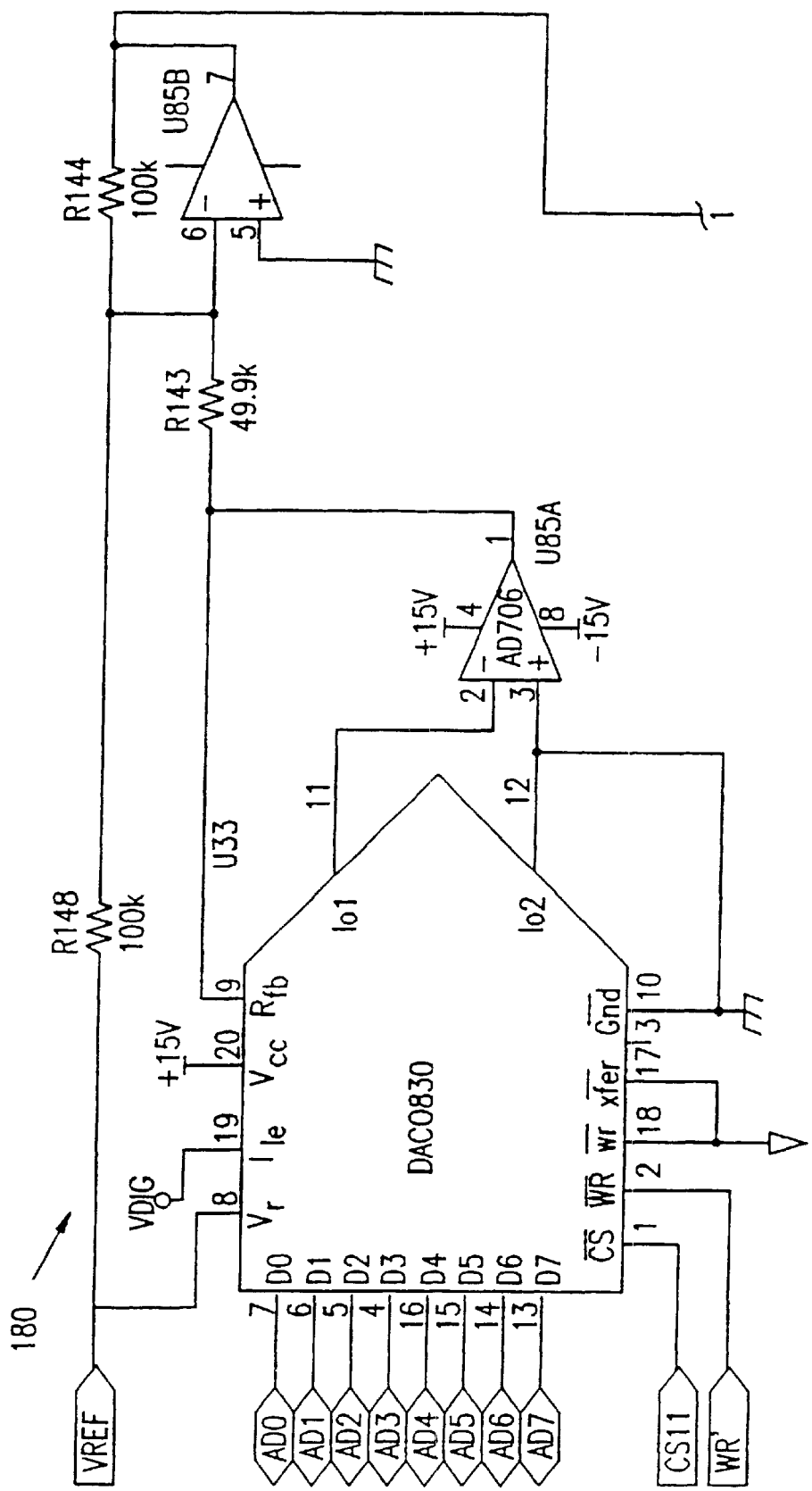
Figure 22B:
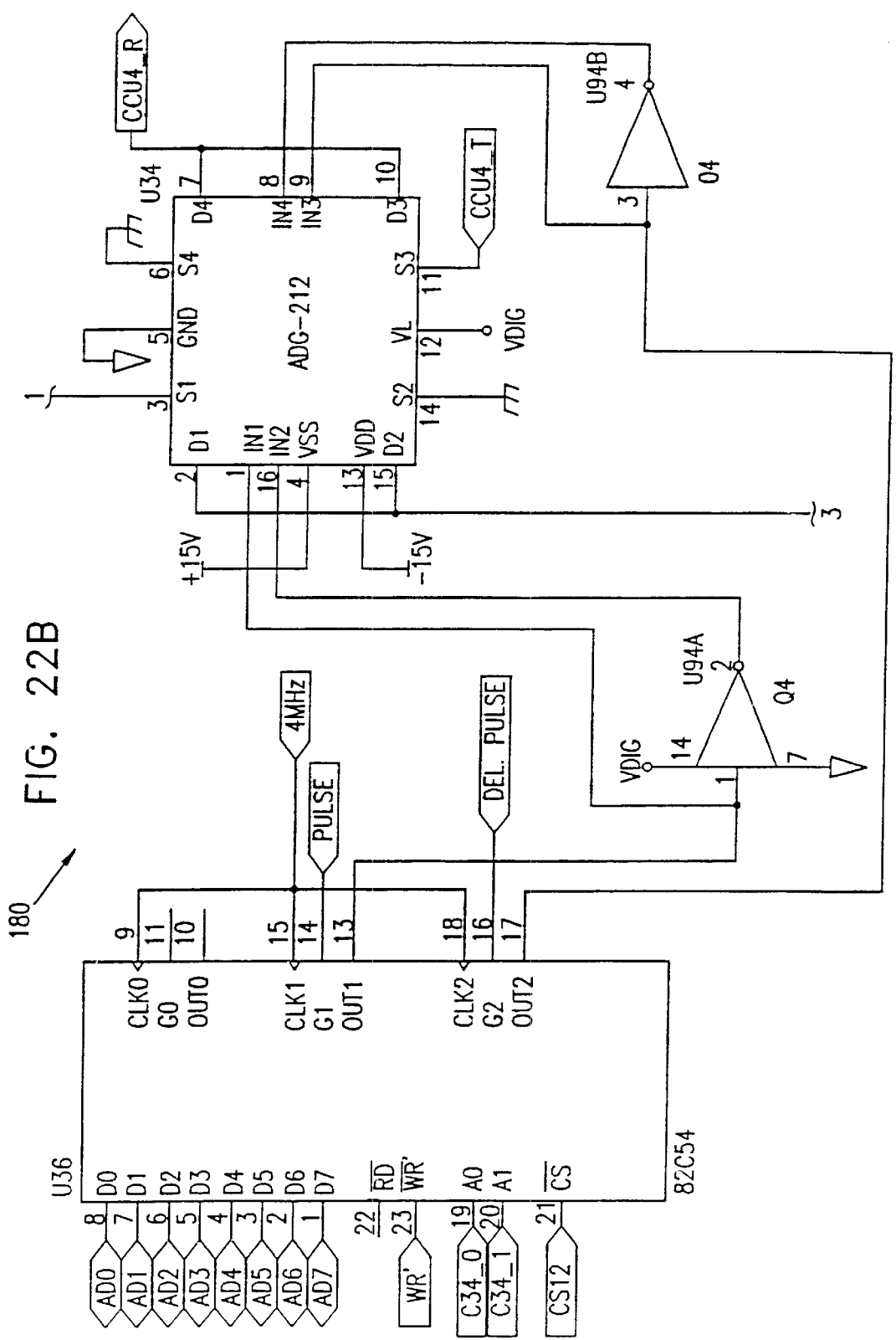
Figure 22C:
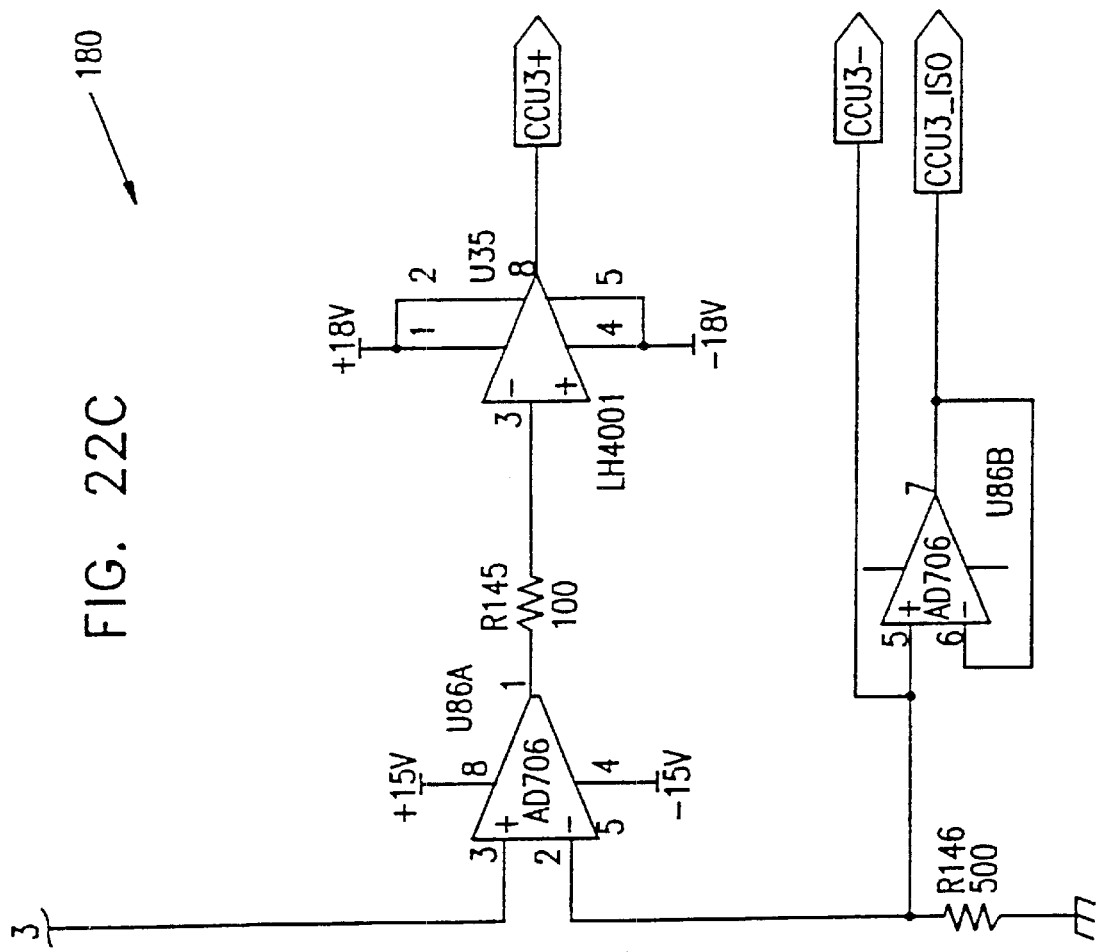
Figure 23A:
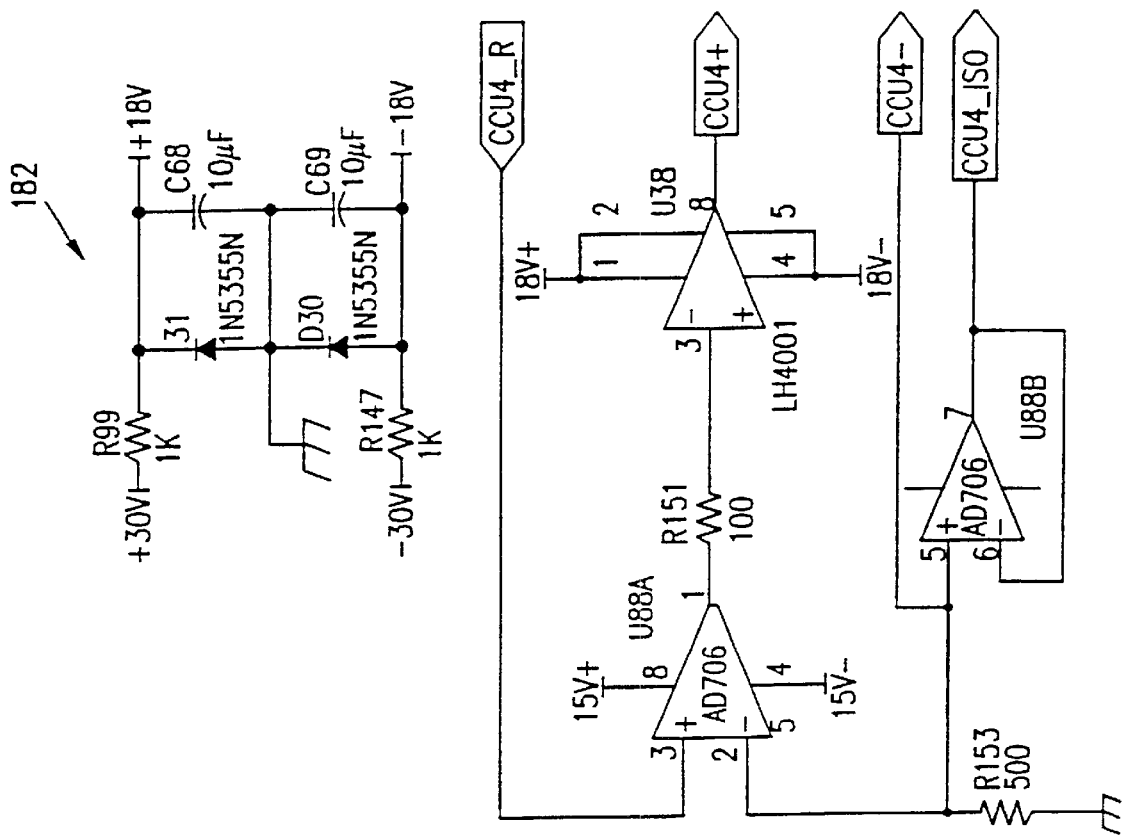
Figure 23A:
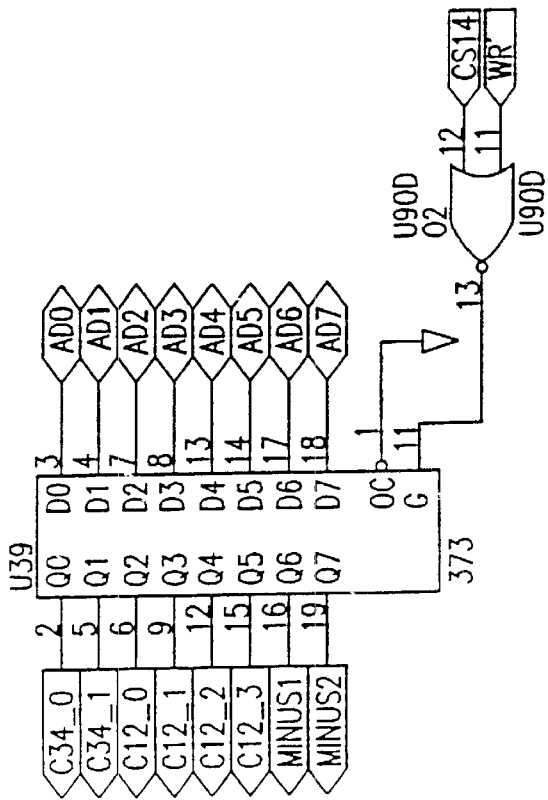
Figure 23B:
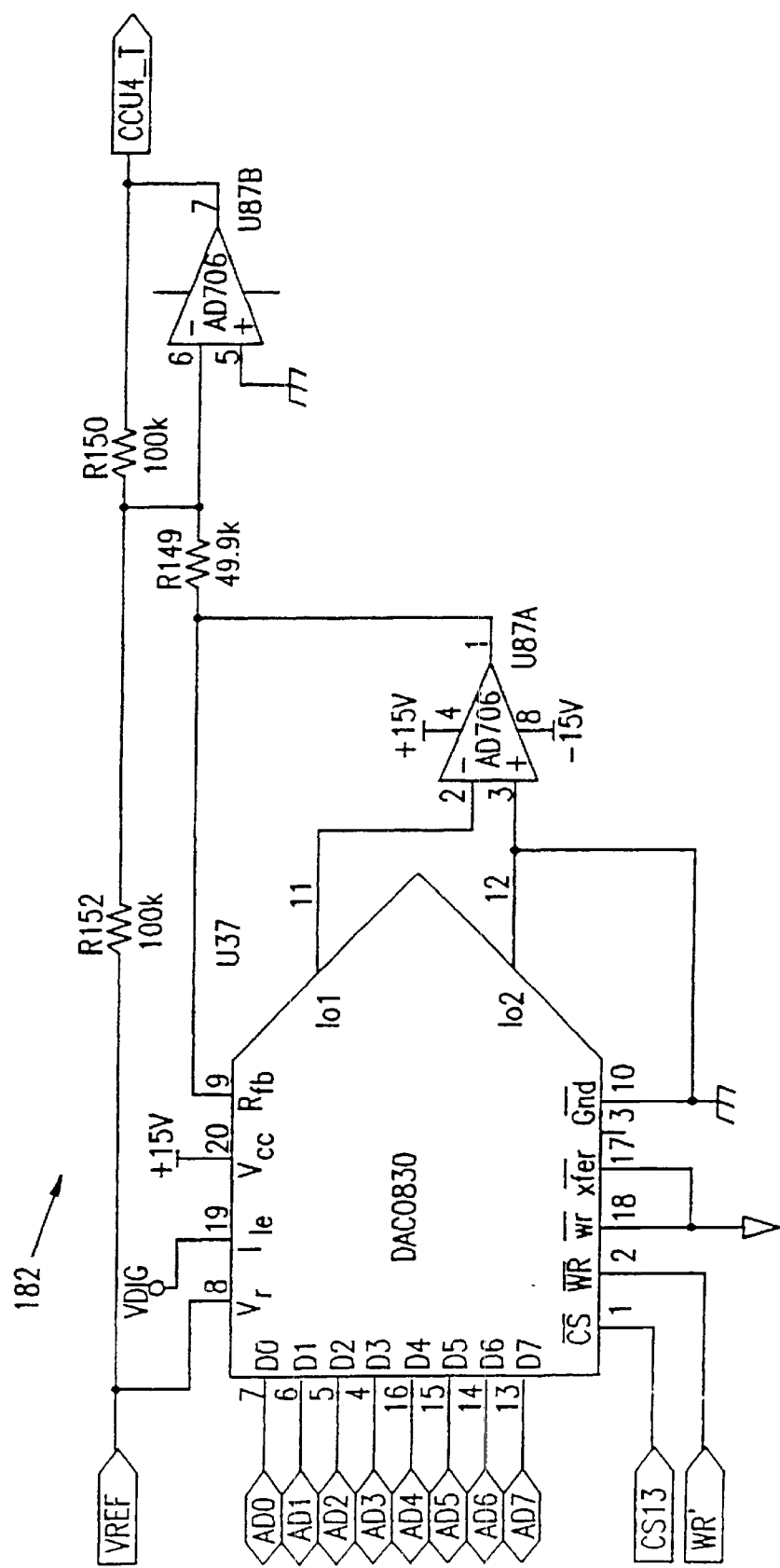
Figure 24:
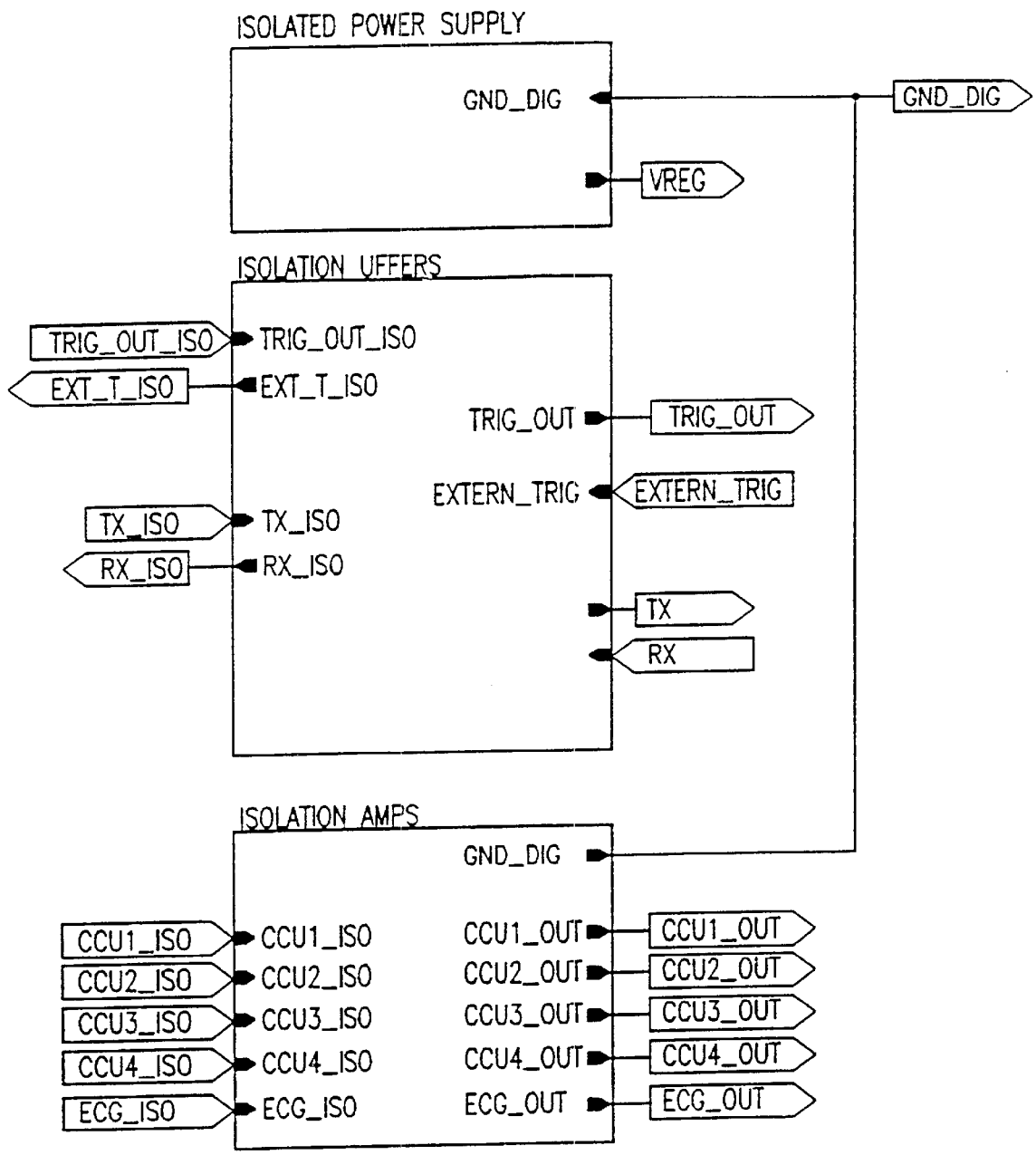
Figure 25A:
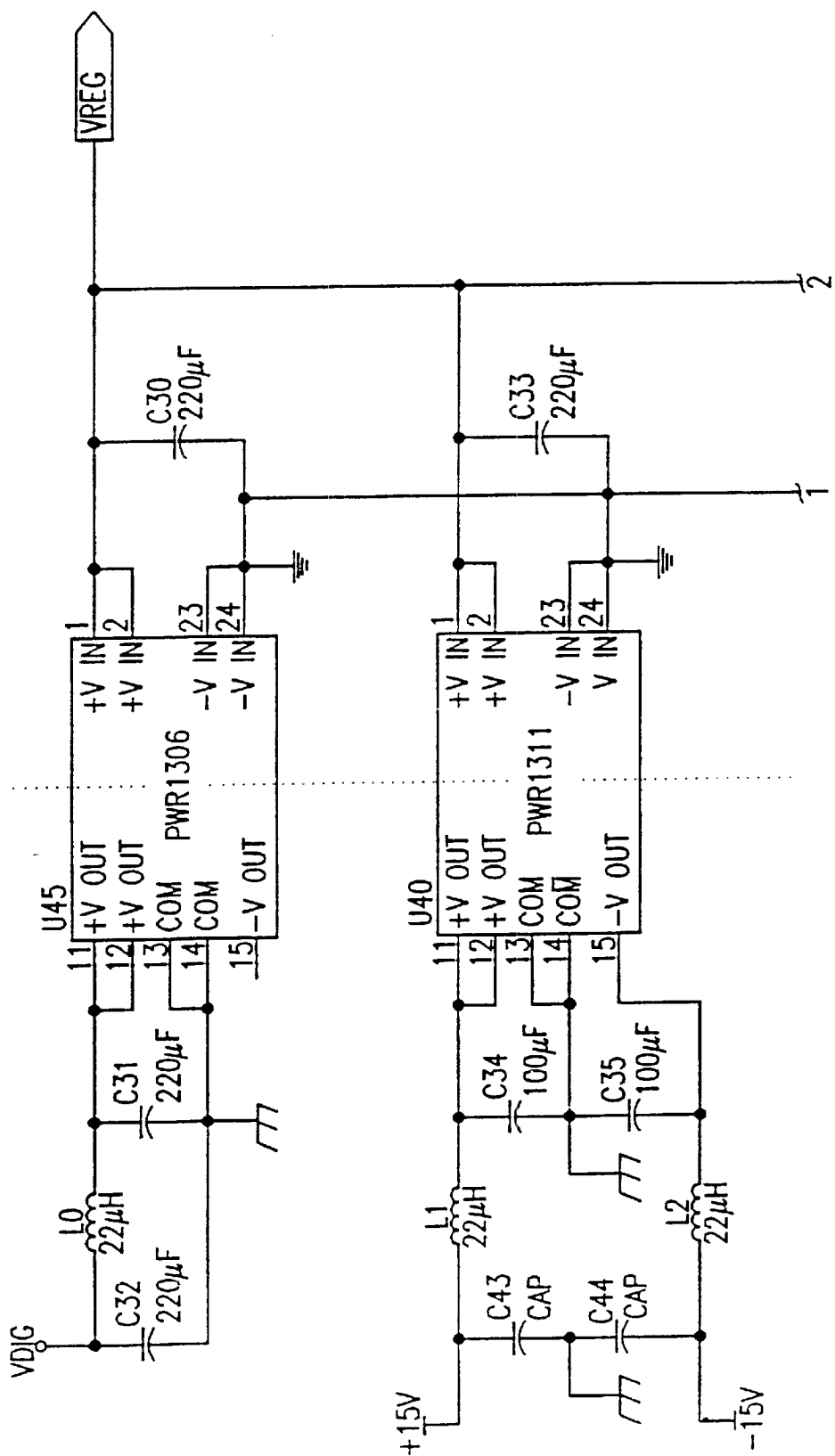
Figure 25B:
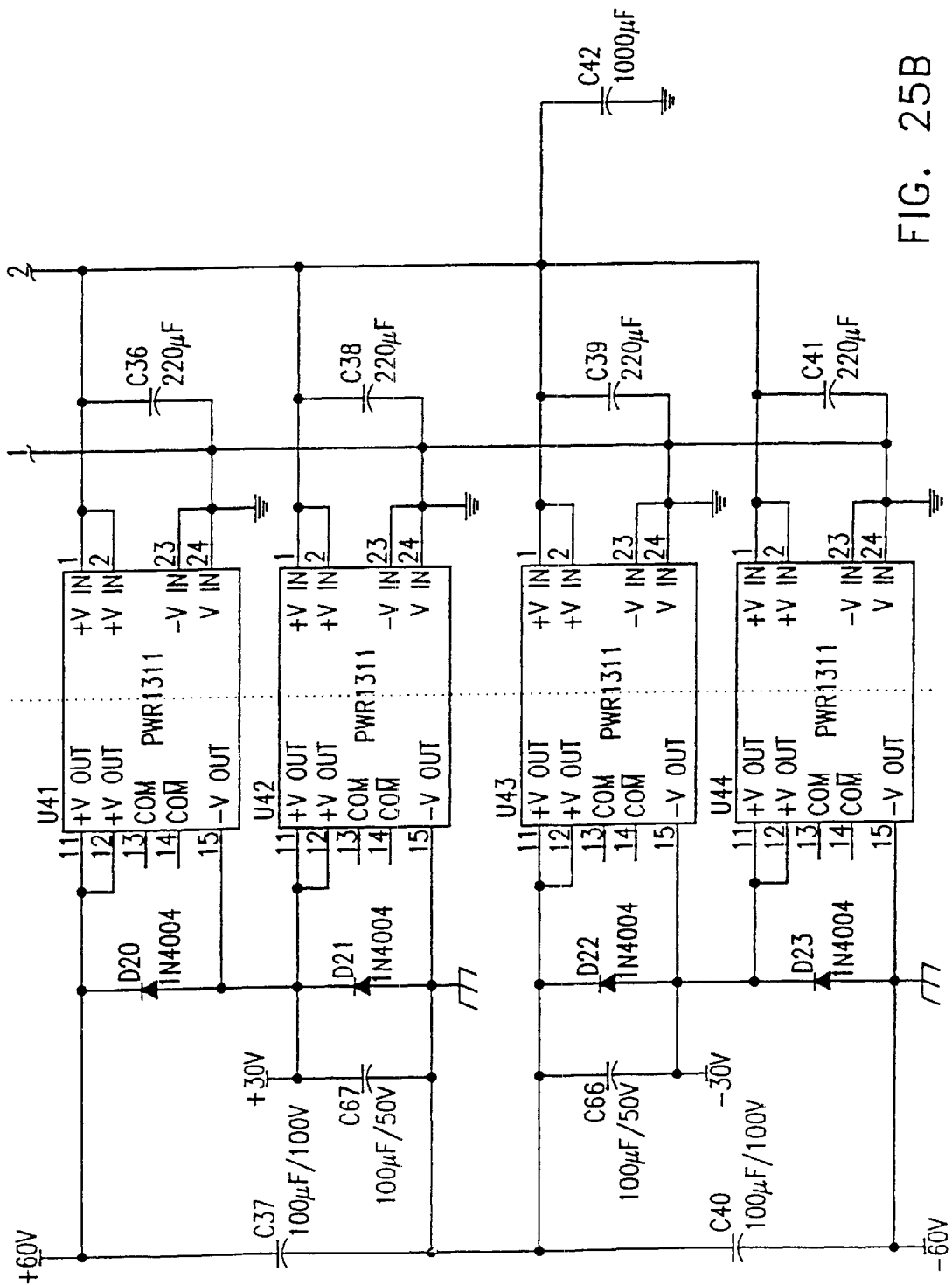
Figure 26:
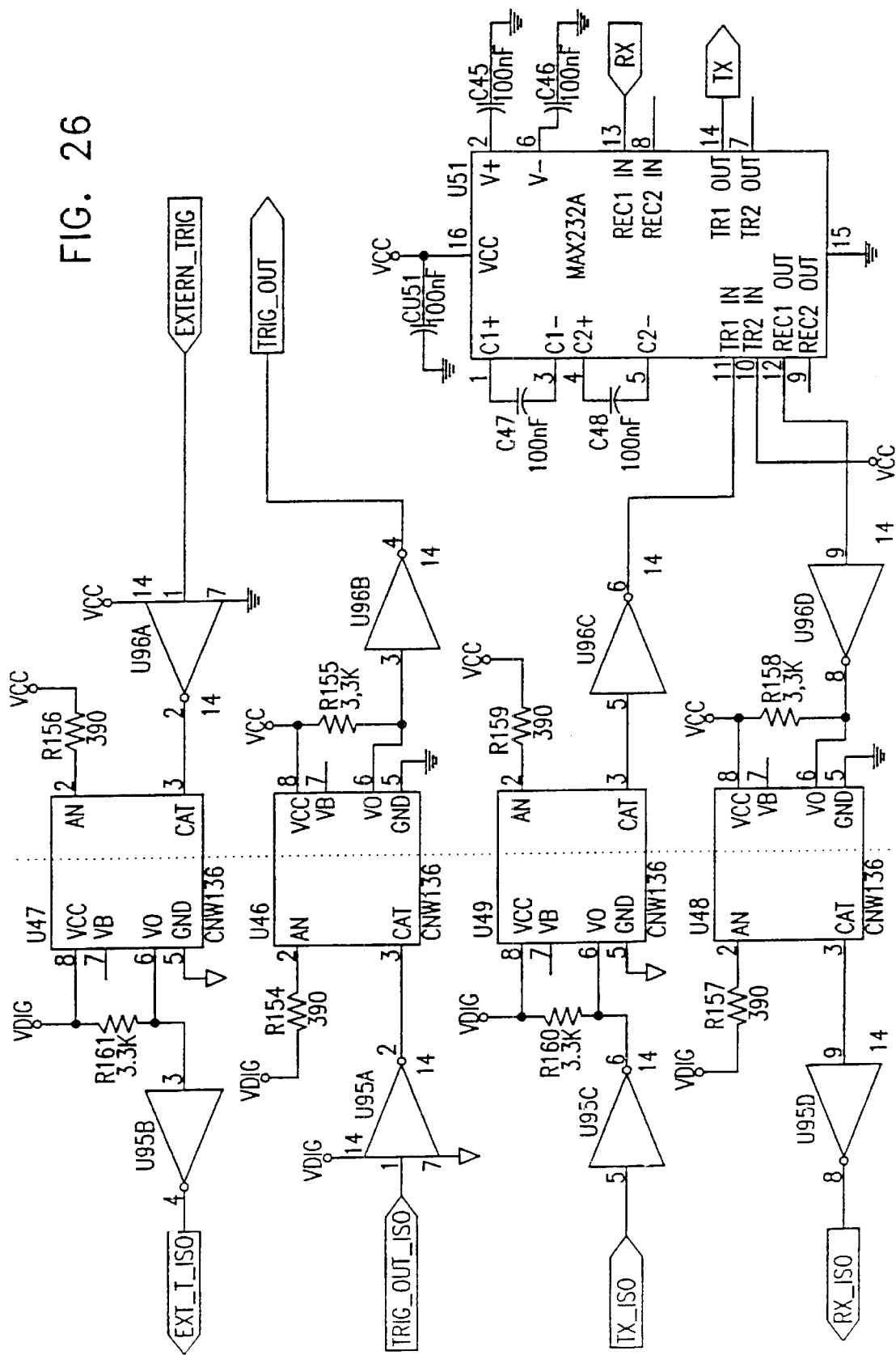
Figure 27A:
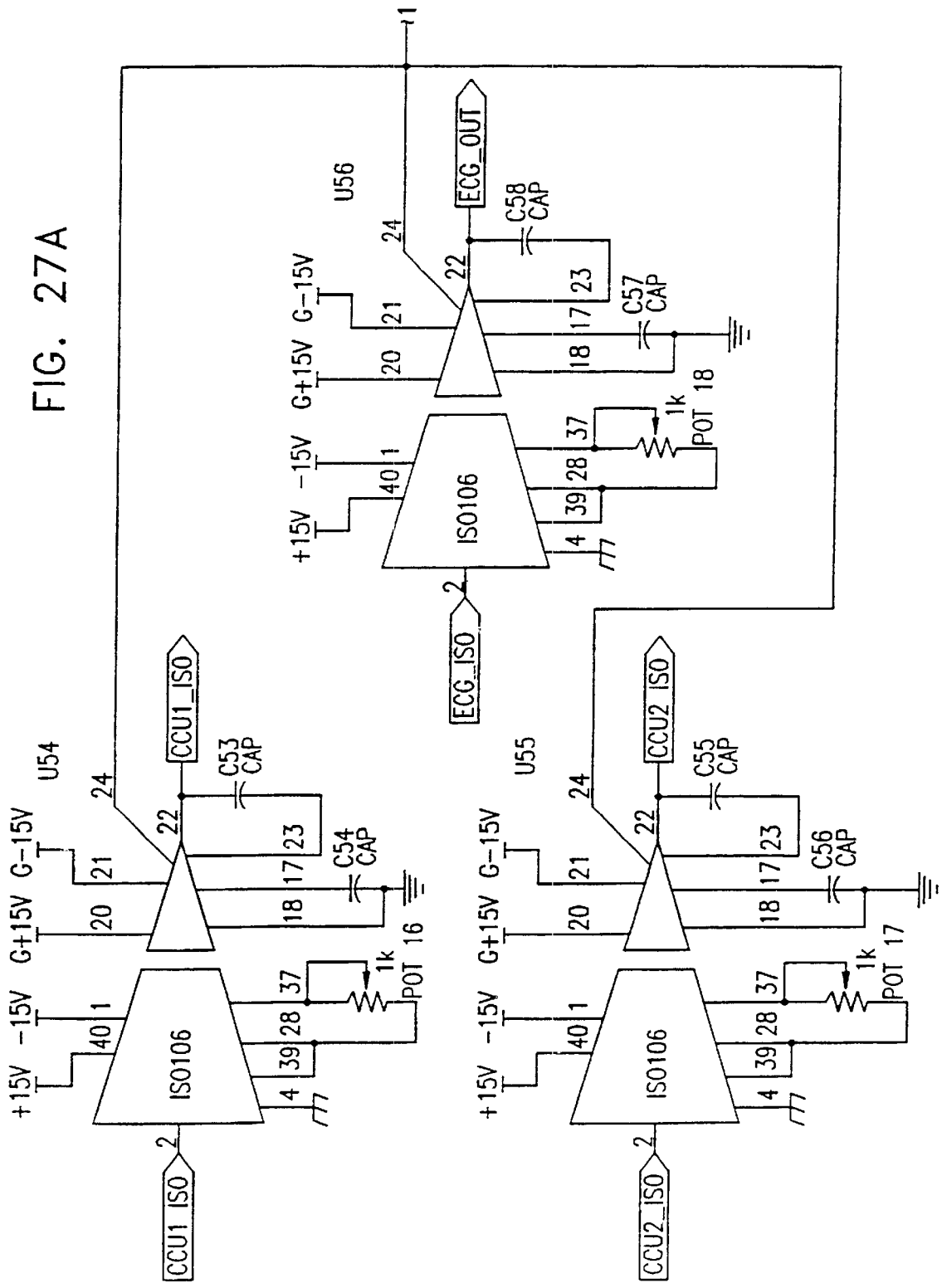
Figure 27B:
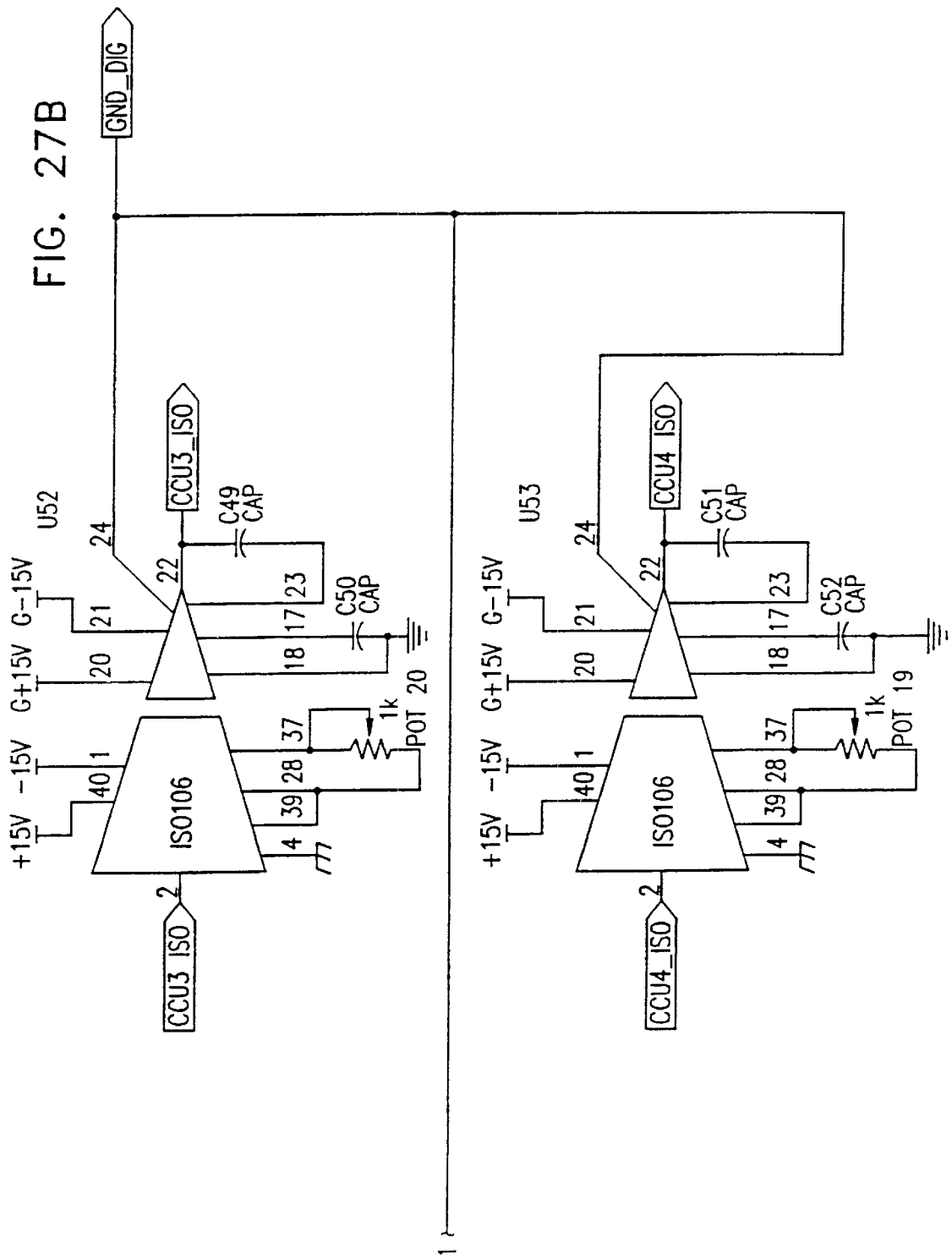

FIG. 21 shows second CCU section 142, including two CCU channels 180 and 182, for generating pacing pulses at predetermined rates and a relative delay therebetween, similar to pacemakers known in the art FIGS. 22A, 22B and 22C show details of channel 180. FIGS. 23A and 23B show details of channel 182, which is switched by the same switch and counters as channel 180 (shown in FIG. 22B).

Figure 28:
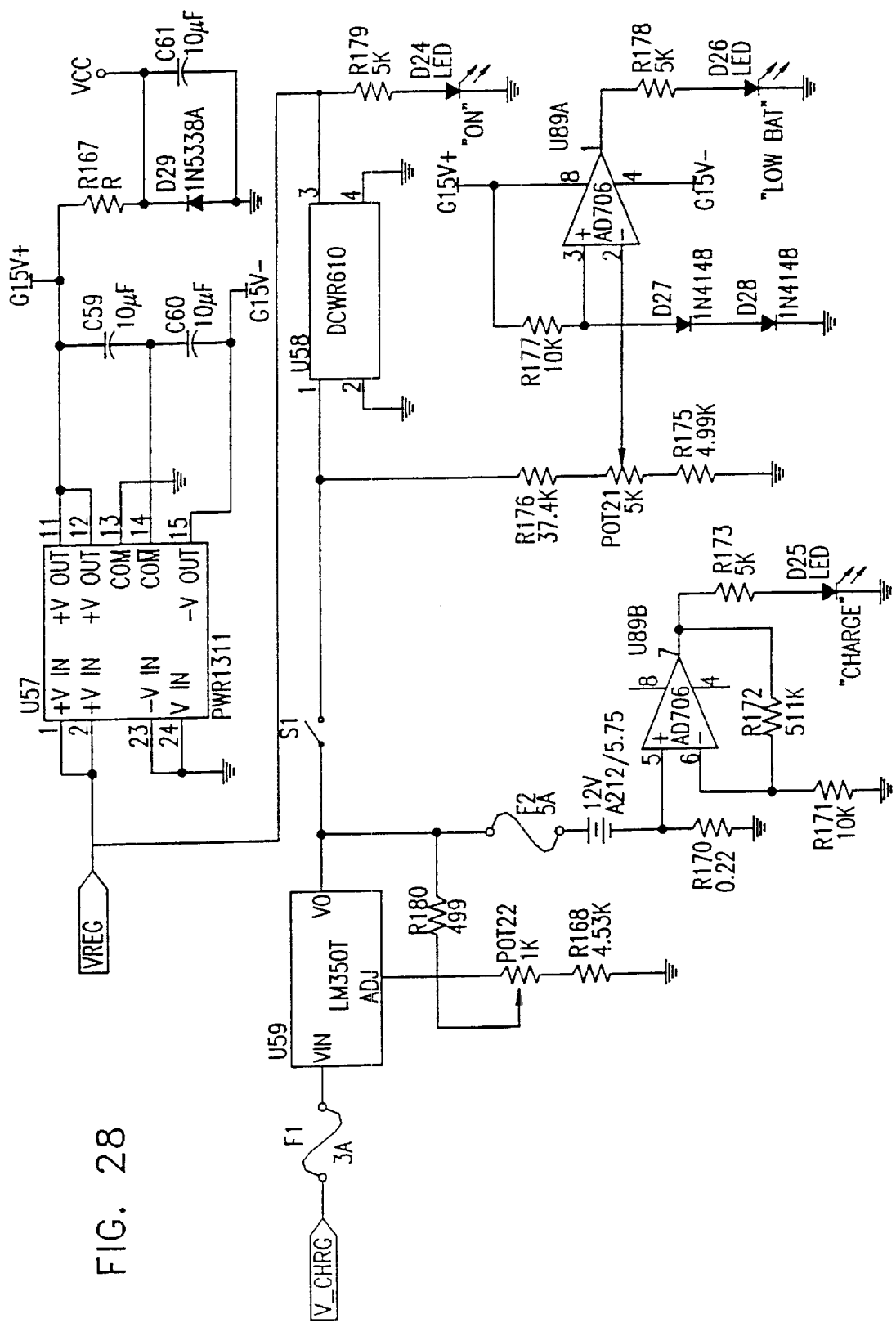
Figure 29:
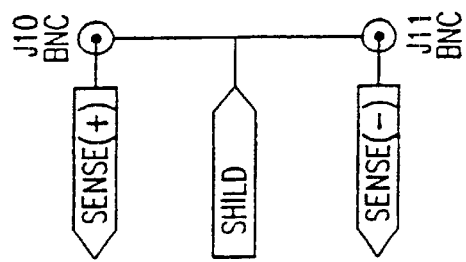
Figure 29:
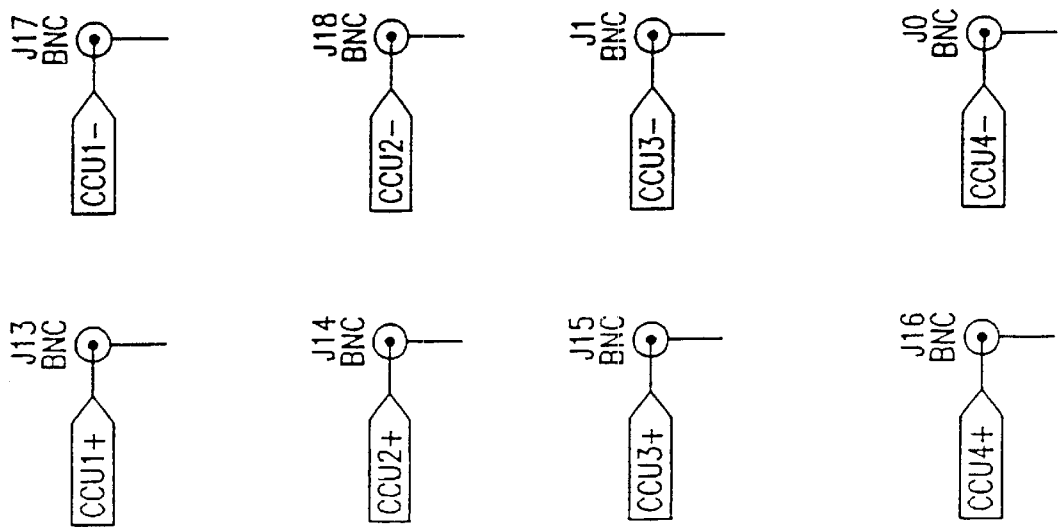
Figure 30:
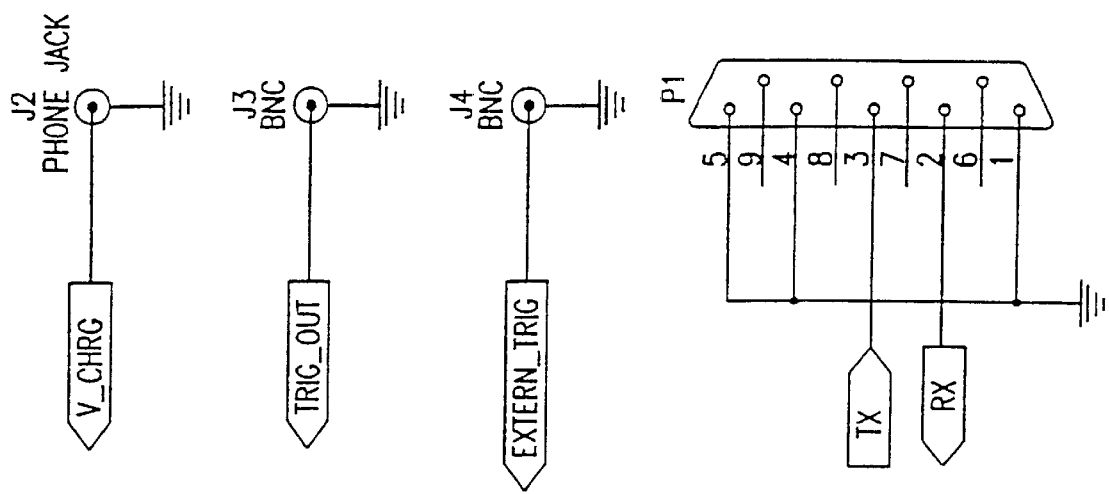
Figure 30:
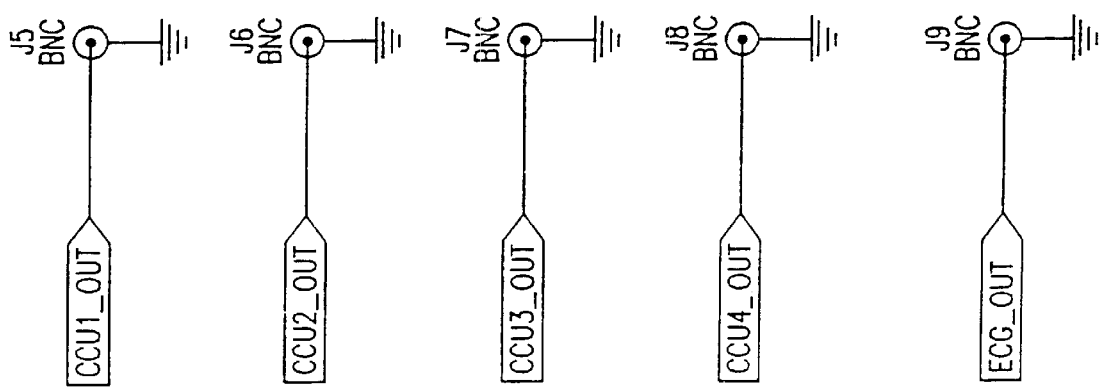

FIGS. 24, 25A, 25B, 26, 27A and 27B show details of isolation circuitry, which is used when circuitry 22 is to be run while connected to external power. FIG. 28 illustrates a battery charging circuit. FIGS. 29 and 30 show front and rear panel connections, respectively.

Although in some of the preferred embodiments described above, for example, as shown in FIG. 2A, circuitry 22 is shown as beings contained within an implantable case 26, the specific implementation of the circuitry exemplified by FIGS. 6–30 is better suited to be contained in an external, bedside case, in accordance with the best mode of the invention practiced at present. It will be understood that the circuitry of FIGS. 6–30 can be suitably altered and miniaturized to fit in an implantable case, using methods and electronic devices known in the art, particularly such as are currently used in implantable pacemakers. On the other hand, under some circumstances, pacing and non-excitatory stimulation may be best accomplished using such an external, bedside case, when tile heart must be paced and/or the cardiac output regulated temporarily, for example, during recovery from infarction or surgery.

It will be appreciated that the preferred embodiments described above are cited by way of example, and the full scope of the invention is limited only by the claims.

What is claimed is:

1. Apparatus for heart pacing with cardiac output modification, comprising;

one or more electrodes adapted to apply electrical signals to cardiac muscle segments;

signal generation circuitry adapted to apply an excitatory electrical pulse to at least one of the electrodes to pace the heart and a non-excitatory stimulation pulse of a magnitude and at a timing at which it is unable to generate a propagating action potential to at least one of the one or more electrodes to modify the cardiac output; and an electrode which senses cardiac electrical activity and is coupled to the signal generation circuitry, wherein the circuitry detects a QT interval in the cardiac electrical activity.

2. Apparatus for heart pacing with cardiac output modification, comprising:

one or more electrodes adapted to apply electrical signals to cardiac muscle segments;

signal generation circuitry adapted to apply an excitatory electrical pulse to at least one of the one or more electrodes to pace the heart and a non-excitatory stimulation pulse of a magnitude and at a timing at which it is unable to generate a propagating action potential to at least one of the one or more electrodes to modify the cardiac output; and at least one pressure sensor which senses cardiac activity, wherein the sensor is coupled to the signal generation circuitry, which generates the pulses responsive thereto.

3. Apparatus for heart pacing with cardiac output modification, comprising:

one or more electrodes adapted to apply electrical signals to cardiac muscle segments;

signal generation circuitry adapted to apply an excitatory electrical pulse to at least one of the one or more electrodes to pace the heart and a non-excitatory stimulation pulse of a magnitude and at a timing at which it is unable to generate a propagating action potential to at least one of the one or more electrodes to modify the cardiac output; and at least one flow rate sensor which senses cardiac activity, wherein the sensor is coupled to the signal generation circuitry, which generates the pulses responsive thereto.

4. Apparatus for heart pacing with cardiac output modification, comprising:

one or more electrodes adapted to apply electrical signals to cardiac muscle segments;

signal generation circuitry adapted to apply an excitatory electrical pulse to at least one of the one or more electrodes to pace the heart and a non-excitatory stimulation pulse of a magnitude and at a timing at which it is unable to generate a propagating action potential to at least one of the one or more electrodes to modify the cardiac output; and at least one oxygen sensor which senses cardiac activity, wherein the sensor is coupled to the signal generation circuitry, which generates the pulses responsive thereto.

5. Apparatus for heart pacing with cardiac output modification, comprising:

one or more electrodes adapted to apply electrical signals to cardiac muscle segments;

signal generation circuitry adapted to apply an excitatory electrical pulse to at least one of the one or more electrodes to pace the heart and a non-excitatory stimulation pulse of a magnitude and at a timing at which it is unable to generate a propagating action potential to at least one of the one or more electrodes to modify the cardiac output; and at least one temperature sensor which senses cardiac activity, wherein the sensor is coupled to the signal generation circuitry, which generates the pulses responsive thereto.

6. Apparatus for heart pacing with cardiac output modification, comprising:

one or more electrodes adapted to apply electrical signals to cardiac muscle segments; and signal generation circuitry adapted to apply an excitatory electrical pulse to at least one of the one or more electrodes to pace the heart and a non-excitatory stimulation pulse of a magnitude and at a timing at which it is unable to generate a propagating action potential to at least one of the one or more electrodes to modify the cardiac output, wherein the one or more electrodes comprise a net of addressable, non-excitatory stimulation electrodes that each have an area of at least 5 mm$^2$ and that applying the stimulation pulse to a heart segment having an area of at least 1 cm$^2$.

7. Apparatus for heart pacing with cardiac output modification, comprising:

one or more electrodes adapted to apply electrical signals to cardiac muscle segments; and signal generation circuitry adapted to apply an excitatory electrical pulse to at least one of the one or more electrodes to pace the heart and a non-excitatory stimulation pulse of a magnitude and at a timing at which it is unable to generate a propagating action potential to at least one of the one or more electrodes to modify the cardiac output, wherein the signal generation circuitry varies the extent of a portion of the area of the heart segment to which the non-excitatory stimulation pulse is applied.

8. A method for heart pacing with modification of cardiac contraction, comprising the steps of:

(a) implanting a pacing electrode in a first chamber of a subject's heart;

(b) implanting a non-excitatory stimulation electrode in another chamber of the subject's heart;

(c) conveying an excitatory electrical pulse to at least one of the electrodes to pace the heart; and (d) conveying a non-excitatory stimulation pulse of a magnitude and at a timing at which it is unable to generate a propagating action potential to at least one of the electrodes to modify the cardiac contraction.

9. A method for heart pacing with modification of cardiac contraction, comprising the steps of:

(a) implanting at least one non-excitatory stimulation electrode in each of a plurality of chambers of a subject's heart;

(b) conveying an excitatory electrical pulse to at least one of the electrodes to pace the heart; and (c) conveying a non-excitatory stimulation pulse of a magnitude and at a timing at which it is unable to generate a propagating action potential to at least one of the electrodes to modify the cardiac contraction.

10. A method for heart pacing with modification of cardiac contraction, comprising the steps of:

(a) fixing at least one electrode to the epicardium of a subject's heart;

(b) conveying an excitatory electrical pulse to at least one of the electrodes to pace the heart; and (c) conveying a non-excitatory stimulation pulse of a magnitude and at a timing at which it is unable to generate a propagating action potential to at least one of the electrodes to modify the cardiac contraction.

11. A method for heart pacing with modification of cardiac contraction, comprising the steps of:

(a) implanting at least one sensing electrode which senses cardiac activity in a subject's heart;

(b) conveying an excitatory electrical pulse to at least one of the electrodes to pace the heart; and (c) conveying a non-excitatory stimulation pulse of a magnitude and at a timing at which it is unable to generate a propagating action potential to at least one of the electrodes to modify the cardiac contraction, wherein step (c) comprises detecting a QT interval in an electrical signal received by the sensing electrode and generating a pulse responsive thereto.

12. A method for heart pacing with modification of cardiac contraction, comprising the steps of:

(a) applying one or more electrodes to a subject's heart;

(b) conveying an excitatory electrical pulse to at least one of the one or more electrodes to pace the heart;

(c) conveying a non-excitatory stimulation pulse of a magnitude and at a timing at which it is unable to generate a propagating action potential to at least one of the one or more electrodes to modify the cardiac contraction; and (d) applying a flow sensor which senses cardiac activity to the subject's body, wherein conveying the non-excitatory stimulation pulse comprises generating a pulse responsive to the activity.

13. A method for heart pacing with modification of cardiac contraction, comprising the steps of:

(a) applying one or more electrodes to a subject's heart;

(b) conveying an excitatory electrical pulse to at least one of the one or more electrodes to pace the heart;

(c) conveying a non-excitatory stimulation pulse of a magnitude and at a timing at which it is unable to generate a propagating action potential to at least one of the one or more electrodes to modify the cardiac contraction; and (d) applying a pressure sensor which senses cardiac activity to the subject's body, wherein conveying the non-excitatory stimulation pulse comprises generating a pulse responsive to the activity.

14. A method for heart pacing with modification of cardiac contraction, comprising the steps of:
   (a) applying one or more electrodes to a subject's heart;
   (b) conveying an excitatory electrical pulse to at least one of the one or more electrodes to pace the heart;
   (c) conveying a non-excitatory stimulation pulse of a magnitude and at a timing at which it is unable to generate a propagating action potential to at least one of the one or more electrodes to modify the cardiac contraction; and
   (d) applying an oxygen sensor which senses cardiac activity to the subject's body,
   wherein conveying the non-excitatory stimulation pulse comprises generating a pulse responsive to the activity.

15. A method for heart pacing with modification of cardiac contraction, comprising the steps of:
   (a) applying one or more electrodes to a subject's heart;
   (b) conveying an excitatory electrical pulse to at least one of the one or more electrodes to pace the heart;
   (c) conveying a non-excitatory stimulation pulse of a magnitude and at a timing at which it is unable to generate a propagating action potential to at least one of the one or more electrodes to modify the cardiac contraction; and
   (d) applying a temperature sensor which senses cardiac activity to the subject's body,
   wherein conveying the non-excitatory stimulation pulse comprises generating a pulse responsive to the activity.

16. A method for heart pacing with modification of cardiac contraction, comprising the steps of:
   (a) applying one or more electrodes to a subject's heart;
   (b) conveying an excitatory electrical pulse to at least one of the one or more electrodes to pace the heart; and
   (c) conveying a non-excitatory stimulation pulse of a magnitude and at a timing at which it is unable to generate a propagating action potential to at least one of the one or more electrodes to modify the cardiac contraction,
   wherein conveying the non-excitatory pulse comprises varying an area of the heart to which non-excitatory pulses are applied.

* * * * *

(12) EX PARTE REEXAMINATION CERTIFICATE (6214th)
United States Patent
Ben-Haim et al.

(10) Number: US 6,463,324 C1
(45) Certificate Issued: Apr. 29, 2008

(54) CARDIAC OUTPUT ENHANCED PACEMAKER

(75) Inventors: Shlomo Ben-Haim, Haifa (IL); Nissim Darvish, Haifa (IL); Yuval Mika, Haifa (IL); Maier Fenster, Petach Tikva (IL)

(73) Assignee: Johnson & Johnson Development Corporation, New Brunswick, NJ (US)

Reexamination Request:
No. 90/008,312, Nov. 1, 2006

Reexamination Certificate for:
Patent No.: 6,463,324
Issued: Oct. 8, 2002
Appl. No.: 09/254,900
Filed: Mar. 12, 1999

(22) PCT Filed: Jul. 9, 1997

(86) PCT No.: PCT/IL97/00236

§ 371 (c)(1),
(2), (4) Date: Mar. 12, 1999

(87) PCT Pub. No.: WO98/10832

PCT Pub. Date: Mar. 19, 1998

Related U.S. Application Data
(60) Provisional application No. 60/026,392, filed on Sep. 16, 1996.

(30) Foreign Application Priority Data
Sep. 17, 1996 (IL) .................................................. 119261

(51) Int. Cl.
*A61N 1/365* (2006.01)

(52) U.S. Cl. ............................................. 607/9; 607/17
(58) Field of Classification Search ................... None
See application file for complete search history.

(56) References Cited

U.S. PATENT DOCUMENTS

| | | |
|---|---|---|
| 3,572,345 A | 3/1971 | Auphan |
| 3,587,567 A | 6/1971 | Schiff |
| 3,933,147 A | 1/1976 | Du Vall et al. |
| 3,942,536 A | 3/1976 | Dahl et al. |
| 3,952,750 A | 4/1976 | Mirowski et al. |
| 4,030,509 A | 6/1977 | Heilman et al. |
| 4,106,494 A | 8/1978 | McEachern |
| 4,184,493 A | 1/1980 | Langer et al. |
| 4,202,340 A | 5/1980 | Langer et al. |
| 4,223,678 A | 9/1980 | Langer et al. |

(Continued)

FOREIGN PATENT DOCUMENTS

| | | |
|---|---|---|
| EP | 0314078 B1 | 10/1993 |
| JP | S62-275471 | 11/1987 |
| WO | WO 92/00716 | 1/1992 |
| WO | WO 93/18820 | 9/1993 |
| WO | WO 94/17855 | 8/1994 |

(Continued)

OTHER PUBLICATIONS

Cooper, W., "Postextrasystolic Potentiation: Do We Really Know What It Means and How to Use It?" Circulation, vol. 88, No. 6, Dec. 1993, pp. 2962–2971.

(Continued)

*Primary Examiner*—Beverly M. Flanagan

(57) ABSTRACT

This invention is an apparatus for heart packing with cardiac output modification, including one or more electrodes (27, 29) which apply electrical signals to muscle. Signal generation circuitry (26) applies an excitatory electrical pulse to at least one of the one or more electrodes to pace the heart and a non-excitatory stimulation pulse to at least one of the one or more electrode s to modify the cardiac output. Preferably the circuitry synchronizes the non-excitatory stimulation pulse with the pacing pulse.

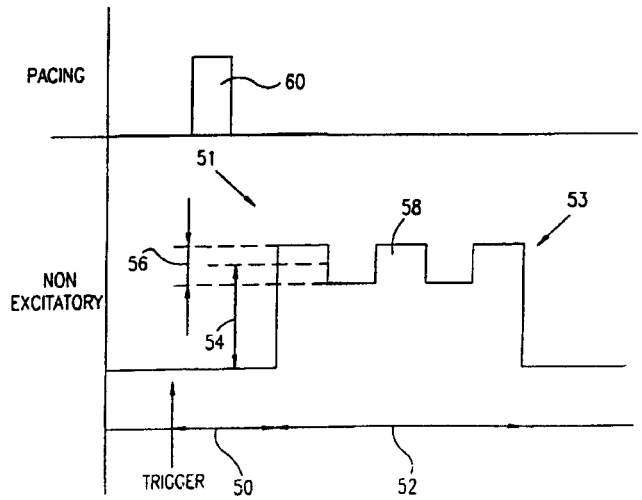

U.S. PATENT DOCUMENTS

| | | | |
|---|---|---|---|
| 4,237,895 A | 12/1980 | Johnson |
| 4,273,114 A | 6/1981 | Berkalow et al. |
| 4,312,354 A | 1/1982 | Walters |
| 4,316,472 A | 2/1982 | Mirowski et al. |
| 4,337,776 A | 7/1982 | Daly et al. |
| 4,384,585 A | 5/1983 | Zipes |
| 4,387,717 A | 6/1983 | Brownlee et al. |
| 4,403,614 A | 9/1983 | Engle et al. |
| 4,407,288 A | 10/1983 | Langer et al. |
| 4,411,268 A | 10/1983 | Cox |
| 4,440,172 A | 4/1984 | Langer |
| 4,543,738 A | 10/1985 | Mower |
| 4,543,956 A | 10/1985 | Herscovici |
| 4,554,922 A | 11/1985 | Prystowsky et al. |
| 4,559,946 A | 12/1985 | Mower |
| 4,566,456 A | 1/1986 | Koning et al. |
| 4,572,191 A | 2/1986 | Mirowski et al. |
| 4,628,934 A | 12/1986 | Pohndorf et al. |
| 4,651,716 A | 3/1987 | Forester et al. |
| 4,674,508 A | 6/1987 | DeCote |
| 4,679,572 A | 7/1987 | Baker, Jr. |
| 4,690,155 A | 9/1987 | Hess |
| 4,726,379 A | 2/1988 | Altman et al. |
| 4,765,341 A | 8/1988 | Mower et al. |
| 4,830,006 A | 5/1989 | Haluska et al. |
| 4,928,688 A | 5/1990 | Mower |
| 4,979,507 A | 12/1990 | Heinz et al. |
| 4,998,531 A | 3/1991 | Bocchi et al. |
| 5,002,052 A | 3/1991 | Haluska |
| 5,003,976 A | 4/1991 | Alt |
| 5,020,544 A | 6/1991 | Dahl et al. |
| 5,022,396 A | 6/1991 | Watanabe |
| 5,044,375 A | 9/1991 | Bach, Jr. et al. |
| 5,083,564 A | 1/1992 | Scherlag |
| 5,085,218 A | 2/1992 | Heil, Jr. et al. |
| 5,087,243 A | 2/1992 | Avitall |
| 5,097,832 A | 3/1992 | Buchanan |
| 5,111,815 A | 5/1992 | Mower |
| 5,129,394 A | 7/1992 | Mehra |
| 5,156,147 A | 10/1992 | Warren et al. |
| 5,156,149 A | 10/1992 | Hudrlik |
| 5,161,527 A | 11/1992 | Nappholz et al. |
| 5,163,428 A | 11/1992 | Pless |
| 5,199,428 A | 4/1993 | Obel et al. |
| 5,205,284 A | 4/1993 | Freeman |
| 5,213,098 A | 5/1993 | Bennett et al. |
| 5,284,491 A | 2/1994 | Sutton et al. |
| 5,305,745 A | 4/1994 | Zacouto |
| 5,320,642 A | 6/1994 | Scherlag |
| 5,320,643 A | 6/1994 | Roline et al. |
| 5,324,327 A | 6/1994 | Cohen |
| 5,327,887 A | 7/1994 | Nowakowski |
| 5,346,506 A | 9/1994 | Mower et al. |
| 5,353,800 A | 10/1994 | Pohndorf et al. |
| 5,366,486 A | 11/1994 | Zipes et al. |
| 5,368,040 A | 11/1994 | Carney |
| 5,370,665 A | 12/1994 | Hudrlik |
| 5,387,419 A | 2/1995 | Levy et al. |
| 5,391,192 A | 2/1995 | Lu et al. |
| 5,391,199 A | 2/1995 | Ben-Haim |
| 5,417,717 A | 5/1995 | Salo et al. |
| 5,431,688 A | 7/1995 | Freeman |
| 5,433,730 A | 7/1995 | Alt |
| 5,443,485 A | 8/1995 | Housworth et al. |
| 5,447,520 A | 9/1995 | Spano et al. |
| 5,447,525 A | 9/1995 | Powell et al. |
| 5,464,020 A | 11/1995 | Lerner |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,531,764 A | 7/1996 | Adams et al. |
| 5,540,722 A | 7/1996 | Clare et al. |
| 5,556,421 A | 9/1996 | Prutchi et al. |
| 5,568,809 A | 10/1996 | Ben-Haim |
| 5,571,143 A | 11/1996 | Hoegnelid et al. |
| 5,584,803 A | 12/1996 | Stevens et al. |
| 5,584,868 A | 12/1996 | Salo et al. |
| 5,601,609 A | 2/1997 | Duncan |
| 5,601,611 A | 2/1997 | Fayram et al. |
| 5,620,468 A | 4/1997 | Mongeon et al. |
| 5,626,622 A | 5/1997 | Cooper |
| 5,634,899 A | 6/1997 | Shapland et al. |
| 5,649,966 A | 7/1997 | Noren et al. |
| 5,651,378 A | 7/1997 | Matheny et al. |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,697,953 A | 12/1997 | Kroll et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben Haim |
| 5,738,105 A | 4/1998 | Kroll |
| 5,749,906 A | 5/1998 | Kieval et al. |
| 5,755,740 A | 5/1998 | Nappholz |
| 5,782,876 A | 7/1998 | Flammang |
| 5,782,881 A | 7/1998 | Lu et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,814,079 A | 9/1998 | Kieval |
| 5,871,506 A | 2/1999 | Mower |
| 6,136,019 A | 10/2000 | Mower |
| 6,141,587 A | 10/2000 | Mower |

FOREIGN PATENT DOCUMENTS

| | | |
|---|---|---|
| WO | WO 95/08316 | 3/1995 |
| WO | WO 96/16696 | 6/1996 |
| WO | WO 97/25098 | 7/1997 |
| WO | WO 97/25101 | 7/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/19719 | 5/1998 |
| WO | WO 99/03533 | 1/1999 |
| WO | WO 99/09971 | 3/1999 |
| WO | WO 00/27475 | 5/2000 |
| WO | WO 00/42914 | 7/2000 |
| WO | WO 00/53257 | 9/2000 |
| WO | WO 01/49367 | 7/2001 |
| WO | WO 01/52931 | 7/2001 |
| WO | WO 01/66183 | 9/2001 |
| WO | WO 01/91854 | 12/2001 |

OTHER PUBLICATIONS

Dillon, SM., "Optical Recordings in the Rabbit Heart Show that Defibrillation Strength Shocks Prolong the Duration of Depolarization and the Refractory Period" in Circ Res., 69 (3), Sep. 1991, pp. 842–856.

Fain, E.S., et al. "Improved Internal Defibrillation Efficacy with a Biphasic Waveform", American Heart Journal 117 (2), Feb. 1989, pp. 358–364.

Foster, A.H, et al., "Acute Hemodynamic Effects of Atrio–Biventricular Pacing in Humans", 1995, The Society of Thoracic Surgeons vol. 59, pp. 294–299.

Franz, M.R., "Bridging the Gap Between Basic and Clinical Electrophysiology: What Can be Learned from Monophasic Action Potential Recordings?", J. Cardiovasc Electrophysiol 5(8), Aug. 1994, pp. 699–710.

Franz, M.R., "Method and Theory of Monophasic Action Potential Recording", Prog. Cardiovasc Dis 33 (6), May–Jun. 1991, pp. 347–368.

Fromer et al., "Ultrarapid Subthreshold Stimulation for Termination of Atrioventricular Node Reentrant Tachycardia", Journal of the American College of Cardiology 20 (Oct. 1992), pp. 879–883.

Langberg, et al., "Identification Of Ventricular Tachycardia With Use Of The Morphology Of The Endocardial Electrogram", Therapy and Prevention, Arrhthmia, vol. 77, No. 6, Jun. 1988, pp. 1363–1369.

Jaremko, et al., "Advances Toward the Implantable Artificial Pancreas For Treatment Of Diabetes", Diabetes Care, vol. 21, No. 3, Mar. 1998, jpages 444–450.

Devedeux, et al., Uterine Electromyography: American Journal Obstet Gynecol, Current Development, Volumbe 169, No. 6, pp. 1636–1651.

Paul, VE., et al. "Automatic Recognition of Ventricular Arrythmias Using Temporal Electrogram Anaylsis" Pace, vol. 14, pp. 1265–1273, (1991).

Quizhen Xue et al., "Neural–Network–Based Adaptive Matched Filtering for QRS Detection", IEEE Transactions on Biomedical Engineering, vol. 39, No. 4, Apr. 1992.

Sweeny RJ, et al., abstract of "Countershock Strength–Duration Relationship for Myocardial Refractory Period Extension", Acad Emerg. Med., Jan. 1995, vol. 2, No. 1, pp. 57–62.

Sweeny RJ, et al., abstract of "Refractory Interval After Transcardiac Shocks During Ventricular Fibrillation", Circulation, Dec. 1996, vol. 94, No. 11, pp. 2947–2952.

Sweeny RJ, et al., abstract of "Ventricular Refractory Period Extension Caused by Defibrillation Shocks", Circulation, Sep. 1990, vol. 82, No. 3, pp. 965–972.

Soria, et al., "Cytosolic Calcium Oscillations And Insulin Release In Pancreatic Islets Of Langerhans", Diabetes & Metabolism (Paris), 1998, 24, pp. 37–40.

Gomis, et al., "Oscillatory Patterns Of Electrical Activity in Mouse Pancreataic Islets Of Langerhans Recorded In Vivo", Pflugers ARch—Eur J. Physiol (1996) 432, Springer–Verlag 1996, pp. 510–515.

Todd, et al., Subcutaneous Glucagon–Like Peptide I improves Postprandial Glycaemic Contorl Over A 3–Week Period In Patients With Early Type 2 Diabetes, Clinical Science (1998) 95, pp. 325–329.

Tian Y. Tsong, Electroporation Of Cell Membranes. Biophysical Journal, vol. 60, Aug. 1991, pp. 297–306.

Mercando, et al., Automated Detection Of Tachycardias By Antitachycardia Devices, Therapy, Chapter 100, pp. 943–948.

Hoffman, B.F. et al., "Effects of Postextrasystolic Potentiation on Normal & Failing Hearts", Bulletin of New York Academy of Medicine, 41 in 1965, pp. 498–534.

King, A. et al., The Inotropic Action of Paired Pulse Stimulation in the Normal and Failing Heart: An Experimental Study, Cardiovascular Research, vol. 2, Apr. 1968, pp. 122–129.

Knisley et al., "Prolgongation and Shortening of Action Potentials by Electrical Shocks in Frog Ventricular Muscle", American Journal of Physiology 6 (Heart Circ. Physiol. 35, 1994) pp. H2348–H2358.

Koller, et al., "Relation Between Repolarization and Refractoriness During Programmed Electrical Stimulation in the Human Right Ventricle", Circulation 91(9), 2378–2384, 1995.

Fu, et al., System Identification Of Electrically Coupled Smooth Muscles Cells: The Passive Electrical Properties, IEEE Transactions On Biomedical Engineering, vol. 38, No. 11, Nov. 1991.

Schirra et al., "Mechanisms Of The Antidiabetic Action Of Subcutaneous Glucagon–Like Peptide–1 (17–36)amide In Non–Insulin Dependent Diabetes Mellitus", Journal Of Endocrimology Ltd. 1998 156, jpages 177–186.

Palti, et al., "Islets Of Langerhans Generate Wavelike Electric Activity Modulated By Glucose Concentration", Diabetes, vol. 45, May 1996, pp. 595–601.

Knisley, et al., "Effect Of Field Stimulation On Cellular Repolarization in Rabbit Myocardium", Circulation Research, vol. 70, No. 4, Apr. 1992, pp. 707–715.

Pumir et al., "Control Of Rotating Waves in Cardiac Muscle: Analysis Of The Effect Of An Electrif Field", 1994, The Royal Society, 257, pp. 129–134.

Homer et al, Electrode For Recording Direction Of Activation, Conduction Velocity, And Monophasic Action Potential Of Myocardium, The American Physiological Society, 1997, pp. H1917–H1927.

Antoni, H. et al. "Polarization Effects of Sinusoidal 50–Cycle Alternating Current on Membrane Potential of Mammalian Cardiac Fibers", Pfluegers Arch. 314, pp. 274–291 (1970).

Bakker, P.F., et al., "Biventricular Pacing Improves Functional Capacity in Patients with End–Stage Congestive Heart Failure" Pace, vol. 17, Apr. 1995, Part 11, one page.

Bargheer K. et al., "Prolongation of Monophasic Action Potential Duration and the Refractory Period in the Human Heart by Tedisamil, a New Potassium–Blocking Agent", J. Eur Heart 15 (10), Oct. 1994, pp. 1409–1414.

Sakuma, et al., "A Model Analysis Of Aftereffects Of High–Intensity DC Stimulation On Action Potential Of Ventricular Muscle", IEEE Transactions On Biomedical Engineering, vol. 45, No. 2, Feb. 1998.

Lindstrom et al., "Intracellular Calcium Oscillations in A T–Cell Line After Exposure To Extremely–Low–Frequency Magnetic Fields With Variable Frequencles And Flux Densities", Bioelectromagnetics 16:41, p. 41–47.

Erol–Yilmaz, et al., "Reversed Remodelling Of Diated Left Sided Cardiomyopathy After Upgrading From VVIR to VVIR biventricular Pacing", Elsevier Science Ltd., on behalf of The European Society of Cardiology, 2002, vol. 4, pp. 445–449.

M. Yokoyama, "The Phase Of Supernormal Excitation In Relation To The Strength Of Subthreshold Stimuli", Heart Institute Of Japan, Jun. 1975, pp. 315–325.

Cheng, et al., "Calcium Sparks: Elementary Events Underlying Excitation–Contraction Coupling In Heart Muscle" Science, vol. 262, Oct. 29, 1993, pp. 740–744.

Coulton et al., "Magnetic Fields And Intracellular Calcium: Effects On Lymphocytes Exposed To Conditions For Cyclotron Resonance"., Phys. Med. Biol., 38, (1993), pp. 347–360.

Taniguchi, et al., "Inhomogeneity Of Cellular Activation Time And VMax in Normal Myocardial Tissue Under Electrical Field Stimulation"., American Physiological Society 1994, pp. H694–H705.

Talit, U. et al., "The Effect of External Cardiac Pacing on Stroke Volume", Pace 13, May 1990, pp. 598–560.

Wessale, J.L. et al., "Stroke Volume and Three Phase Cardiac Output Rate Relationship with Ventricular Pacing" Pace 13, May 1990, pp. 673–680.

Wirtzfeld, A. et al., "Physiological Pacing: Present Status and Future Developments", Pace 10 Jan.–Feb. 1987, Part I, pp. 41–57.

Gill, et al., "Refractory Period Extension During Ventricular Pacing At Fibrillatory Pacing Rates", Pace, vol. 20, Mar. 1997, Part I, pp. 647–653.

US 6,463,324 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2–10 and 16 is confirmed.

Claims 1 and 11–15 are determined to be patentable as amended.

New claims 17–41 are added and determined to be patentable.

1. Apparatus for heart pacing with cardiac output modification, comprising;
one or more electrodes adapted to apply electrical signals to cardiac muscle segments;
signal generation circuitry adapted to apply an excitatory electrical pulse to at least one of the electrodes to pace the heart and a non-excitatory stimulation pulse of a magnitude and at a timing at which it is unable to generate a propagating action potential to at least one of the one or more electrodes to modify the cardiac output; and
an electrode which senses cardiac electrical activity and is coupled to the signal generation circuitry,
wherein the circuitry detects a QT interval in the cardiac electrical activity *and which generates the non-excitatory pulse responsive thereto*.

11. A method for heart pacing with modification of cardiac contraction, comprising the steps of:
(a) implanting at least one sensing electrode which senses cardiac activity in a subject's heart;
(b) conveying an excitatory electrical pulse to at least one of the electrodes to pace the heart; and
(c) conveying a non-excitatory stimulation pulse of a magnitude and at a timing at which it is unable to generate a propagating action potential to at least one of the electrodes to modify the cardiac contraction,
wherein step (c) comprises detecting a QT interval in an electrical signal received by the sensing electrode and generating a *non-excitatory* pulse responsive thereto.

12. A method for heart pacing with modification of cardiac contraction, comprising the steps of:
(a) applying one or more electrodes to a subject's heart;
(b) conveying an excitatory electrical pulse to at least one of the one or more electrodes to pace the heart;
(c) conveying a non-excitatory stimulation pulse of a magnitude and at a timing at which it is unable to generate a propagating action potential to at least one of the one or more electrodes to modify the cardiac contraction; and
(d) applying a flow sensor which senses cardiac activity to the subject's body,
wherein conveying the non-excitatory stimulation pulse comprises generating a *non-excitatory* pulse responsive to the activity.

13. A method for heart pacing with modification of cardiac contraction, comprising the steps of:
(a) applying one or more electrodes to a subject's heart;
(b) conveying an excitatory electrical pulse to at least one of the one or more electrodes to pace the heart;
(c) conveying a non-excitatory stimulation pulse of a magnitude and at a timing at which it is unable to generate a propagating action potential to at least one of the one or more electrodes to modify the cardiac contraction; and
(d) applying a pressure sensor which senses cardiac activity to the subject's body,
wherein conveying the non-excitatory stimulation pulse comprises generating a *non-excitatory* pulse responsive to the activity.

14. A method for heart pacing with modification of cardiac contraction, comprising the steps of:
(a) applying one or more electrodes to a subject's heart;
(b) conveying an excitatory electrical pulse to at least one of the one or more electrodes to pace the heart;
(c) conveying a non-excitatory stimulation pulse of a magnitude and at a timing at which it is unable to generate a propagating action potential to at least one of the one or more electrodes to modify the cardiac contraction; and
(d) applying an oxygen sensor which senses cardiac activity to the subject's body,
wherein conveying the non-excitatory stimulation pulse comprises generating a *non-excitatory* pulse responsive to the activity.

15. A method for heart pacing with modification of cardiac contraction, comprising the steps of:
(a) applying one or more electrodes to a subject's heart;
(b) conveying an excitatory electrical pulse to at least one of the one or more electrodes to pace the heart;
(c) conveying a non-excitatory stimulation pulse of a magnitude and at a timing at which it is unable to generate a propagating action potential to at least one of the one or more electrodes to modify the cardiac contraction; and
(d) applying a temperature sensor which senses cardiac activity to the subject's body,
wherein conveying the non-excitatory stimulation pulse comprises generating a *non-excitatory* pulse responsive to the activity.

*17. Apparatus according to claim 1, wherein said circuitry determines whether to apply said signal responsive to said QT interval.*

*18. Apparatus according to claim 6 or claim 7, wherein said non-excitatory signal is configured to increase a contraction force of said heart.*

*19. A method according to any of claims 8–10 or 16, wherein said non-excitatory signal is configured to increase a contraction force of said heart.*

*20. Apparatus according to claim 6 or claim 7, wherein said non-excitatory signal is configured to increase a stroke volume of said heart in compensation for a reduction caused by said pacing.*

*21. The method according to any of claims 8–10, wherein said non-excitatory signal is configured to increase a stroke volume of said heart in compensation for a reduction caused by said pacing.*

22. The method according claim 21, comprising determining that said pacing reduces a cardiac output and configuring said non-excitatory signal in response to said determination.

23. The method according to any of claims 8–10 or 16, wherein said method is used to treat a heart with cardiac insufficiency.

24. Apparatus according to claim 6 or claim 7, wherein said apparatus is configured for use with a heart with cardiac insufficiency.

25. The method according to any of claims 8–10, wherein conveying an excitatory pulse comprises multi-point pacing.

26. Apparatus according to claim 6 or claim 7, wherein said apparatus is configured to provide multi-point pacing.

27. The method according to any of claims 8–10, comprising detecting fibrillation and applying a defibrillation pulse to the heart via at least one of said electrodes.

28. Apparatus according to claim 6 or claim 7, wherein said apparatus is configured to follow said non-excitatory pulse with a pulse of an opposite polarity configured to prevent at least one of tissue damage and electrode damage due to polarization caused by the non-excitatory pulse.

29. The method according to any of claims 8–10, comprising following said non-excitatory pulse with a pulse of an opposite polarity configured to prevent at least one of tissue damage and electrode damage due to polarization caused by the non-excitatory pulse.

30. Apparatus according to claim 6 or claim 7, wherein said apparatus comprises a defibrillator circuit.

31. The method according to claim 10, wherein fixing at least one electrode to the epicardium comprises implanting in a coronary blood vessel.

32. Apparatus according to claim 6 or claim 7, wherein said non-excitatory electrode is configured for transvascular operation from inside a coronary vessel.

33. The method according to any of claims 8–10 or 16, wherein conveying a non-excitatory stimulation pulse comprises affecting the contraction of tissue to which the pulse is applied.

34. Apparatus according to claim 6 or claim 7, wherein said non-excitatory stimulation pulse is configured to affect contraction in a cardiac segment to which it is applied.

35. The method according to claim 33, wherein conveying a non-excitatory stimulation pulse comprises affecting a current contraction of tissue to which the pulse is applied.

36. Apparatus according to claim 34, wherein said non-excitatory stimulation pulse is configured to affect a current contraction in a cardiac segment to which it is applied.

37. Apparatus according to any of claims 1–5, wherein modifying the cardiac output comprises increasing a stroke volume.

38. The method according to any of claims 11–15, wherein conveying said non-excitatory pulse comprises increasing a stroke volume.

39. Apparatus according to any of claims 1–5, wherein said circuitry is adapted to pace said heart at multiple locations using two or more of said one or more electrodes.

40. The method according to any of claims 8–16, wherein said method is applied on a non-arrhythmic heart, in a manner which increases cardiac output.

41. The method according to claim 25, wherein said multi-point pacing comprises multi-chamber pacing.

* * * * *